United States Patent [19]
Lasters et al.

[11] Patent Number: 5,747,449
[45] Date of Patent: May 5, 1998

[54] BOVINE PANCREATIC TRYPSIN INHIBITOR DERIVED INHIBITORS OF FACTOR XA

[75] Inventors: Ignace Lasters, Antwerpen; Marc De Maeyer, Groot-Bijgaarden, both of Belgium; William Charles Ripka, San Diego, Calif.

[73] Assignee: Corvas International, Inc., San Diego, Calif.

[21] Appl. No.: 86,630

[22] Filed: Jul. 1, 1993

Related U.S. Application Data

[63] Continuation-in-part of Ser. No. 913,232, Jul. 13, 1992.
[51] Int. Cl.$^6$ .......................... A61K 38/57; C07K 14/81
[52] U.S. Cl. ........................ 514/12; 530/324; 530/350
[58] Field of Search ......................... 435/69.1, 69.2; 530/350, 324; 514/12

[56] References Cited

U.S. PATENT DOCUMENTS

| | | | |
|---|---|---|---|
| 4,595,674 | 6/1986 | Tschesche et al. | 514/9 |
| 5,032,573 | 7/1991 | Auerswald et al. | 514/12 |
| 5,096,815 | 3/1992 | Ladner et al. | 435/69.1 |
| 5,106,833 | 4/1992 | Broze, Jr. et al. | 514/12 |
| 5,118,668 | 6/1992 | Auerswald et al. | 514/12 |
| 5,239,058 | 8/1993 | Vlasuk et al. | 530/324 |
| 5,373,090 | 12/1994 | Norris et al. | 530/324 |
| 5,618,915 | 4/1997 | Bjorn et al. | 530/324 |

FOREIGN PATENT DOCUMENTS

| | | |
|---|---|---|
| 0 307 592 | 8/1987 | European Pat. Off. |
| 0339942 | 11/1989 | European Pat. Off. |
| 2208511 | 4/1989 | United Kingdom |
| 9002809 | 3/1990 | WIPO |
| 94/07528 | 4/1994 | WIPO |

OTHER PUBLICATIONS

Cwirla et al., "Peptides on phage: A vast library of peptides for identifying ligants", 87 *Proc. Natl. Acad. Sci. USA* 6378–6382, 1990.
Hoad and Gczy, *J. Immun. Methods*, 136:269–278 (1991).
Roberts et al., *Proc. Natl. Acad. Sci. USA*, 89:2429 (1992).
Goldenberg and Creighton, *J. Mol. Biol.*, 179:527 (1984).
Stanssens et al., *Nucleic Acids Research* 17:4441–4454 (1989).
Creighton et al., "Biosynthesis Processing and Evolution of Bovine Pancreatic Typsin Inhibitor", Cold Spring Harbor, Symp. Quint. Biol., 52:511–519 (1987).
Stockmans et al., "Continuous Quantitative Monitoring of Mural...Thrombus...,", *Thromb. Haemo.*, 65(4):425–431 (Apr. 1991).
Schulz et al, *Principles of Protein Structure*, pp. 14–16 (1979).
Ascenzi et al., "Binding of BPTI (Kunitz Inhibitor) to ... Factor Xa", *Biol. Chem. Hoppe–Seyler*, 371:389–393 (May 1990).
Kido et al., "Kunitz–type Protease Inhibitor Found in Rat Mast Cells", *J. Biol. Chem.*, 263:18104–18109 (Dec. 1988).
Cwirla et al., Peptides on Phage ...., *Proc. Natl. Acad. Sci.*, 87:6378–6382 (Aug. 1990).
Vedvick et al., *J. Indus. Microbiol.*, 7:197–202 (1991).
Creighton et al., "Functional Evolutionary Divergence of Proteolytic Enzymes and Their Inhibitors", *TIBS*, 14:319–325 and 389–393 (Aug. 1989).
Fritz et al., *Arzneim.–Forsch/Drug Res.*, 33:479–494 (1983).
Bode et al. *Eur. J. Biochem.*, 144:185–190 (1984).
Schechter et al., *Biochem. Biophys. Res. Commun.*, 27:157 (1967).
McCafferty et al., *Nature*, 348:552–554 (1990).
Kunkel, *Proc. Natl. Acad. Sci. USA*, 82:488–492 (1985).
Sambrook et al. in Molecular Cloning—A Laboratory Manual, Cold Spring Harbor Laboratory Press, 1989, p. 4.29.
Sanger et al., *Proc. Natl. Acad. Sci. USA*, 74:5463–5467 (1977).
Mackie et al., "Normal Hemostasis and its Regulation", *Blood Reviews*, 3:237–250 (1989).
Laskowski et al., *Ann. Rev. Biochem.*, 49:593–626 (1980).
Remington's Pharmaceutical Sciences, Mack Publishing Co. (Ed., A.R. Gennaro 1985).
Marks et al., *J. Biol. Chem.*, 261:7115–7118 (1986).
Goldenberg et al., *Biochemistry*, 27:2481–2489 (1988).
Vieira et al., *Methods in Enzymology*, 153:3–11 (1987).
Weislander, *Anal. Biochem.*, 98:305–309 (1979).
Wu et al., Oligonucleotide Synthesis—A Practical Approach (Ed. Gait, M.J.), IRL Press, Oxford and Washington, D.C., pp. 135–151 (1984).
Zell et al., The EMBO Journal, 6:1809–1815 (1987).
Harlow et al., "Antibodies: A Laboratory Manual" (Cold Spring Harbor Laboratory 1988).
Furie et al., Cell, 53:505–518 (1988).
Boneu et al., Thrombosis and Haemostasis, 65:28–32 (1991).
Pelzer et al., Thrombosis and Haemostasis, 65:153–159 (1991).
ECAT Assay Procedures, A manual of Laboratory Techniques (Ed. Jespersen et al.), Kluwer Academic Publishers, Dorecht, The Netherlands (1992).

*Primary Examiner*—Charles L. Patterson, Jr.
*Assistant Examiner*—Kawai Lau
*Attorney, Agent, or Firm*—Lyon & Lyon LLP

[57] ABSTRACT

A compound derived from BPTI which inhibits Factor Xa with an inhibition constant less than 50 nM.

3 Claims, 7 Drawing Sheets

Pst205 (74-mer)
    GCTCCGGACT TCTGTCTCGA GCCACCGTAT ACCGGCCCCT GCAAGGCTCG
TATTATCCGC TACTTCTACA ACGC Pst206 (78-mer)
    CTTGGCGTTG TAGAAGTAGC GGATAATACG AGCCTTGCAG GGGCCGGTAT
ACGGTGGCTC GAGACAGAAG TCCGGAGC Pst207 (102-mer)
    CAAGGCCGGA CTCTGTCAGA CCTTTGTATA TGGTGGCTGC CGTGCAAAGC
GTAACAATTT CAAGTCGGCC GAGGACTGCA TGCGTACCTG TGGTGGCGCC TA Pst208 (102-mer)
    AGCTTAGGCG CCACCACAGG TACGCATGCA GTCCTCGGCC GACTTGAAAT
TGTTACGCTT TGCACGGCAG CCACCATATA CAAAGGTCTG ACAGAGTCCG GC

*Fig. 3*

Fig. 4A
```
GAATTCGAGC TCGAGCTTAC TCCCCATCCC CCTGTTGACA ATTAATC
EcoRI                                  -35
ATC GGCTCGTATA ATGTGTGGA ATTGTGAGCG ATAACAATT TCACA
        -10
CAGGA AACAGGATCC GCGGATCCGT GGAGAAAATA AA
              SacII              SD
```

```
ATG-AAA-CAA-AGC-ACT-ATT-GCA-CTG-GCA-CTC-TTA-CCG
Met Lys Gln Ser Thr Ile Ala Leu Ala Leu Leu Pro
-21 -20 -19 -18 -17 -16 -15 -14 -13 -12 -11 -10
```

```
                                          KpnI
TTA-CTG-TTT-ACC-CCT-GTG-ACA-AAA-GCG GTACC
Leu Leu Phe Thr Pro Val Thr Lys Ala
 -9  -8  -7  -6  -5  -4  -3  -2  -1
```

```
                         HindIII    XbaI
CGGGGATCCT CTAGAGTCGA CCTGCAGGCA TGCAAGCTTG GTCTAGA
```

Fig. 4B
```
    BspMII                                    AccI
GCT CCG GAC TTC TGT CTC GAG CCA CCG TAT ACC GGC
CGA GGC CTG AAG ACA GAG CTC GGT GGC ATA TGG CCG
Ala Pro Asp Phe Cys Leu Glu Pro Pro Tyr Thr Gly
 1   2   3   4   5   6   7   8   9  10  11  12

CCC TGC AAG GCT CGT ATT ATC CGC TAC TTC TAC AAC
GGG ACG TTC CGA GCA TAA TAG GCG ATG AAG ATG TTG
Pro Cys Lys Ala Arg Ile Ile Arg Tyr Phe Tyr Asn
13  14  15  16  17  18  19  20  21  22  23  24

StyI
GCC AAG GCC GGA CTC TGT CAG ACC TTT GTA TAT GGT
CGG TTC CGG CCT GAG ACA GTC TGG AAA CAT ATA CCA
Ala Lys Ala Gly Leu Cys Gln Thr Phe Val Tyr Gly
25  26  27  28  29  30  31  32  33  34  35  36

GGC TGC CGT GCA AAG CGT AAC AAT TTC AAG TCG GCC
CCG ACG GCA CGT TTC GCA TTG TTA AAG TTC AGC CGG
Gly Cys Arg Ala Lys Arg Asn Asn Phe Lys Ser Ala
37  38  39  40  41  42  43  44  45  46  47  48

SphI            KasI
GAG GAC TGC ATG CGT ACC TGT GGT GGC GCC TA
CTC CTG ACG TAC GCA TGG ACA CCA CCG CGG ATT CGA
Glu Asp Cys Met Arg Thr Cys Gly Gly Ala
49  50  51  52  53  54  55  56  57  58
```

BOVINE PANCREATIC TRYPSIN INHIBITOR DERIVED INHIBITORS OF FACTOR XA

This is a Continuation-in-Part application of U.S. patent application Ser. No. 07/913,232, filed on Jul. 13, 1992, the whole of which (including drawings) is hereby incorporated by reference herein.

FIELD OF INVENTION

The present invention relates to Bovine Pancreatic Trypsin Inhibitor derived inhibitors of Factor Xa, and methods for their preparation and therapeutic use.

BACKGROUND OF INVENTION

Bovine pancreatic trypsin inhibitor (also referred to as BPTI or Aprotinin) is a polypeptide having 58 amino acid residues, with internal cross linking by three disulfide bridges. Fritz, H. and Wunderer, G. (1983), Arzneim.-Forsch/Drug Res., 33: 479–494. The amino acid sequence of mature wild type BPTI is shown in (I).

```
                                                          (I)
  1   2   3   4   5   6   7   8   9  10  11  12
Arg Pro Asp Phe Cys Leu Glu Pro Pro Tyr Thr Gly 13  14  15  16  17  18  19  20  21  22  23  24
Pro Cys Lys Ala Arg Ile Ile Arg Tyr Phe Tyr Asn 25  26  27  28  29  30  31  32  33  34  35  36
Ala Lys Ala Gly Leu Cys Gln Thr Phe Val Tyr Gly 37  38  39  40  41  42  43  44  45  46  47  48
Gly Cys Arg Ala Lys Arg Asn Asn Phe Lys Ser Ala 49  50  51  52  53  54  55  56  57  58
Glu Asp Cys Met Arg Thr Cys Gly Gly Ala
```

SEQ ID NO: 1

In the mature folded protein, disulfide bonds are formed between the following pairs of cysteines: 5-55, 14-38 and 30-51.

The crystal structures of BPTI or BPTI variants complexed with trypsin, kallikrein, trypsinogen, and anhydrotrypsin show that two loops of the inhibitor form the interface with the serine proteases at residues 11-19 and 34-39. Bode, W., et al. (1984), Eur. J. Biochem., 144: 185–190. These residues are believed to be largely responsible for defining the specificity of the inhibitor for the target protease. In combination with the sequences of serine protease, the affinity and specificity of the protease inhibitors has been suggested to originate from sequence variations on both sides of the protease-inhibitor interface. Creighton, T. E. and Darby, N. J. (1989), TIBS, 14: 319–325.

In the art, the sequence for such a substrate or inhibitor of a serine protease is often represented by .... -P4-P3-P2-P1-P1'-P2'-P3'-P4'- ...., where P(P') are amino acids and the proteolytic cleavage site, in the case of substrates, is defined to occur between residues P1 and P1'. Schechter, I. and Berger, A., Biochem. Biophys. Res. Commun. (1967), 27: 157. The bond between the P-carbonyl and the P'-nitrogen in substrate is often referred to as the scissile bond.

The primary specificity for a serine protease is defined by the nature of the residue immediately preceding the scissile bond. The residue, P1, corresponds to lysine 15 in the wild type or natural BPTI sequence. Residues surrounding the scissile bond taken together with residue P1 are often referred to as the "active site loop" of BPTI which is illustrated in (II). Laskowski, M. Jr. and Kato, I. (1980), Ann. Rev. Biochem. 49, 593–626.

```
 12  13  14  15  16  17  18  19                  (II)
Gly Pro Cys Lys Ala Arg Ile Ile
 P4  P3  P2  P1  P1' P2' P3' P4'
```

SEQ ID NO: 2

It is believed that P2, P3, P4, P1', P2', P3' and P4' convey secondary specificity to the inhibitor allowing differentiation among different serine proteases. In BPTI, a second loop consisting of residues 34-39 also form a contact region with the active sites of certain serine proteases and may contribute to specificity.

Recombinant analogues of BPTI having a more specific inhibitory effect toward certain serine proteases have been reported. Polypeptides consisting of residues 3 to 58 of BPTI, with the amino acids at positions 15 and 42 in one analogue, and at 15, 17 and 42 in another analogue changed, were reported to inhibit, among other serine proteases, Factor Xa with relatively weak inhibition constants of 1800 and 150 nM. Norris K. and Petersen L. C., "Aprotinin Analogues and Process for the Production Thereof", EP 339,942 (published Nov. 2, 1989).

SUMMARY OF INVENTION

This invention concerns derivatives of BPTI engineered, as described below, to have potent inhibitory activity on Factor Xa, with substantially greater potency and specificity than previously reported BPTI-analog inhibitors for Factor Xa. Thus, in a first aspect, the invention features a compound derived from BPTI which inhibits Factor Xa with an inhibition constant ($K_i$) of less than 50 nM, preferably less than 20 nM, and more preferably less than 5 nM.

The term "compound" is meant to refer not only to polypeptide chains having an amino acid sequence of 58 amino acids as in the naturally occurring BPTI and its analogs, but also to compounds which contain one or more of those amino acids substituted at locations which may not be relevant to their activity as Factor Xa inhibitors. For example, such substitutions may include substitution of glycine for valine, or of one or more charged amino acids for similarly or oppositely charged amino acids, or may include deletion of one or more amino acids. In addition, one or more amino acids may be introduced into the polypeptide chain of BPTI-analogs such that their introduction has little or no effect on the Factor Xa inhibitory activity of the BPTI derivative. Such substitution may be with any of the naturally occurring amino acids, or with unnatural amino acids which may be manufactured by standard procedures known in the art. In a particularly preferred aspect of the invention, the compound is derived by synthesizing a nucleic acid sequence (e.g., DNA or RNA) which encodes the desired amino acid sequence of the BPTI-analog incorporating changes at specific chosen locations to produce Factor Xa inhibitory activity in the resulting encoded BPTI-analog. One example of such derivation is provided below, in which mutant BPTI compounds are formed by genetic engineering procedures.

The term "analog" indicates compounds found in non-bovine animals, which are analogous to BPTI and have the same basic 58 amino acid structure and inhibitory activities of BPTI.

Specifically, compounds which are BPTI-analogs and possess Factor Xa inhibitory activity include those having the structure Cys Leu Glu Pro Pro Tyr $X_{11}$ Gly $X_{13}$ $X_{14}$ $X_{15}$ $X_{16}$ $X_{17}$ $X_{18}$ $X_{19}$ $X_{20}$ Tyr Phe Tyr Asn Ala Lys Ala Gly Leu Cys Gln Thr Phe $X_{34}$ $X_{35}$ Gly Gly $X_{38}$ $X_{39}$ Ala Lys Arg Asn Asn $X_{45}$ $X_{46}$ Ser Ala Glu Asp Cys Met Arg Thr Cys SEQ ID NO:3 where:

$X_{11}$ is alanine, arginine, asparagine, aspartic acid, glutamic acid, glutamine, isoleucine, leucine, lysine, proline, serine, threonine, tryptophan, tyrosine, or valine;

$X_{13}$ is alanine, asparagine, aspartic acid, glutamine, glycine, histidine, isoleucine, leucine, methionine, phenylalanine, proline, serine, threonine, tryptophan, tyrosine, or valine;

$X_{14}$ is alanine, serine or cysteine. When $X_{14}$ is cysteine $X_{38}$ must be cysteine;

$X_{15}$ is arginine;

$X_{16}$ is alanine or glycine;

$X_{17}$ is alanine, asparagine, aspartic acid, glutamine, histidine, isoleucine, leucine, methionine, phenylalanine, proline, serine, threonine, tryptophan, tyrosine or valine;

$X_{18}$, $X_{19}$ and $X_{20}$ is any natural amino acid;

$X_{34}$ is alanine, arginine, asparagine, aspartic acid, cysteine, glutamic acid, glutamine, glycine, histidine, isoleucine, leucine, methionine, phenylalanine, proline, serine, threonine, tryptophan, tyrosine or valine;

$X_{35}$ is phenylalanine or tyrosine;

$X_{36}$ is alanine, glycine or serine;

$X_{38}$ is alanine, serine or cysteine. When $X_{38}$ is cysteine $X_{14}$ must be cysteine;

$X_{39}$ is glutamine, glycine, histidine, isoleucine, leucine, lysine, methionine, phenylalanine, proline, serine, threonine, tryptophan, tyrosine or valine;

$X_{45}$ is phenylalanine or tyrosine; and $X_{46}$ is any natural amino acid.

In a particularly preferred embodiment, examples of derived compounds include those having the structure $X_1$ Pro Asp Phe Cys Leu Glu Pro Pro Tyr $X_{11}$ Gly $X_{13}$ $X_{14}$ $X_{15}$ $X_{16}$ $X_{17}$ $X_{18}$ $X_{19}$ $X_{20}$ Tyr Phe Tyr Asn Ala Lys Ala Gly Leu Cys Gln Thr Phe $X_{34}$ $X_{35}$ Gly Gly $X_{38}$ $X_{39}$ Ala Lys Arg Asn Asn $X_{45}$ $X_{46}$ Ser Ala Glu Asp Cys Met Arg Thr Cys Gly Gly Ala SEQ ID NO:4 where:

$X_1$ is alanine or arginine;

$X_{11}$ is alanine, arginine, aspartic acid, glutamic acid, glutamine, leucine, proline, serine, threonine or valine;

$X_{13}$ is asparagine, aspartic acid, histidine, isoleucine, leucine, methionine, phenylalanine, proline, tryptophan, tyrosine, or valine;

$X_{14}$ is cysteine;

$X_{15}$ is arginine;

$X_{16}$ is alanine or glycine;

$X_{17}$ is alanine, asparagine, histidine, isoleucine, leucine, methionine, phenylalanine, serine, tryptophan or tyrosine;

$X_{18}$ is asparagine, histidine, isoleucine, leucine, phenylalanine, tyrosine or valine;

$X_{19}$ is arginine, asparagine, glutamine, histidine, isoleucine, leucine, lysine, proline, threonine or valine, $X_{20}$ is arginine, histidine, glutamic acid, glutamine, leucine, threonine or valine;

$X_{34}$ is alanine, glutamic acid, histidine, isoleucine, leucine, methionine, phenylalanine, serine, threonine, tryptophan, tyrosine or valine;

$X_{35}$ is phenylalanine or tyrosine;

$X_{36}$ is glycine;

$X_{38}$ is cysteine;

$X_{39}$ is glutamine, glycine, histidine, isoleucine, leucine, methionine, phenylalanine, serine, tryptophan, tyrosine or valine;

$X_{45}$ is phenylalanine; and $X_{46}$ is glutamic acid, lysine or tyrosine.

In a second aspect, the invention features an isolated nucleic acid segment encoding a compound as described above.

By "isolated" is meant that the nucleic acid does not occur naturally in nature, and is preferably located within a host cell genome, or an expression vector, or other vector such that it can be replicated and transcribed and translated to form a desired inhibitor of the invention. Generally, it indicates a homogenous preparation of nucleic acid.

In preferred embodiments, the nucleic acid segment includes at least 150 bases and is provided within a vector, for example, a plasmid, phasmid, cosmid, or phage, with a promoter region which controls transcription of the nucleic acid segment. In a related aspect, the invention features a host cell including such a vector.

The phrase "promoter region" and the term "transcription" are used in their art recognized manner.

A further aspect of the invention features a method for preparing a compound, as described above, by growing a host cell which includes a vector encoding the compound under conditions in which the vector causes expression of the compound within the cell. Preferably, the compound is linked to a secretion signal sequence which causes it to be secreted into the culture supernatant.

In a preferred embodiment, one method of preparing the compound includes: (a) initiating a culture in a nutrient medium of host cells transformed with an expression vector encoding the compound; (b) maintaining the culture for a sufficiently long time to allow production of the compound; and (c) recovering the compound from the culture.

A further aspect of the invention features a method for identifying a nucleic acid molecule expressing a BPTI-derived Factor Xa inhibitor as described above. In this method a potential Factor Xa inhibitor is expressed on the surface of a phage, and that phage is contacted with Factor Xa under conditions in which Factor Xa can bind to the inhibitor. Those phages which express effective inhibitors of Factor Xa are then identified and isolated by contacting the phage-bound Factor Xa with an antibody to Factor Xa which does not bind to the active site involved in binding with the Factor Xa inhibitor. The DNA sequence of that part of the phage DNA coding for the inhibitor is then determined, and that part of the phage DNA coding for the inhibitor isolated.

Yet another aspect of the invention features a phage expressing the desired compound of this invention as a fusion protein with a phage coat protein. Those phage having BPTI-derived Factor Xa inhibitors incorporated in the phage coat protein are identified as described above. Such phage are useful as intermediates in the process of isolating a nucleic acid segment encoding a Factor Xa inhibitor of this invention, using the method described above.

In another aspect the invention features a method for identifying a useful BPTI derivative which inhibits Factor Xa with an inhibition constant of less than 50 nM, most preferably the method further includes identifying an inhibitor that inhibits plasmin with a $K_i$ greater than 1 nM.

The present invention also includes pharmaceutically acceptable compositions prepared for storage and subsequent administration which include a pharmaceutically effective amount of an above-described compound in a pharmaceutically acceptable carrier or diluent.

The present invention also includes a method for preventing or treating a condition in a mammal characterized by an elevated Factor Xa activity. For example, the invention features a method for preventing or treating a condition in a mammal characterized by abnormal thrombosis.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a representation of the three dimensional interaction between the surface of a BPTI molecule and a Factor Xa substrate binding site. The dotted surface represents that part of the BPTI molecule which is expected to be in contact with the substrate binding sites of Factor Xa. The polypeptide chains of the BPTI molecule (below) and Factor Xa (above) are represented by black ribbons.

FIG. 2 is a diagrammatic representation of the vector pMa5-PI. The map of pMa5-PI contains the following features: (i) a ColE1 type origin of replication (ORI); (ii) the intergenic region of filamentous phage f1, including the origin of replication (f1 ORI); (iii) the beta-lactamase gene which confers resistance to ampicillin (bla); (iv) the chlioramphenicol acetyl transferase gene made nonfunctional by a mutation introducing an amber stop codon (cat-am); (v) the $P_{tac}$/phoA/BPTI expression cassette; (vi) two copies of the central transcription terminator of phage fd (fdT). The complementary vector pMc5-PI is identical to pMa5-PI except that the cat gene is functional (conferring resistance to chloamphenicol) and the bla gene contains an amber stop codon. The blown-up region shows the position of the $P_{tac}$ promoter, the DNA segment coding for the phoA secretion signal, the BPTI-derived gene, and the relevant restriction sites. A sequencing primer anneals to vector sequences immediately downstream of the BPTI coding region, as shown in the upper part of the figure, and can be used to determine the DNA sequence encoding a useful Factor Xa inhibitor of this invention.

FIG. 3 shows the DNA sequence (5' to 3') of the four oligonucleotides that were used to assemble the BPTI coding region.

FIG. 4 shows the Ptac/phoA/BPTI expression module of pMa5-PI. Specifically, panel (A) shows the relevant part of the recipient vector pMa/c5-19. The EcoRI/XbaI fragment is present in the multi-cloning site of pMa/c5-8 (Stanssens et al., Nucl. Acids Res. 17, 4441–4454, 1989). The -35 and -10 box of the $P_{tac}$ promoter, the Shine-Dalgarno (SD) sequence and secretion signal derived from the phoa gene as well as some relevant restriction sites are indicated. Panel (B) shows the double stranded BPTI-encoding fragment composed of the four chemically synthesized oligonucleotides. The BPTI-oligonucleotides were ligated with the pMc5-19 vector which had been opened with KpnI, treated with DNA polymerase I (Klenow fragment) and subsequently digested with HindIII. This fuses the 5'-end of the BPTI coding region to the phoA secretion signal while the HindIII-junction at the 3'-end generates an in-frame TAA translational stop codon.

Figure 7:
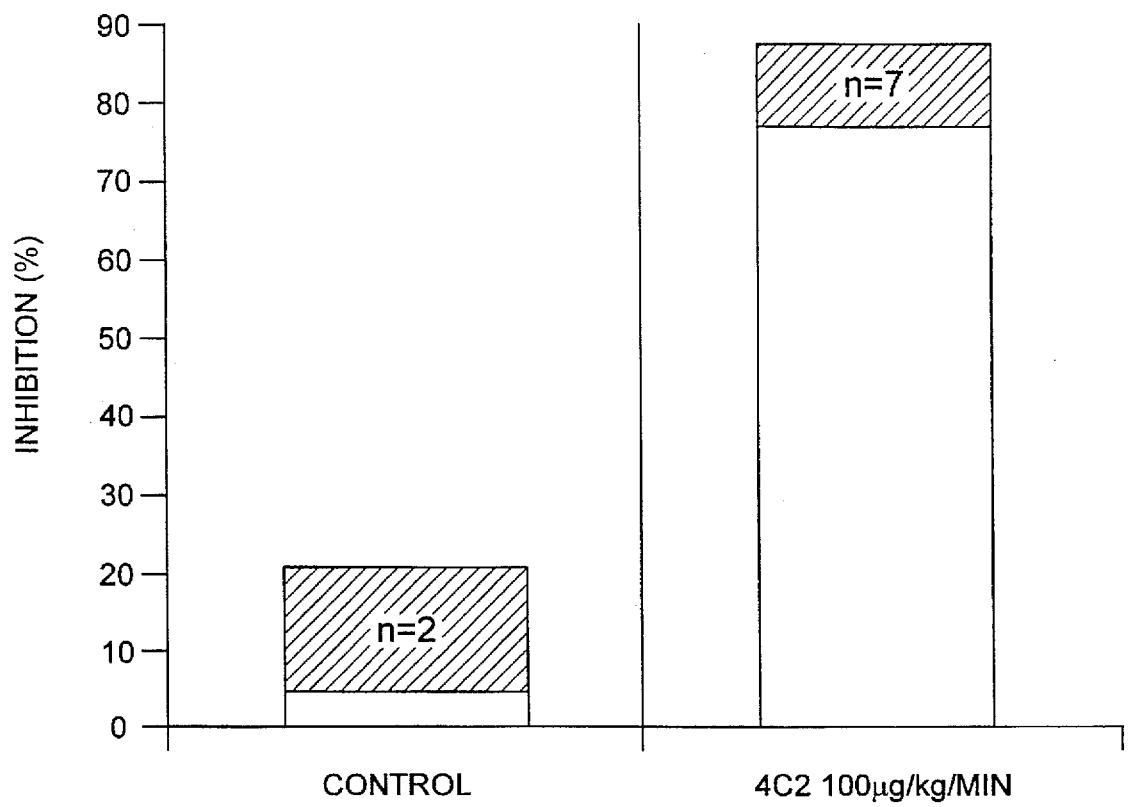

FIG. 7 is a graph representing inhibition of thrombus formation by 4c2 in the hamster crushed femoral vein model. Control animals were given an infusion of sterile saline. The mean value of n experiments is shown as a filled bar, the open part is the standard deviation.

BPTI-DERIVATIVES

Figure 1:
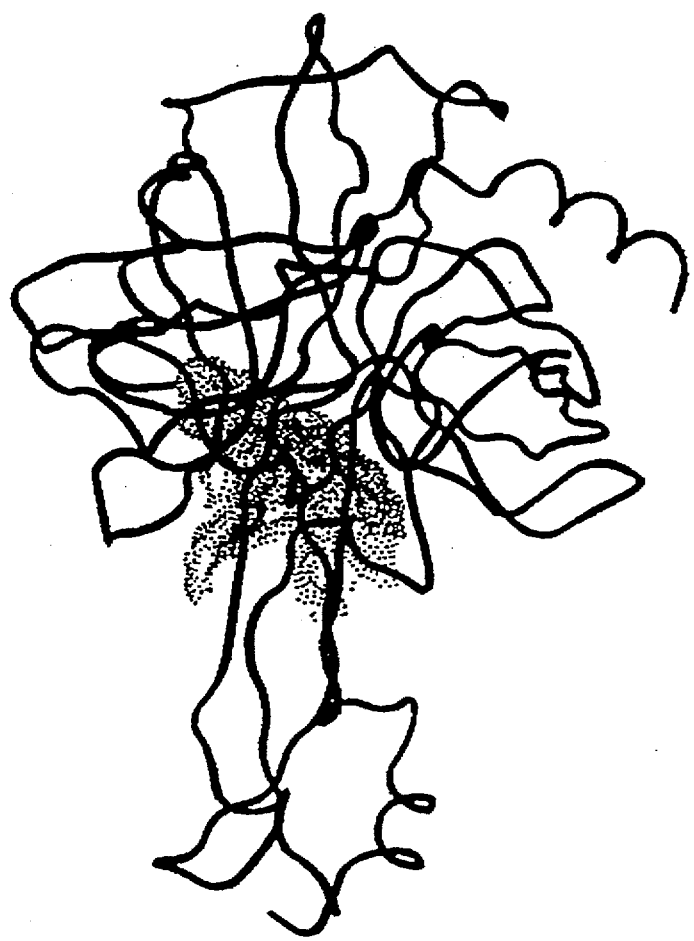

The specificity of BPTI for specific serine proteases (e.g., trypsin, plasmin) is determined by the nature of the amino acids which constitute that part of the surface of the BPTI molecule which is in contact with the protease substrate binding site. The dotted surface shown in FIG. 1 represents that part of the BPTI molecule which applicant predicts to be in contact with the substrate binding sites of Factor Xa. The polypeptide chain of the BPTI molecule is represented by the lower black ribbon. Compounds can be derived from BPTI, by replacing, inserting or deleting amino acids, in such a way that the contact surface is modified so as to be optimally compatible with the Factor Xa structure in shape, charge, polarity and hydrophobicity. The compounds thus derived from BPTI are potent Factor Xa inhibitors, whereas BPTI itself does not inhibit Factor Xa to any significant degree. Modifying, or even removing, amino acids outside the contact region should not affect the binding properties of the inhibitor as long as the structure of the contact region is not disturbed by such changes. From inspection of a BPTI model similar to the one represented in FIG. 1 it can be deduced that the shape of the contact region is largely, but not exclusively, defined by residues 11, 13, 14, 15, 16, 17, 18, 19, 20, 34, 35, 36, 38, 39; 45, and 46. Thus, BPTI-derived inhibitors of this invention have modifications at these sites to enhance their inhibitory activity, and may have changes at other sites which have little or no effect on such modifications. These inhibitors have the basic BPTI structure optimized to inhibit the activity of Factor Xa in vivo and in vitro. Such derivatives can be formed by standard procedures, as discussed below. Identification of optimal changes in the BPTI structure, however, can be performed by a randomized mutagenic procedure, or by systematic changes in BPTI amino acid sequence or structure. There follows examples of these procedures, which are not limiting in this invention.

Site-Directed Mutagenesis

Factor Xa inhibitors useful in this invention can be identified by site-directed mutagenesis of the BPTI gene expressed in a micro-organism. For example, a synthetic gene can be constructed in a vector using the methodology described in Stanssens et al., (1989), Nucl. Acids Res. 17: 4441–4454 and mutagenized by standard procedure. Specifically, the BPTI coding region was chemically synthesized so that the nucleotide sequence was adapted to match the E. coli codon usage (i.e., the synthesized gene were made devoid of AGA and AGG Arg-modulator-codons which adversely affect polypeptide production); strategically placed restriction sites which facilitate other genetic manipulations were incorporated; and Arg-1 was replaced by an Ala to allow proper processing by the E. coli signal peptidase.

Figure 2:
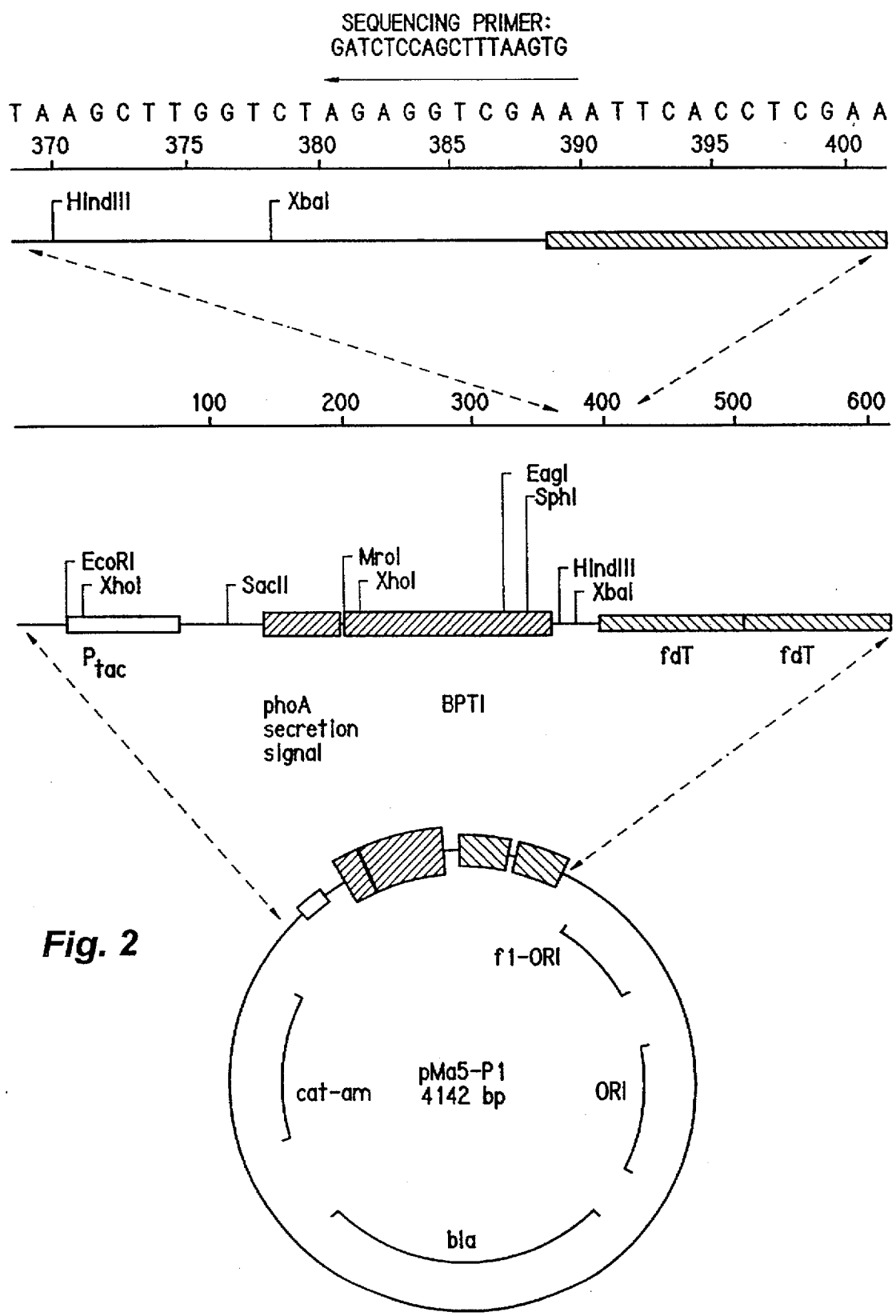
Figure 6:
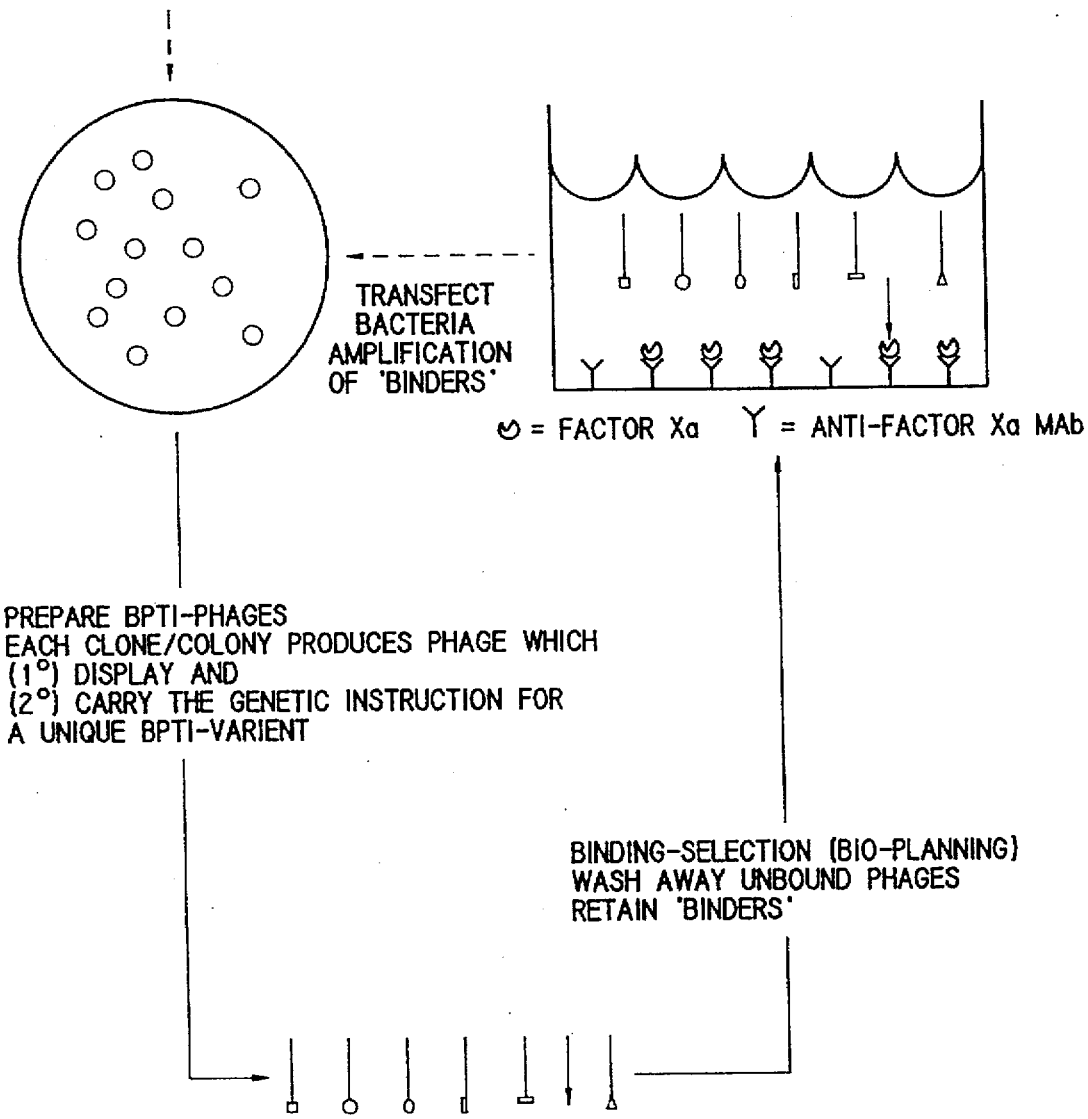
FIG. 6 is a diagram representing a method for isolating phages displaying a potent Factor Xa inhibitor of this invention.

To establish an E. coli expression system that would produce native, correctly folded and disulfide-bonded BPTI derivatives, the BPTI-derived mutant protein was directed to the periplasmic space by fusion of the gene to a DNA fragment encoding a secretion signal peptide. The BPTI derivative encoding oligonucleotides were ligated directly into pMa/c5-19. This vector (FIG. 2), contains an IPTG-inducible $P_{tac}$ promoter, and the secretion signal-encoding part of the alkaline phosphatase (phoA) gene which can be made accessible by virtue of a KpnI site. Stanssens et al., Nucl. Acids Res. 17, 4441–4454, 1989. The sequences of four oligonucleotides used to assemble a BPTI derivative-coding region are shown in FIG. 3. FIG. 4 shows the relevant parts of the pMa/c5-19 vector and the complete BPTI derivative-encoding nucleic acid fragment. The construction of the BPTI-analog gene in the pMa/c5-19 vector is described in more detail in Example 1, below.

schematic way how the mutant BPTI protein is displayed on the surface of the phage. A diagram of the selection procedure (or panning) for phages expressing Factor Xa inhibitors is shown in FIG. 6. The Kunkel method was used to engineer the Gene III variant (III) by oligonucleotide directed mutagenesis. Kunkel, (1985) Proc. Natl. Acad. Sci. USA, 82: 488–492.

```
        secretion signal       BspMII              KasI    mature     P-III                   (III)
        CAC TCC GCT CCG GAC ACT AGT GGT GGC GCC GCT GAA  SEQ ID NO: 5
        His Ser Ala Pro Asp            Gly Gly Ala Ala Glu
                BPTI  1   2   3             56  57  58
                                15
```

The synthesis and secretion of the BPTI-derived protein was shown by measuring trypsin inhibition. The amino-terminal sequence of the purified protein was (Ala Pro Asp Phe) indicating that the phoA-BPTI precursor underwent correct processing.

The vectors pMa5-PI and pMc5-PI harbor the intergenic region of filamentous phage f1, thus allowing expression, oligonucleotide-directed mutagenesis, and sequencing to be carried out from the same replicon. Mutation construction experiments were carried out essentially as described by Stanssens et al., Nucl. Acids Res. 17, 4441–4454, 1989. The construction of the genes encoding the inhibitory BPTI-derived compounds 4c2 and 44c3 is described in Example 2.

For large scale production, the specific inhibitor-encoding genes can be transferred to a secretion production system such as, for example, the *Pichia yeast* expression system (Phillips Petroleum Company). The construction of one particular BPTI-derived gene in the Pichia expression vectors is described in Example 3. Recombinant protein can be purified from the culture medium using standard methods, such as ion exchange chromatography and affinity chromatography. An example of a purification protocol is given in Example 4.

Random Mutagenesis, Phage Display Method

In this method, the BPTI gene (from the pMa/c5-PI vector, described above) or an appropriate BPTI-derived gene was introduced into construction III, above, as a BspMII-KasI fragment. To allow random mutagenesis of the amino acid residues 15 through 20 of BPTI, a new vector, pMc5-PI28c5, was constructed containing a BPTI-derived gene which carries a PstI and ApaI site as well as a frame shift. The 28c5 mutant gene was constructed making use of the following oligonucleotides:

Pst238: GTT ACG CTT TGC CCT GCA GCC ACC SEQ ID NO:6

Pst239: GCC TTG CAG GGG CCC GGT ATA CGG TGG SEQ ID NO:7

The phage having the 28c5 mutant gene is called fd-cat28c5. The frame shift was corrected when the mutagenic oligonucleotides were inserted into fd-cat28c5. In this way, a large background of wild type BPTI-expressing phages is avoided in cases of incomplete insertion of the oligonucleotides.

The mutagenic oligonucleotide (Pst240) inserted into fd-cat28c5 contains the degenerate coding sequence shown in (IV), where R is an equimolar mixture of A and G; N is either of G, A, T and C; and K is either G and T.

```
        Pst240:  TAT ACC GGG CCC TGC ARG NNK NNK NNK NNK NNK TAC    (IV)
                 TTC TAC AAC GCC AAG GCC GGA CTC TGT  SEQ ID NO: 8
```

Recombinant DNA molecules encoding the Factor Xa inhibitors of this invention can also be identified by a random mutagenesis approach, where appropriate DNA segments are changed in such a way as to allow all the residue positions 11-20, 34-39 and 45-46 of (I) to be replaced by all amino acids either individually or in blocks of two or more residues. A large number of mutated polypeptides can be generated by expressing the polypeptide as a fusion protein displayed on the surface of a cell, microorganism or phage. The polypeptides with the desired binding properties can be identified and isolated by a process called "panning". Cwirla, S. E., et al. (1990), Proc. Natl. Acad. Sci. USA, 87: 6378–6382. The DNA molecules corresponding to the thus identified Factor Xa inhibitors are purified, sequenced and transferred to the appropriate vector for overproduction and purification of the encoded protein.

Figure 5:
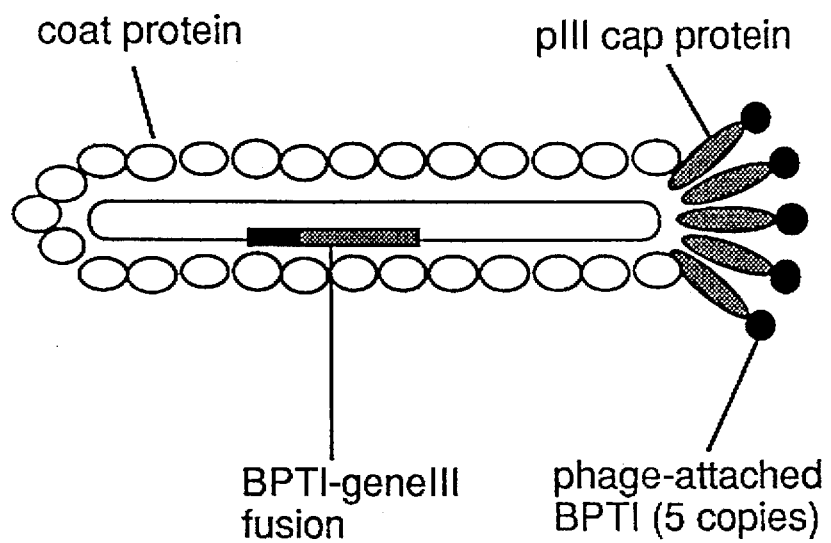
FIG. 5 is a schematic diagram of a filamentous phage displaying five copies of a mutant BPTI-derived protein fused to the PIII coat protein.

For example, the BPTI gene can be fused to the P-III coat protein of the filamentous *E. coli* phage fd-cat. McCafferty et al. (1990), Nature 348: 552–554. FIG. 5 shows in a This allows replacement of Lys15 with either an Arg or Lys; and of Ala16, Arg17, Ile18, Ile19, Arg20 with any of the twenty natural amino acids.

The mutagenic oligonucleotide (PST240), and a second overlapping oligonucleotide (PST241, V), were converted into a double stranded DNA fragment using Taq-polymerase.

```
        Pst241:  CTT TGC CCT GCA GCC ACC ATA TAC AAA GGT CTG ACA    (V)
                 GAG TCC GGC CTT GGC GTT GTA GAA GTA  SEQ ID NO: 9
                                55
```

Following digestion with ApaI and PstI, the mutagenic fragment was ligated to the large gel-purified ApaI-PstI fragment of fd-cat28c5 replicative form DNA. Ligated samples were used to electroporate WK6 *E. coli* cells. The phages produced by these cells were panned as described in Example 5. After several rounds, preferably three, of panning and amplification, individual clones were isolated. Cwirla, S. E., et al. (1990), Proc. Natl. Acad. Sci. USA, 87: 6378–6382. The phage DNA was purified using standard techniques (Sambrook et al. in Molecular Cloning-a Laboratory Manual, Cold Spring Harbor Laboratory Press, 1989, p. 4.29) and the DNA sequences of the mutant BPTI genes determined (Sanger, F. et al. (1977) Proc. Natl. Acad. Sci. USA 74, 5463–5467).

For expression of the recombinant Factor Xa inhibitor in a microorganism or in eukaryotic cells, a DNA fragment can be isolated from the phage DNA after digestion with BspMII and KasI, using the restriction sites indicated in (III), and transferred to an appropriate expression vector. Preferred expression vectors are the pMa/c-5-19 type of vectors for expression in *E. coli* (see FIG. 2), and the pHILS1 and pHILD4 vectors for the Pichia yeast expression system (Phillips Petroleum Company) (see Example 3).

Preferred BPTI-Derived Compounds

The preferred compounds of the present invention are those having a $K_i$ for Factor Xa smaller than 50 nM. Examples of these compounds are given in the following list. These inhibitors have essentially the same amino acid sequence as BPTI except for the substitutions shown between brackets.

BPTI (13Ile 15Arg 17Tyr 19Thr 39Leu 46Glu) SEQ ID NO:10,
BPTI (1Ala 13Ile 15Arg 17Tyr 19Thr 39Leu 46Glu) SEQ ID NO:11,
BPTI (1Ala 13Ile 15Arg 17Tyr 19Thr 39Leu) SEQ ID NO:12,
BPTI (1Ala 15Arg 17Tyr 19Thr 39Leu 46Glu) SEQ ID NO:13,
BPTI (1Ala 13Ile 15Arg 17Tyr 19Thr 32Arg 39Leu 46Glu) SEQ ID NO:14,
BPTI (1Ala 11Glu 13Ile 15Arg 17Tyr 19Thr 39Leu 46Glu) SEQ ID NO:15,
BPTI (1Ala 13Ile 15Arg 17Tyr 39Leu) SEQ ID NO:16,
BPTI (1Ala 13Phe 15Arg 17Tyr 19Thr 39Leu) SEQ ID NO:17,
BPTI (1Ala 13Ile 15Arg 17Tyr 19Thr 39Phe) SEQ ID NO:18,
BPTI (1Ala 13Ile 15Arg 17Phe 19Thr 39Leu) SEQ ID NO:19,
BPTI (1Ala 15Arg 17Tyr 19Thr 39Tyr) SEQ ID NO:20,
BPTI (1Ala 15Arg 17Tyr 19Thr 39Ile) SEQ ID NO:21,
BPTI (1Ala 15Arg 17Tyr 19Thr 39Trp) SEQ ID NO:22,
BPTI (1Ala 15Arg 17Tyr 19Thr 39Phe) SEQ ID NO:23,
BPTI (1Ala 15Arg 17Tyr 19Thr 39His) SEQ ID NO:24,
BPTI (1Ala 15Arg 17Tyr 19Thr 39Ser) SEQ ID NO:25,
BPTI (1Ala 15Arg 17Tyr 19Thr 39Val) SEQ ID NO:26,
BPTI (15Arg 16Gly 17Trp 18Phe 19Arg 20Gln) SEQ ID NO:27,
BPTI (13Ile 15Arg 16Gly 17Trp 18Phe 19Arg 20Gln 39Leu) SEQ ID NO:28,
BPTI (11Glu 13Ile 15Arg 16Gly 17Trp 18Phe 19Arg 20Gln 39Leu) SEQ ID NO:29,
BPTI (15Arg 16Ala 17His 18Ile 19Thr 20Thr) SEQ ID NO:30,
BPTI (13Ile 15Arg 16Ala 17His 18Ile 19Thr 20Thr 39Leu) SEQ ID NO:31,
BPTI (11Glu 13Ile 15Arg 16Ala 17His 18Ile 19Thr 20Thr 39Leu) SE ID NO:32,
BPTI (15Arg 16Ala 17His 18His 19Leu 20Val) SEQ ID NO:33,
BPTI (13Ile 15Arg 16Ala 17His 18His 19Leu 20Val 39Leu) SEQ ID NO:34,
BPTI (11Glu 13Ile 15Arg 16Ala 17His 18His 19Leu 20Val 39Leu) SEQ ID NO:35,
BPTI (15Arg 16Ala 17His 18His 19Arg 20Glu) SEQ ID NO:36,
BPTI (13Ile 15Arg 16Ala 17His 18His 19Arg 20Glu 39Leu) SEQ ID NO:37,
BPTI (11Glu 13Ile 15Arg 16Ala 17His 18His 19Arg 20Glu 39Leu) SEQ ID NO:38,
BPTI (15Arg 16Ala 17His 18Ile 19Arg 20Gln) SEQ ID NO:39,
BPTI (13Ile 15Arg 16Ala 17His 18Ile 19Arg 20Gln 39Leu) SEQ ID NO:40,
BPTI (11Glu 13Ile 15Arg 16Ala 17His 18Ile 19Arg 20Gln 39Leu) SEQ ID NO:41,
BPTI (15Arg 16Gly 17His 18His 19Arg 20Glu 26Asn) SEQ ID NO:42,
BPTI (13Ile 15Arg 16Gly 17His 18His 19Arg 20Glu 26Asn 39Leu) SEQ ID NO:43,
BPTI (11Glu 13Ile 15Arg 16Gly 17His 18His 19Arg 20Glu 26Asn 39Leu) SEQ ID NO:44,
BPTI (15Arg 16Ala 17Tyr 18Phe 19Asn 20Leu) SEQ ID NO:45,
BPTI (13Ile 15Arg 16Ala 17Tyr 18Phe 19Asn 20Leu 39Leu) SEQ ID NO:46,
BPTI (11Glu 13Ile 15Arg 16Ala 17Tyr 18Phe 19Asn 20Leu 39Leu) SEQ ID NO:47,
BPTI (15Arg 16Ala 17His 18Val 19Arg 20His) SEQ ID NO:48,
BPTI (13Ile 15Arg 16Ala 17His 18Val 19Arg 20His 39Leu) SEQ ID NO:49, and
BPTI (11Glu 13Ile 15Arg 16Ala 17His 18Val 19Arg 20His 39Leu) SEQ ID NO:50,
BPTI (13Ile 15Arg 17Asn 18Phe 19Lys 39Leu 46Glu) SEQ ID NO:51,
BPTI (13Ile 15Arg 17Ser 18Phe 19Asn 39Leu 46Glu) SEQ ID NO:52,
BPTI (13Ile 15Arg 17Ala 18Phe 19Lys 39Leu 46Glu) SEQ ID NO:53,
BPTI (13Ile 15Arg 16Ser 17Tyr 18Phe 19Lys 39Leu 46Glu) SEQ ID NO:54,
BPTI (13Ile 15Arg 17Ser 18Phe 19Lys 39Leu 46Glu) SEQ ID NO:55,
BPTI (13Ile 15Arg 17His 18Tyr 19Lys 39Leu 46Glu) SEQ ID NO:56,
BPTI (13Ile 15Arg 17Ser 18Phe 19Thr 39Leu 46Glu) SEQ ID NO:57,
BPTI (13Ile 15Arg 17Ser 18Tyr 19Thr 39Leu 46Glu) SEQ ID NO:58,
BPTI (13Ile 15Arg 17Ser 18Tyr 19Lys 39Leu 46Glu) SEQ ID NO:59,
BPTI (13Ile 15Arg 17Met 18Phe 19His 39Leu 46Glu) SEQ ID NO:60,
BPTI (13Ile 15Arg 17Ile 18Tyr 19Val 39Leu 46Glu) SEQ ID NO:61,
BPTI (13Ile 15Arg 17Asn 18Phe 19Asn 39Leu 46Glu) SEQ ID NO:62,
BPTI (13Ile 15Arg 17Tyr 18Tyr 19Lys 39Leu 46Glu) SEQ ID NO:63,
BPTI (13Ile 15Arg 17Ala 18Phe 19Lys 39Leu 46Glu) SEQ ID NO:64,
BPTI (13Ile 15Arg 17Leu 18His 39Leu 46Glu) SEQ ID NO:65,
BPTI (13Ile 15Arg 17Ile 18Tyr 19Lys 39Leu 46Glu) SEQ ID NO:66,
BPTI (13Ile 15Arg 17Ala 18Phe 19Asn 39Leu 46Glu) SEQ ID NO:67,
BPTI (13Ile 15Arg 17Phe 18Tyr 19Lys 39Leu 46Glu) SEQ ID NO:68,
BPTI (13Ile 15Arg 17Leu 18Tyr 19Lys 39Leu 46Glu) SEQ ID NO:69,
BPTI (11Asp 15Arg 17Leu 18His 19Leu 34Tyr 39Leu 46Glu) SEQ ID NO:70,
BPTI (11Pro 13Tyr 15Arg 17Leu 18His 19Leu 34Thr 39His 46Glu) SEQ ID NO:71,
BPTI (11Thr 13Pro 15Arg 17Leu 18His 19His 34Phe 39Phe 46Glu) SEQ ID NO:72, BPTI (11Pro 13Ile 15Arg 17Leu 18His 19Pro 34His 39Leu 46Glu) SEQ ID NO:73, BPTI (11Val 13Ile 15Arg 17Leu 18His 19Thr 34Ser 39Phe 46Glu) SEQ ID NO:74, BPTI (11Ser 13Leu 15Arg 17Leu 18His 19Lys 34Tyr 39Tyr 46Glu) SEQ ID NO:75, BPTI (11Leu 13Ile 15Arg 17Leu 18His 19Thr 34Ser 39Leu 46Glu) SEQ ID NO:76, BPTI (11Pro 13Ile 15Arg 17Leu 18His 19Lys 34His 39Phe 46Glu) SEQ ID NO:77, BPTI (11Ser 13Leu 15Arg 17Leu 18His 19Lys 34Tyr 39Phe 46Glu) SEQ ID NO:78, BPTI (11Pro 13Ile 15Arg 17Leu 18His 19Lys 34Tyr 39Met 46Glu) SEQ ID NO:79, BPTI (11Glu 13Met 15Arg 17Ile 18His 19Lys 34Thr 39Met 46Glu) SEQ ID NO:80, BPTI (11Pro 13Val 15Arg 17Leu 18His 19Lys 34Ser 39Gln 46Glu) SEQ ID NO:81, BPTI (11Arg 13Val 15Arg 17Ile 18His 19Lys 34Leu 39Met 46Glu) SEQ ID NO:82, BPTI (11Pro 13Leu 15Arg 17Leu 18His 19Lys 34Tyr 39Tyr 46Glu) SEQ ID NO:83, BPTI (11Ala 13Tyr 15Arg 17Leu 18His 19Lys 34Tyr 39Phe 46Glu) SEQ ID NO:84, BPTI (11Arg 13Val 15Arg 17Ile 18His 19Gln 34Ile 39Met 46Glu) SEQ ID NO:85, BPTI (11Thr 13Tyr 15Arg 17Leu 18His 19Lys 34Tyr 39Phe 46Glu) SEQ ID NO:86, BPTI (11Thr 13Ile 15Arg 17Leu 18His 19Lys 34Trp 39Leu 46Glu) SEQ ID NO:87, BPTI (11Gln 13Ile 15Arg 17Leu 18His 19Lys 34Met 39Leu 46Glu) SEQ ID NO:88, BPTI (11Pro 13Ile 15Arg 17Leu 18His 19Lys 34Tyr 39Met 46Glu) SEQ ID NO:89, BPTI (11Glu 13Leu 15Arg 17Leu 18His 19Lys 34Tyr 39Phe 46Glu) SEQ ID NO:90, BPTI (11Glu 13Phe 15Arg 17Tyr 18Phe 19Lys 34Thr 39Phe 46Glu) SEQ ID NO:91, BPTI (11Val 13Asp 15Arg 17Tyr 18Phe 19Lys 35Phe 39Leu 46Glu) SEQ ID NO:92, BPTI (11Glu 13Phe 15Arg 17His 18Phe 19Lys 32Ser 39Phe 46Glu) SEQ ID NO:93, BPTI (9Ala 11Glu 13Tyr 15Arg 17Tyr 18Ile 19Lys 23Phe 34His 39Phe 46Glu) SEQ ID NO:94, BPTI (11Thr 13His 15Arg 17Phe 18Phe 19Thr 39Phe 46Glu) SEQ ID NO:95, BPTI (11Thr 13His 15Arg 17Tyr 18Phe 19Lys 34Ile 39Phe 46Glu) SEQ ID NO:96, BPTI (9Ala 11Glu 13Phe 15Arg 17Tyr 18Phe 39Phe 46Glu) SEQ ID NO:97, BPTI (10His 11Ser 13Ile 15Arg 17Tyr 18Phe 19Lys 39Phe 46Glu) SEQ ID NO:98, BPTI (11Glu 13Ile 15Arg 17Leu 18Phe 19Thr 34His 39Leu 46Glu) SEQ ID NO:99, BPTI (10Ser 11Glu 13Ile 15Arg 17Tyr 18His 19Lys 39Leu 46Glu) SEQ ID NO:100, BPTI (11Glu 13Asn 15Arg 17Phe 18Phe 19Arg 34Ile 39Leu 46Glu) SEQ ID NO:101, BPTI (11Leu 13Ile 15Arg 17Tyr 18Leu 19Lys 34Tyr 39Leu 46Glu) SEQ ID NO:102, BPTI (11Glu 13Asn 15Arg 17Tyr 18Leu 19Lys 34Ala 39Phe 46Glu) SEQ ID NO:103, BPTI (11Glu 13Ile 15Arg 17Tyr 18Phe 19Lys 34Ser 39Phe 46Glu) SEQ ID NO:104, BPTI (11Glu 13Ile 15Arg 17Phe 18Asn 19Lys 39Leu 46Glu) SEQ ID NO:105, BPTI (8Ser 11Ala 13Ile 15Arg 17Tyr 19Lys 34Tyr 39Phe 46Glu) SEQ ID NO:106, BPTI (11Glu 13Ile 15Arg 17Leu 18His 19Lys 34Tyr 39Leu 46Glu) SEQ ID NO:107, BPTI (11Glu 13Ile 15Arg 17Tyr 18Phe 19Lys 34Glu 39Leu 46Glu) SEQ ID NO:108, More preferred are those compounds characterized by a Ki for Factor Xa smaller than 10 nM. These include:

BPTI (13Ile 15Arg 17Tyr 19Thr 39Leu 46Glu) SEQ ID NO:109,

BPTI (1Ala 13Ile 15Arg 17Tyr 19Thr 39Leu 46Glu) SEQ ID NO:110,

BPTI (1Ala 13Ile 15Arg 17Tyr 19Thr 39Leu) SEQ ID NO:111,

BPTI (1Ala 15Arg 17Tyr 19Thr 39Leu 46Glu) SEQ ID NO:112,

BPTI (1Ala 13Ile 15Arg 17Tyr 19Thr 32Arg 39Leu 46Glu) SEQ ID NO:113,

BPTI (1Ala 13Ile 15Arg 17Tyr 39Leu) SEQ ID NO:114,

BPTI (1Ala 13Phe 15Arg 17Tyr 19Thr 39Leu) SEQ ID NO:115,

BPTI (1Ala 13Ile 15Arg 17Tyr 19Thr 39Phe) SEQ ID NO:116,

BPTI (1Ala 13Ile 15Arg 17Phe 19Thr 39Leu) SEQ ID NO:117,

BPTI (1Ala 15Arg 17Tyr 19Thr 39Tyr) SEQ ID NO:118,

BPTI (1Ala 15Arg 17Tyr 19Thr 39Phe) SEQ ID NO:119,

BPTI (1Ala 13Ile 15Arg 17Tyr 19Lys 39Leu 46Glu) SEQ ID NO:120,

BPTI (1Ala 15Arg 17Tyr 19Thr 39Tyr 46Tyr) SEQ ID NO:121,

BPTI (13Ile 15Arg 17Ala 18Phe 19Asn 39Leu 46Glu) SEQ ID NO:122,

BPTI (13Ile 15Arg 17Ala 18Phe 19Lys 39Leu 46Glu) SEQ ID NO:123,

BPTI (13Ile 15Arg 17Ser 18Phe 19Lys 39Leu 46Glu) SEQ ID NO:124,

BPTI (13Ile 15Arg 17Tyr 18Tyr 19Lys 39Leu 46Glu) SEQ ID NO:125,

BPTI (13Ile 15Arg 17Ser 18Phe 19Thr 39Leu 46Glu) SEQ ID NO:126,

BPTI (11Pro 13Ile 15Arg 17Leu 18His 19Lys 34Tyr 39Met 46Glu) SEQ ID NO:127,

BPTI 11Glu 13Leu 15Arg 17Leu 18His 19Lys 34Tyr 39Phe 46Glu) SEQ ID NO:128,

BPTI(11Ser 13Leu 15Arg 17Leu 18His 19Lys 34Tyr 39Phe 46Glu) SEQ ID NO:129,

BPTI(11Ser 13Leu 15Arg 17Leu 18His 19Lys 34Tyr 39Tyr 46Glu) SEQ ID NO:130,

BPTI(11Glu 13Trp 15Arg 17Leu 18His 19His 34Ile 39Gly 46Glu) SEQ ID NO:131,

BPTI (11Glu 13Phe 15Arg 17His 18Phe 19Lys 32Ser 39Phe 46Glu) SEQ ID NO:132,

BPTI (11Glu 13Phe 15Arg 17Tyr 18Phe 19Lys 34Thr 39Phe 46Glu) SEQ ID NO:133,

BPTI (11Thr 13His 15Arg 17Tyr 18Phe 19Lys 34Ile 39Phe 46Glu) SEQ ID NO:134,

BPTI (10His 11Ser 13Ile 15Arg 17Tyr 18Phe 19Lys 39Phe 46Glu) SEQ ID NO:135,

BPTI (11Val 13Phe 15Arg 17Tyr 18Tyr 19Ile 39Phe 46Glu) SEQ ID NO:136.

Utility and Formulation

Blood coagulation is the culmination of a series of amplified reactions in which several specific zymogens of serine proteases are activated by limited proteolysis. The initiation and propagation of the activation reactions occurs through the extrinsic and intrinsic pathways of coagulation. Mackie, I. J. and Bull, H. A. (1989), "Normal Hemostasis and its Regulation", Blood Reviews, 3, 237–250. Both pathways are highly interdependent and converge in the formation of Factor Xa. Factor Xa catalyses the penultimate step in the blood coagulation cascade which is the formation of thrombin. Thrombin cleaves fibrinogen in the plasma resulting in clot formation.

By interfering at an early stage in the coagulation cascade, potent and selective Factor Xa inhibitors can be used as therapeutic agents for diseases associated with elevated Factor Xa activity, especially those diseases related to abnormal hemostasis. For example, Factor Xa inhibitors can be used to prevent reocclusion during thrombolytic therapy or angioplasty. They also can be used for the treatment of disseminated intravascular coagulopathy associated with septic shock, certain viral infections and cancer.

The specificity of the described inhibitors of Factor Xa is an important feature of these compounds with respect to their ability to control pathogenic thrombosis formation with minimal effects of the hemostatic potential of the treated patient. This will result in a reduction in the incidence of associated bleeding complications during therapy.

The present invention also encompasses pharmaceutical compositions prepared for storage and subsequent administration, which have a pharmaceutically effective amount of the compounds disclosed above in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A.R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also includes a method for preventing or treating a condition in mammals characterized by abnormal thrombosis. The pharmaceutically effective amount of the composition required as a dose will depend on the route of administration, the type of mammal being treated, and the physical characteristics of the specific mammal under consideration. The dose can be tailored to achieve optimal efficacy but will depend on such Factors as weight, diet, concurrent medication and other Factors which those skilled in the medical arts will recognize.

In practicing the methods of the invention, the compounds or compositions can be used alone or in combination with one another, or in combination with other therapeutic or diagnostic agents. These compounds can be utilized in vivo, ordinarily in a mammal, preferably in a human, or in vitro. In employing them in vivo, the compounds or compositions can be administered to the mammal in a variety of ways, including parenterally, intravenously, subcutaneously, intramuscularly, colonically, rectally, nasally or intraperitoneally, employing a variety of dosage forms.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, will be within the ambit of one skilled in the art. Typically, applications of compound are commenced at lower dosage levels, with dosage level being increased until the desired effect is achieved.

The dosage for the compounds of the present invention can range broadly depending upon the desired affects and the therapeutic indication. Typically, dosages will be between about 0.01 µg/kg and 100 mg/kg body weight, preferably between about 0.01 µg/kg and 10 mg/kg body weight. Administration is preferably parenteral, such as intravenous on a daily basis.

EXAMPLE 1

Construction of the Mc5-PI and pMa5-PI Vectors

A BPTI coding region was assembled making use of four chemically synthesized oligonucleotides (e.g., Pst205, a 74-mer; Pst206, a 78-mer; Pst207, a 102-mer and Pst208, a 102-mer; see FIG. 3). Following synthesis, the oligonucleotides were purified by preparative gel electrophoresis and enzymatically phosphorylated. Subsequently, the oligonucleotides were allowed to anneal pairwise: to this end, a 20 µl mixture containing 50 pmoles of each of the appropriate oligonucleotides was heated to 100° C. for 3 minutes, after which the mixture was allowed to cool to room temperature (about 20° C.). Annealing of the oligonucleotides Pst205 and Pst206 yields a blunt-ended/StyI fragment; similarly, the oligonucleotides Pst207 and Pst208 form a StyI/HindIII fragment. Together these fragments make up the entire double stranded BPTI coding region shown in FIG. 4B.

The recipient pMc5-19 was opened by KpnI restriction, treated with DNA polymerase I (Klenow fragment) to resect the 3'-overhanging ends, and subsequently digested with HindIII (FIG. 4A; other equivalent vectors can be readily designed and used by standard procedures). This material was ligated with the two above-mentioned BPTI-fragments. The lacI$^q$ strain WK6 was transformed with the ligation mixture. Based on a restriction analysis of 12 randomly picked Cm$^R$ transformants, five clones (designated c2, c8, c9, c10 and c11) were retained. Sequence determination of these clones confirmed the precise junction between the phoA signal and the BPTI coding region predicted by the construction scheme; all five clones were, however, found to contain one or more unwanted nucleotide substitutions. The clones c9 (contains a C->A substitution resulting in the Asn43Lys amino acid replacement) and c10 (the C->G results in a Leu to Val mutation) were used to construct a vector which encodes wild type BPTI; to this end the small EcoRI/StyI fragment of c9 and the small StyI/HindIII fragment of c10 were both purified from polyacrylamide gel and ligated to pMa5-8 digested with EcoRI and HindIII. One of the obtained clones displaying the correct restriction pattern was retained. This clone, which was shown to contain the intended BPTI coding region by sequence determination, was designated pMa5-PI. For mutation construction purposes we also constructed the complementary pMc5-PI. The latter vector was obtained by transferring the EcoRI/XbaI (an XbaI site is present immediately downstream of the HindIII site; see FIG. 4) expression cassette from pMa5-PI to pMc5-8.

Upon derepression of the $P_{tac}$ promoter, WK6 cells, harboring either pMa5-PI or pMc5-PI, were found to direct the synthesis of BPTI as shown by the appearance of trypsin inhibitory activity. This activity can be released with an osmotic shock, demonstrating that BPTI accumulates in the periplasmic space. The expression level is too low to visualize the protein by coomassie-staining following gel-electrophoretic fractionation of total cellular extracts. From the activity measurements it can be calculated that the BPTI protein amounts to about 1 mg per liter of culture ($OD_{600nm}$= ±4). The production level reported here is comparable to that found by others using similar expression systems (Marks et al., J. Biol. Chem. 261, 7115–7118, 1986; Goldenberg et al., Biochemistry 27, 2481–2489, 1988). Following purification (see below), the recombinant BPTI was subjected to N-terminal sequencing. The result indicates that the phoA-BPTI precursor undergoes correct processing.

EXAMPLE 2

Construction of the Genes Coding for BPTI-

Derived Molecules by Site Directed Mutagenesis Construction of 4c2

1. Preparation of single stranded DNA

An overnight culture of WK6 cells harboring the phasmid pMa5-PI (grown at 37° C. in LB-medium supplemented with 100 µg/ml ampicillin) was diluted 1:50 in fresh medium without antibiotic. Cells were grown to a density of about 2×10⁸/ml and infected with helper phage M13KO7 (Vieira, J. & Messing, J., Methods in Enzymology, 153, 3–11, 1987) at a multiplicity of infection of 20. After a 5–16 h incubation period, viral and pseudo-viral particles were recovered from the supernatant and the single stranded DNA extracted essentially as described (Sambrook, J., Fritsch, E. F. & Maniatis, T., in Molecular Cloning-a laboratory manual, Cold Spring Harbor Laboratory Press, 1989, p. 4.29). The yield (typically 1–4 µg/ml culture) was determined by UV-spectroscopy ($e_{260nm}$=2.86×10⁻² cm²/µg).

2. Preparation of DNA-fragment pMc5-PI plasmid DNA was digested to completion with the restriction enzymes SacII and SphI (both restriction sites are unique and are indicated in FIG. 4). The large fragment was recovered from low-melting-temperature agarose gel essentially as described (Weislander, L., Anal. Biochem., 98, 305–309, 1979). The yield of fragment was quantitated on an ethidium bromide stained agarose gel by comparison of the band intensity with known amounts of DNA.

3. Construction of gapped-duplex DNA (gdDNA)

The gdDNA is obtained by denaturation/renaturation of the large gel-purified SacII/SphI fragment from pMc5-PI and the single-stranded form of the complementary vector pMa5-PI. A 35 µl aqueous mixture (containing less than 2 mM salt) of fragment (0.1 pmole) and single stranded DNA (0.5 pmole) was incubated at 70° C. for 5 min; then 5 µl of 1.5M KCl/100 mM Tris-HCl pH 7.5, also brought to 70° C., was added, after which the mixture was allowed to cool to room temperature. Formation of gdDNA was monitored by electrophoresis of an aliquot of the hybridization mixture on agarose gel. The mobility of the gdDNA is indistinguishable from that of relaxed fully double stranded pMa/c5-PI.

4. Annealing of the mutagenic oligonucleotide and gap filling/sealing reaction.

The intended amino acid substitutions were introduced by means of three oligonucleotides: Pst210 for incorporation of Ile13, Arg15, Tyr17 and Thr19, Pst211 for Leu39, and Pst212 for Glu46. The sequence of the oligonucleotides is as follows (underlined residues differ from the wild type BPTI sequence):

Pst210:5'-GAAGTAGCGG GTAATATAAG CCCGGCA TAT GCCGGTATAC GG SEQ ID NO:137

Pst211:5'-GCTTTGCAAG GCAGCCACC SEQ ID NO:138

Pst212:5'-CCTCGGCCGA TTCGAAATTGT TAC SEQ ID NO:139

Note that some of the mutations directed by oligonucleotide Pst210 are associated with a restriction site; e.g. NdeI (recognition sequence CATATG) and NciI (CCCGG). Similarly, incorporation of oligonucleotide Pst212 results in the appearance of a BstBI site (TTCGAA).

The oligonucleotides were enzymatically phosphorylated and purified by preparative gel electrophoresis (Wu, R., Wu, N. -H., Hanna, Z., Georges, F. & Narang, S., in Oligonucleotide synthesis-a practical approach (Ed. Gait, M. J.), IRL Press, Oxford and Washington, D.C., pp.135–151, 1984).

Ten pmoles of each of the three oligonucleotides was added to 8 µl hybridisation mixture containing the gdDNA. This mixture was heated to 65° C. for 5 min and then allowed to cool to room temperature. Four µl 10x fill-in buffer (625 mM KCl, 275 mM Tris-HCl, 150 mM MgCl₂, 20 mM DTT, 0.5 mM ATP and 0.25 mM of each of the four dNTP's, pH7.5), water to give a final volume of 40 µl, 1 unit DNA polymerase I (Klenow fragment) and 5 units T4 DNA ligase were added. The mixture was incubated at room temperature for 45 min.

5. Transformation and segregation.

The polymerase/ligase reaction mixture (5 µl) was used to transform strain WK6mutS (Zell, R. & Fritz, H. -J., The EMBO Journal, 6, 1809–1815, 1987). An aliquot (1/10) of the transformation mixture was spread on selective medium (25 µg/ml chloramphenicol) to determine the transformation efficiency; about 250 transformants were obtained. The remainder of the transformation mixture was used to inoculate 10 ml of LB medium supplemented with 25 µg/ml chloramphenicol. After overnight growth, plasmid DNA was isolated and used to transform the su⁻ strain WK6 (Zell, R. & Fritz, H. -J., The EMBO Journal, 6, 1809–1815, 1987), again selecting for chloramphenicol resistance.

6. Identification of the intended mutant.

The plasmid DNA of eight randomly picked clones was prepared and analyzed for the presence of the NdeI site. Single stranded DNA (prepared as described in step 1) of one such NdeI⁺ clone was sequenced and found to incorporate all intended mutations. This clone was designated pMc5-PI4c2. Sequence determination of the entire mutant coding region was carried out according to the dideoxy chain termination method (Sanger, F., Nicklen, S. & Coulson, A. R., Proc. Natl. Acad. Sci. USA, 74, 5463–5467, 1977) using T7 DNA polymerase and a single primer which anneals to vector sequences immediately downstream of the mutant BPTI coding region (see FIG. 2).

Construction of 44c3

Mutant 44c3 carries the Thr11 to Glu amino acid substitution in addition to all the substitutions also present in 4c2. For the construction of 44c3, we used a gapped-duplex DNA molecule composed of a pMc5-PI4c2 single-stranded template and the large gel-purified SacII/SphI fragment from pMa5-PI. Glu11 was introduced with oligonucleotide Pst289 the sequence of which is as follows (underlined residues differ from the 4c2 template sequence):

Pst289: 5'-CCGGCATATG CCCTCATACG GTGGC SEQ ID NO:140

In this particular experiment, the WK6mutS and the WK6 transformants were selected on 100 µg/ml ampicillin.

Because the mutations directed by Pst289 eliminate the unique AccI restriction site (present in both the wild type BPTI and the 4c2 coding region; see FIG. 4), the plasmid DNA isolated from the WK6mutS transformants was digested with the AccI enzyme prior to the transformation of WK6 cells. Analysis of the plasmid DNA isolated from three WK6 transformants confirmed the loss of the AccI site; one clone, designated pMa5-PI44c3, was shown by sequence determination to contain the correct coding region.

EXAMPLE 3

Construction of 4c2 Secretion Vectors and Expression in the Methylotrophic Yeast *Pichia pastoris*

Alcohol oxidase, the first enzyme in the methanol utilization pathway of *Pichia pastoris*, can constitute as much as 30% of the soluble protein of the cell during growth on methanol. In contrast, when this yeast is grown in presence of an excess of repressible-carbon sources, such as glucose or glycerol, no alcohol oxidase is present. Several genes of the methanol utilization pathway have been cloned and characterized. Their methanol-inducible promoter regions have been sequenced and used to construct various expression vectors.

The Pichia strain GTS115 (his4) and the *E. coli-Pichia* shuttle vectors pHILS1 and pHILD4 referred to hereafter are part of the Pichia yeast expression system licensed from the Phillips Petroleum Company.

All the yeast manipulations, including electroporation, screening of multicopy integrants, determination of the methanol utilization (Mut) phenotype and fermentation, were performed according to the procedures manual provided by the Phillips Petroleum Company.

The pHILS1 plasmid contains the following *P. pastoris* elements:

1) 5' AOX1, about 1000 bp segment of the alcohol oxidase promoter fused to PHO1 signal peptide, with XhoI, EcoRI, SmaI and BamHI cloning sites.

2) 3' AOX1, about 256 bp segment of the alcohol oxidase terminating sequence.

3) *P. pastoris* histidinol dehydrogenase gene, HIS4, contained on a 2.4 kb fragment to complement the defective his4 gene in the host GTS115.

4) Region of 3' AOX1 DNA, which together with the 5' AOX1 region is necessary for site-directed integration.

In this vector, the ATG start codon of the PHO1 secretion signal is located downstream of the AOX1 promotor exactly at the same position as the ATG of the AOX1 gene.

The junction between the PHO1 signal sequence and the 5' AOX1 and 3' AOX1 sequences are as follows:

```
         5'  AOX1        PHO1 SIGNAL SEQUENCE                    XhoI
        TTA TTC GAA ACG/ATG TTC TCT ... SEQ ID NO: 141  GTC TTC GCT/CGA GAA TTC CCC
                        Met Phe Ser ... Val Phe Ala
            BamHI      3'   AOX1
        GGG ATC CTT/AGA CAT ... SEQ ID NO: 142
```

A BspmII-HindIII fragment containing the 4c2 encoding sequence starting at the second residue (proline) was extracted from the pMc5-PI 4c2 vector and, after filling in the cohesive ends with DNA polymerase I (Klenow fragment), inserted into XhoI-BamHI digested and blunt ended pHILS1 recipient vector. The Klenow treatment of the XhoI end of pHILS1 introduces an extra Arg codon, CGA, after the PHO1 signal peptide. This amino acid corresponds to the first amino acid of 4c2. On the other hand, the Klenow treatment of the BspmII end in the 4c2 *E. coli* constructs restores precisely the Pro2 codon at the 5' end. The ligation of both fragments allows a perfect fusion between the PHO1 signal (Phe-2, Ala-1) and the 4c2 gene (Arg+1, Pro+2, . . .). The ligated material was transformed in the *E. coli* host WK6. A vector harboring a correctly oriented insert was screened by restriction analysis and designated pHILS1-4c2.

The pHILS4-4c2 derivative was constructed by transferring part of the expression cassette containing the PHO1-4c2 encoding sequence, as a SacI-XbaI fragment, from pHILS1-4c2 to pHILD4. The latter vector contains, in addition to the other elements of pHILS1, a bacterial kanamycin resistance gene inserted between the HIS4 and 3' AOX1 regions. It can be used to screen for Pichia transformants with multiple copies of the expression cassette by screening for increased level of resistance to the antibiotic G418.

After transformation (spheroplast method) of pHILS4-4c2 in the Pichia strain GTS115, His+ transformants were tested for antibiotic G418 resistance on plates containing G418 at levels ranging from 100 ug/ml to 2000 ug/ml. Clones resistant to the higher level of G418 were then evaluated for 4c2 production in a shake-flask after induction of the Paox promoter with methanol, and were found to direct the synthesis and secretion of 4c2, as shown by the appearance of trypsin inhibitory activity in the culture medium.

The clone GTS115/4c2#25 (Mut+ phenotype) was run in a 10 L Biostat E fermentor in the batch-fed mode (biomass accumulation on glycerol to starvation, followed by induction on methanol as sole carbon and energy source). At the end of the fermentor run (about 130 hours) a biomass of about 440 WW g/l was accumulated. From the activity measurements, a production yield of 90 mg per liter of culture supernatant was calculated. Following purification, the recombinant 4c2 was subjected to N-terminal sequencing. The results indicate that the PHO1-4c2 precursor was correctly processed.

EXAMPLE 4

Purification of Recombinant BPTI-Derived Inhibitors from *E. coli*

*E. coli* cells were grown at 37° C. in baffled flasks in 250 ml LB medium containing chloramphenicol or ampicillin (as required by the type of vector involved, pMa5 requires ampicillin and pMc5 requires chloramphenicol). The cells were induced after 3 hours by addition of 0.1 mM IPTG and grown overnight. Lysis of *E. coli* cells was as described by Marks, C. B. et al., (1986) J. Biol. Chem. 261, 7115–7118. About 1 g of wet cells were suspended in 1.5 ml 40 mM TRIS buffer pH 8 containing 20% sucrose and 50 mM EDTA. 2.5 mg of lysozyme was added, followed by 1.15 ml of 0.1% Triton X-100 and 0.3 ml NaCl (5M). After 15 minutes at room temperature 2.5 ml of 200 mM TEA buffer pH 7.8 was added followed by 0.15 ml CaCl2 (1M) and 0.1 ml MgCl2 (1M) and 10 µg of DNAseI. The suspension was stirred for 20 minutes at 25° C. The majority of protein was precipitated by addition of 2% TCA and removed by centrifugation. The TCA supernatant was neutralized by addition of NaOH for further purification.

The purification consisted of the following steps:

1. Affinity chromatography on trypsin-Sepharose, equilibrated with 100 mM TEA pH 7.8, 300 mM NaCl, washed with 5 column volumes of 100 mM TEA pH 7.8, 300 mM NaCl, 10 mM TEA pH 7.8, 50 mM NaCl and eluted with 20 mM HCl, 50 mM NaCl pH 1.8.
2. Cation exchange chromatography on Mono-S using a linear gradient of 10 column volumes of 10–500 mM ammonium acetate pH 5.
3. Reverse phase chromatography on HPLC C4 column, elution with a 0–35% gradient of isopropanol in 0.1% TFA.
4. Lyophilisation.

EXAMPLE 5
Phage Panning Procedure

Mutant BPTI-phages were isolated by scraping about 500,000 colonies from plates infected with the phage, and resuspending them in LB-medium. This suspension was cleared twice by centrifugation and the phages were recovered from the supernatant by PEG precipitation. The phage pellet was resuspended in TBS (TRIS buffered saline pH 7.4). About $10^{10}$ infectious particles (1 ml) were incubated with 10 nM/100 nM Factor Xa during 1–2 hours in the presence of 1 mM $Ca^{2+}$. This mixture was then panned for at least 30 minutes on a non-neutralizing anti-Xa monoclonal antibody immobilized on Sepharose CL-4B (0.1 ml) (such antibodies can be obtained by standard procedures as described in Example 6 and in Hoad and Geczy, 136 J. Imm. Methods 269, 1991, hereby incorporated by reference herein). The gel was extensively washed (10×1 ml) with TBS/0.5% Tween 20 over a period of 60 minutes at room temperature. Bound phages were eluted by addition of 2×0.5 ml 0.1 M HCl-glycine pH 2. The eluate was removed and neutralized by addition of 1M TRIS (pH 8). Eluted phages were amplified by infecting strain WK6 and plating for tetracycline resistant colonies. Cwirla, S. E. et al. (1990), Proc. Natl. Acad. Sci. USA, 87: 6378–6382. Phages were recovered as described above and the panning/amplification process repeated two more times.

EXAMPLE 6
Identification and Purification of a Non-Neutralizing Monoclonal Antibody Against Factor Xa Preparation of hybridomas and identification of desired monoclonal antibodies is done using standard techniques as described for example in Harlow, E., and Lane D., "Antibodies: A Laboratory Manual" (Cold Spring Harbor Laboratory 1988). Female balb/c mice are immunized with purified human Factor Xa isolated from pooled human plasma. Complete Freund's adjuvant is used for primary immunization and incomplete Freund's adjuvant for booster immunization. Route of immunization is both intraperitoneal and subcutaneous. Three days prior to fusion mice receive an intravenous perfusion boost of purified Factor Xa in saline. Spleens are removed and spleen cells are fused to the SP2/0 myeloma following standard hybridoma methods.

The screening identifies hybridoma antibodies that react with Factor Xa antigen without inhibition of the enzymatic activity of Factor Xa.

Briefly, 96 well polyvinyl chloride microtiter plates are passively coated with affinity purified goat anti-mouse IgG (from commercial source, e.g., Sigma Chemical Company, St. Louis, Mo.). Antibody-coated plates are blocked with bovine albumin and culture supernatants (diluted at least 1:50) are bound to the plates. Plates are washed to remove unbound antibody and Factor Xa is added followed by incubation. Plates are washed to remove unbound Factor Xa. Negative controls include hybridoma culture supernatant from a cell line secreting irrelevant monoclonal antibody, sterile culture medium and buffer. Bound active Factor Xa can be detected by adding a solution of chromogenic substrate (see Example 7), incubation for 4 hours at room temperature and determining the absorbance at 405 nm using a microtiterplate reader.

Immunoglobulin IgG is purified from the ascites fluid of a mouse containing the mouse hybridoma cell line of interest using a Biorad Laboratories MAPS II system according to the manufacturer's instructions. The lack of inhibition of Factor Xa by the purified monoclonal antibody is confirmed using the chromogenic assay described in Example 7.

The monoclonal antibody is immobilized on CNBr-activated Sepharose CL4B (Pharmacia) according to the manufacturer's instructions.

EXAMPLE 7
Enzymatic Assays

Trypsin, Factor Xa, thrombin, Factor XIIa and plasmin amidolytic assays

The following assays are useful to determine useful inhibitors of the invention, namely those with a low Factor Xa $K_i$, and high relative $K_i$'s for other enzyme activities. Briefly, the following were added to a 96-well microtiter plate well (see Table below):

50 µl TBSA (100 mM TRIS pH 7.4, 140 mM NaCl, 0.1% BSA);

50 µl inhibitor (various concentrations as required, diluted in TESA);

50 µl protease (suitable concentration, diluted in TBSA)

The plate was incubated at room temperature for 30 minutes or for 2 hours (Factor Xa); and 50 µl chromogenic substrate was added (as required, diluted in water). The initial rate was measured at 405–650 nM during 10–30 minutes at room temperature.

| Protease Assayed | Assay Protease (nM) | Concentration of Substrate (mM) | Substrate Used |
| --- | --- | --- | --- |
| Factor XIIa | 1 | 0.2 | D-hexhydroTyrosine-Gly—Arg-pNA diacetate |
| Factor VIIa | 2.5 | 0.1 | D—Ile—Pro—Arg-pNA dihydrochloride |
| Factor Xa | 0.25–0.50 | 0.25 | N-α-Cbo—D—Arg—Gly—Arg-pNA dihydrochloride |

-continued

| Protease Assayed | Assay Protease (nM) | Concentration of Substrate (mM) | Substrate Used |
|---|---|---|---|
| thrombin | 1 | 0.06 | D—Phe—L-Pipecolyl-Arg-pNA dihydrochloride |
| plasmin | 1 | 0.50 | L-pyroglutamyl-Pro—Arg-pNA hydrochloride |
| activated Arg-protein C | 1 | 0.4 | γ-Cbo—D—Lys—Pro—pNA Diacetate |
| tissue plasminogen tyrosyl-activator acetate | 1 | 1 | O-(methylsulfonyl)-D-hexahydro-Gly—Arg-pNA |
| trypsin Glu— | 1 | 0.25 | N—Bz—Ile-(γ-OR)—Gly—Arg-pNA hydro chloride, wherein R=H (50%) and R=CH₃ (50%) |

"pNA" refers to para-nitrophenylanilide
"Cbo" refers to benzyloxycarbonyl
"Bz" refers to benzoyl To determine the inhibition constants, the initial rate ($v_i$) was measured at various inhibitor ([$I_t$]) and substrate concentrations, and the apparent inhibition constant ($K_i$) was determined by fitting the data obtained at each substrate concentration with the following equation:

$$v_i/v_o = \{([E_t]-[I_t]-K_i^*) + [([I_t]+K_i^*-[E_t])^2 + 4K_i^*[E_t]]^{1/2}\}/2[E_t]$$

where $v_o$ is the uninhibited initial rate and [$E_t$] is the total enzyme concentration. Extrapolation of $K_i^*$ values to zero substrate concentrations yields a value for the real inhibition constant.

Amidolytic assay for Factor VIIa

Equal volumes of Factor VIIa (10 nM in TBS containing 0.8% BSA and 20 mM CaCl₂) and tissue Factor (40 nM in TBS containing 0.03% Triton X-100) were combined and incubated for 30 minutes at room temperature. 100 μl of the VIIa/TF complex was mixed with 50 μl of inhibitor and incubated for 30 minutes. The reaction was started by addition of substrate, typically 0.4 mM of S-2288 (H-D-Ile-Pro-Arg-pNA), and the initial rate of product formation was determined. The inhibition constant ($K_i$) is determined from the following equation:

$$v_i/v_o = 1 + [I_t]/K_i$$

when the total inhibitor concentration ([$I_t$]) exceeds the total enzyme concentration. Typical inhibitor concentrations vary between 0.2 and 2 μM.

Amidolytic assay for activated protein C

Reconstituted lyophilized human normal plasma is used as a source of protein C. Protein C activating enzyme (Kabi) is added to diluted plasma to give a concentration of approximately 5 nM activated protein C. 50 μl of activated protein C solution is combined with 100 μl TESA or inhibitor diluted in TBSA and incubated for 30 minutes at 37° C. 50 μl of 2 mM S-2366 (<Glu-Pro-Arg-pNA) is added and the initial rate of product formation is measured at 405 nm in a microtiter plate reader. The inhibition constant is determined from the following equation:

$$v_i/v_o = 1 + [I_t]/K_i$$

when the total inhibitor concentration ([$I_t$]) exceeds the total enzyme concentration. Typical inhibitor concentrations vary between 0.5 and 5 μM.

EXAMPLE 8

Inhibition Constants for Selected Factor Xa Inhibitors

Several mutant BPTI Factor Xa inhibitors were made by site directed mutagenesis using a method as described in Example 2. These mutant BPTI Factor Xa inhibitors were produced in *E. coli* and purified as described in Example 4. The enzymatic methods described in Example 7 were used to determine their inhibition constant for several serine proteases, including Factor Xa. The inhibition constant for Factor Xa of a selection of inhibitors is given below.

| Name | Amino acid substitutions in BPTI | Ki (nM) |
|---|---|---|
| 4c2 | 1Ala 13Ile 15Arg 17Tyr 19Thr 39Leu 46Glu SEQ ID NO: 143 | 3 |
| 4c10 | 1Ala 13Ile 15Arg 17Tyr 19Thr 39Leu SEQ ID NO: 144 | 2 |
| 32c3 | 1Ala 15Arg 17Tyr 19Thr 39Leu 46Glu SEQ ID NO: 145 | 8 |
| 37c11 | 1Ala 13Ile 15Arg 17Tyr 19Thr 32Arg 39Leu 46Glu SEQ ID NO: 146 | 2 |
| 44c3 | 1Ala 11Glu 13Ile 15Arg 17Tyr 19Thr 39Leu 46Glu SEQ ID NO: 147 | 11 |
| 57c1 | 1Ala 13Ile 15Arg 19Thr 39Leu SEQ ID NO: 148 | 2 |
| 59c4 | 1Ala 13Phe 15Arg 17Tyr 19Thr 39Leu SEQ ID NO: 149 | 8 |
| 62c3 | 1Ala 13Ile 15Arg 17Tyr 19Thr 39Phe SEQ ID NO: 150 | 6 |
| 60c1 | 1Ala 13Ile 15Arg 17Phe 19Thr 39Leu SEQ ID NO: 151 | 8 |
| 52c19 | 1Ala 15Arg 17Tyr 19Thr 39Tyr SEQ ID NO: 152 | 8 |
| 54c3 | 1Ala 15Arg 17Tyr 19Thr 39Ile SEQ ID NO: 153 | 13 |
| 55c10 | 1Ala 15Arg 17Tyr 19Thr 39Trp SEQ ID NO: 154 | 14 |
| 56c1 | 1Ala 15Arg 17Tyr 19Thr 39Phe SEQ ID NO: 155 | 9 |
| 43c5 | 1Ala 13Ile 15Arg 17Tyr 19Lys 39Leu 46Glu SEQ ID NO: 156 | 1.6 |
| 88c1 | 1Ala 15Arg 17Tyr 19Thr 39Tyr 46Tyr SEQ ID NO: 157 | 5 |
| 3L55 | 13Ile 15Arg 17Ala 18Phe 19Asn 39Leu 46Glu SEQ ID NO: 158 | 5 |
| 3L39 | 13Ile 15Arg 17Ala 18Phe 19Lys 39Leu 46Glu SEQ ID NO: 159 | 5 |
| 3L41 | 13Ile 15Arg 17Ser 18Phe 19Lys 39Leu 46Glu SEQ ID NO: 160 | 6 |
| 3L60 | 13Ile 15Arg 17Tyr 18Tyr 19Lys 39Leu 46Glu SEQ ID NO: 161 | 4 |
| 3L44 | 13Ile 15Arg 17Ser 18Phe 19Thr 39Leu 46Glu SEQ ID NO: 162 | 4 |
| 5L69 | 11Pro 13Ile 15Arg 17Leu 18His 19Lys 34Tyr 39Met 46Glu SEQ ID NO: 163 | 5 |

-continued

| Name | Amino acid substitutions in BPTI | Ki (nM) |
|---|---|---|
| 5L84 | 11Glu 13Leu 15Arg 17Leu 18His 19Lys 34Tyr 39Phe 46Glu SEQ ID NO: 164 | 2 |
| 5L68 | 11Ser 13Leu 15Arg 17Leu 18His 19Lys 34Tyr 39Phe 46Glu SEQ ID NO: 165 | 1.5 |
| 5L65 | 11Ser 13Leu 15Arg 17Leu 18His 19Lys 34Tyr 39Tyr 46Glu SEQ ID NO: 166 | 5 |
| 5L48 | 11Glu 13Trp 15Arg 17Leu 18His 19His 34Ile 39Gly 46Glu SEQ ID NO: 167 | 4 |
| 7L60 | 11Glu 13Phe 15Arg 17His 18Phe 19Lys 32Ser 34Val 39Phe 46Glu SEQ ID NO: 168 | 8 |
| 7L22 | 11Glu 13Phe 15Arg 17Tyr 18Phe 19Lys 34Thr 39Phe 46Glu SEQ ID NO: 169 | 0.5 |
| 7L67 | 11Thr 13His 15Arg 17Tyr 18Phe 19Lys 34Ile 39Phe 46Glu SEQ ID NO: 170 | 5 |
| 7L71 | 10His 11Ser 13Ile 15Arg 17Tyr 18Phe 19Lys 34Val 39Phe 46Glu SEQ ID NO: 171 | 4 |
| 7L73 | 11Val 13Phe 15Arg 17Tyr 18Tyr 19Ile 34Val 39Phe 46Glu SEQ ID NO: 172 | 6 |

EXAMPLE 9
Selectivity of BPTI-Derived Factor Xa Inhibitors (pp4C2)

The specificity of the described inhibitors of Factor Xa is an important feature of these compounds with respect to their ability to control pathogenic thrombosis formation with minimal effects of the hemostatic potential of the treated patient. This will result in a reduction in the incidence of associated bleeding complications during therapy. The importance of specifically inhibiting Factor Xa versus thrombin as demonstrated in the compounds embodied in this application is obvious when one considers the amplified nature of the coagulation cascade where one molecule of Factor Xa can result in the generation of 200,000 thrombin molecules. Therefore, dosage of a selective Factor Xa inhibitor required to achieve a clinically relevant antithrombotic effect will be considerably less than a comparable thrombin inhibitor of equal potency or another inhibitor of Factor Xa which lacks this specificity. The specificity of the described Factor Xa inhibitors versus tPA is absolutely required if these compounds are to be used conjunctively with this thrombolytic agent in the reperfusion of infarct-related coronary vessels. Overall the more specific the inhibitor towards individual enzymes in the coagulation cascade the less probability exists that unwanted side effects will occur during therapy.

The Factor Xa inhibitor called pp4C2 contains the following substitutions in BPTI: 13Ile 15Arg 17Tyr 19Thr 39Leu 46Glu. Pp4C2 inhibits Factor Xa with an inhibition constant in the nanomolar range. It is a slow tight binding inhibitor of Factor Xa with quasi irreversible binding under physiological conditions.

Importantly, Factor XIIa and thrombin are not inhibited by pp4C2 at physiologically significant concentrations (up to 25 μM). Pp4C2 also does not inhibit the amidolytic activity of tPA or urokinase. Pp4C2 only very weakly inhibits activated protein C with an inhibition constant in the micromolar range. Since there is a 1000 fold difference in the concentrations required to inhibit Factor Xa and activated protein C it will be possible to adjust the administered dose so as to leave activated protein C unaffected. BPTI reportedly is a potent inhibitor of kallikrein. Compared to BPTI the affinity of pp4C2 for porcine pancreatic kallikrein is decreased about 100 fold.

Pp4C2 is, as BPTI, a potent trypsin inhibitor. This is not unexpected since trypsin is not a specific protease; its inhibition profile is largely determined by the P1 residue (Arg or Lys) with a great deal of variability tolerated in the surrounding residues.

Plasmin plays a crucial role during thrombolysis, since it degrades the fibrin clot. However plasmin is also believed to be responsible for bleeding problems often encountered during thrombolytic therapy. Bleeding can be reduced by administration of Aprotinin (BPTI) which is a very efficient plasmin inhibitor. Compared to BPTI the affinity of pp4C2 for plasmin is reduced about 100 fold. It remains however a potent plasmin inhibitor with an inhibition constant in the nanomolar range. Other BPTI mutants of this invention have substantially reduced plasmin activity while retaining potent Factor Xa inhibition.

EXAMPLE 10
Antithrombotic Effect of the Mutant BPTI Factor Xa Inhibitor 4c2 in vivo The effect of the Factor Xa inhibitor called pp4c2 on thrombus was determined using the method developed in rats by Stockmans et al. (1991), Thrombosis and Haemostasis 65, 425–431. In this experimental animal model, the thrombus is induced by a standardized crush injury of the femoral vein. The appearance and disappearance of the thrombus is monitored during 40 minutes after injury by means of a transilluminator combined with digital analysis of video recordings. Infusion of pp4c2 at 100 μg/kg/min during 30 minutes before the time of injury, caused about 80% inhibition of thrombus formation, compared with about 5% inhibition in control experiments wherein hamsters received an infusion of physiological saline solution. The results of this experiment are shown in FIG. 7.

EXAMPLE 11
Purification of the Factor Xa Inhibitor 4C10 from Pichia culture supernatant Pichia GTS115 cells were grown to starvation (max. 48 h) in 250 ml shake flask containing 50 ml medium (BMGY; 10.0 g/l yeast extract, 13.4 g/l yeast nitrogen base without amino acids, 20.0 g/l mycological peptone, 0.4 mg/l biotin, 13.61 g/l $KH_2PO_4$, 10.0 g/l glycerol). THe cells were harvested and resuspended in 10 ml of induction medium (BMMY; 10.0 g/l yeast extract, 13.4 g/l yeast nitrogen base without AA, 20.0 g/l mycoloogical peptone, 0.4 mg/l biotin, 13.61 g/l $KH_2PO_4$, 0.5% methanol. The cells were cultured during 3 days with a daily supply of methanol (0.5%). THe cells were removed by centrifugation and the supernatant was kept for further purification of the factor Xa inhibitor.

The 9 ml of supernatant was adjusted to pH 4.0 and to a conductivity below 5 mS/cm with respectively glacial acetic acid and MilliQ water. After filtration (0.2 μm pore size) the diluted supernatant was loaded on o S-Sepharose-FF cation exchange column (10×100 mm) at a flow rate of 1 ml/min. The column was eluted with a lineat 40 ml salt gradient (50 mM NaAc pH 4.0, 0–1M NaCl). The mutant BPTI 4c10 eluted at approximately 450 mM NaCl). The fractions were tested for factor Xa inhibition and the fraction containing most inhibitory activity was injected on an analytical RP C18 column (20 min gradient from 10% to 45% acetonitrile, 0.1% TFA, 1 ml/min). The mutant BPTI 4c10 appeared at the end of the gradient with a retention time of 16.43 minutes.

EXAMPLE 12
Measurement of Factor Xa Activity

The concentration of factor X in plasma is about 10μg/ml. Furie, B. and Furie, B., 53 Cell 505–518, 1988. In normal, healthy individuals the majority circulates as the zymogen, with very low levels of activated factor X (factor Xa) present. The total factor X concentration in plasma can be quantified by clotting tests such as the activated partial thromboplastin time (APTT) or the prothrombin time test (PT). ECAT Assay Procedures. A Manual of Laboratory Techniques. J. Jespersen, R. M. Bertino, F. Haverkate, eds., Kluwer Academic Publishers, Dorecht, The Netherlands, 1992. Specific chromogenic assays for factor X are also available (for example COATEST-X from Kabi). However, if it is necessary to differentiate between factor Xa and factor X, different assaus must be used. Monclonal antibodies which recognize factor X but not factor Xa, or factor Xa but not factor X have been described. Hoad and Geczy, 136 J. Immunological Methods 269–278, 1991. These could be used in an ELISA test to quantitate factor Xa in plasma. Other methods to evaluate increased activity of factor Xa measure the amount of reaction products formed by action of Factor Xa (e.g. thrombin, thrombin-antithrombin III complexes, prothrombin fragment 1+2) or reaction products of later steps in the coagulation cascade (e.g., D-dimer fibrin derivatives). Boneu et al., 65 Thrombosis and Haemostasis 28–32, 1991 Pelzer et al., 65 Thrombosis and Haemostasis 153–159. For example Baxter have developed and sell a Prothrombin Fragment F1.2 ELISA test. These tests can be performed on plasma samles. A probe that reacts specificall y with factor Xa (recombinant antistasin) has been described for use in immunohistochemical procedures to detect cellular sits of factor Xa generation in intact tissues. This can be used to detect abnormality increased factor Xa levels, for example, on tumor cells in biopsy samples. Since antistasin binds to the active site of Xa it can be concluded that the presence of Xa on such cells leads to abnormally high factor Xa acticity. Another method to monitor increased levels of factor Xa involves the quantification of the activation peptide which is released upon activation of the zymogen.

EXAMPLE 13
Construction of phage libraries

The following are examples of three different libraries of clones encoding factor Xa inhibitors. These libraries were constructed essentially as described above using mutagenic techniques.

(a) Construction of the 3L-library

This library contains a number of fixed amino acid substitutions in BPTI: Pro13Ile, Lys15Arg, Arg39Leu and Lys46Glu. In addition, at positions 16 to 19 all possible amino acid residues can occur. A new vector, pMa5-PI89, was constructed by oligonucleotide mediated mutagenesis of pMc5-PI4c2 using Pst344.

```
   BspMII              XhoI              BbsI                        (VI)
    |                   |                 |
    |       10          |     20          |    30             40
    |        *          |      *          |     *              *
   GCT CCG GAC TTC TGT CTC GAG CCA CCG TAT ACC GG  GTC TTC
   Ala Pro Asp Phe Cys Leu Glu Pro Pro Tyr Thr Gly                  SEQ ID NO: 175

FspI                                    BbsI
    |                                       |
    |       50                60           |    70             80
    |        *                 *           |     *              *
   TGC GCA TTT AAA TTA ACC GAA GAC AC  AAC GCC AAG GCC GGA
                                          Asn Ala Lys Ala Gly 90              100                110             120
            *               *                  *               *
   CTC TGT CAG ACC TTT GTA TAT GGT GGC TGC CTT GCA AAG CGT
   Leu Cys Gln Thr Phe Val Tyr Gly Gly Cys Leu Ala Lys Arg

EagI
                       |
          130          |  140              150             160
           *           |   *                *               *
   AAC AAT TTC GAA TCG GCC GAG GAC TGC ATG CGT ACC TGT GGT
   Asn Asn Phe Glu Ser Ala Glu Asp Cys Met Arg Thr Cys Gly

KasI
    |
    |      170
    |       *
   GGC GCC    SEQ ID NO: 174
   Gly Ala    SEQ ID NO: 176
```

Transfer of the BspMII-KasI fragment in this vector to the phage genome (engineered gene variant III as described on pages 13–14) resulted in fd-89. The sequence of VI does not code for a functional protein because of the presence of a frame shift. The sequence between nucleotides 35 and 65 provides restriction sites (BbsI) for easy insertion of the mutagenic oligonucleotides and counterselection against parental phages (FspI). Construction of the library involved the replacement of the small BbsI fragement of fd-89 by the mutagenic oligonucleotide Pst345. This cloning brings the two translated regions shown in (VI) in frame. The mutagenic oligonucleotide contains a degenerate coding sequence, where N is either of G, A, T and C and K is either G and T.

Pst345 was hybridized to two "half-site" oligonucleotides (Pst346 and Pst347 see below) to form cohesive termini complementary to the BbsI sites shown in (VI). Because cleavage of the two BbsI sites creates non-complementary cohesive ends insertion of the mutagenic fragment in the proper orientation is ensured. The conditions used to insert the mutagenic oligonucleotides were essentially as described by Cwirla et al., Proc. Natl. Acad. Sci. USA: 87, 6378–6382, 1990. The ligated DNA was transformed by electroporation into E. coli WK62 (a spontaneously arisen F⁻ derivative of WK6). Transformants were plated on LB agar containing tetracycline.

Pst345: TACCGGCATC TGCCGCNNKN NKNNKNN-KCG CTACTTCTAC SEQ ID NO:177
Pst346: GCGGCAGATG CC SEQ ID NO:178

Pst347: CGTTGTAGAA GTAGCG SEQ ID NO:179

(b) Construction of the 5L-library

The 5L library contained the following substitutions:

position 11: Xxx (=all possible residues)
- 13: Xxx
- 15: Arg
- 17: Leu/Ile
- 18: His
- 19: Lys/Asn/Thr/Met/Ile/Gln/His/Pro/Leu
- 34: Xxx
- 39: Xxx
- 46: Glu The mutagenic oligonucleotides, Pst374 and Pst375, contained degenerate sequences indicated with the following one letter code:

N is either of G, A, T and C

H is either of A, T and C

D is either of A, T and G

S is either of G and C

M is either of A and C

K is either of G and T

Pst374: TCGAGCCACC GTATNNSGGT NNSTGCCGTG CTMTTCATMH SCGCTACTTC TACAACGCCA AGGCCGGTCT CTGTCAGACC TTTNNSTATG GTGGCTGCNN SGCAAAGCGT AACAATTTCG AATC SEQ ID NO:180

Pst375: GGCCGATTCG AAATTGTTAC GCTTTGCSNN GCAGCCACCA TASNNAAAGG TCTGACAGAG ACCGGCCTTG GCGTTGTAGA AGTAGCGSDK ATGAAKAGCA CGGCASNNAC CSNNATACGG TGGC SEQ ID NO:181

Annealing of the oligonucleotides Pst374 and Pst375 yielded a double stranded DNA fragment having XhoI and EagI cohesive termini. This fragment was ligated to the large gel-purified XhoI-EagI fragment of fd-89 (VI). The ligated DNA was transformed by electroporation in *E. coli* WK62. Transformants were plated on LB agar containing tetracycline.

(c) Construction of the 7L-library

The 7L library contained the following substitutions:

position 11: Ala, Asp, Asn, Glu, Ile, Leu, Lys, Met, Phe, Ser, Thr, Tyr, and Val,
- 13: Ile, Phe, His, Leu, Asn, Pro, Ser, Thr, and Tyr
- 15: Arg
- 17: His, Phe, Leu, and Tyr
- 18: Asp, Phe, His, Ile, Leu, Asn, Tyr, and Val
- 19: Ile, Lys, Arg, Thr
- 34: Ala, Asn, Asp, Gln, Glu, His, Ile, Leu, Lys Phe, Pro, Ser, Thr, Tyr, Val
- 39: Leu and Phe
- 46: Glu The mutagenic oligonucleotides, Pst410 and Pst411, contained degenerate sequences indicated with the following one letter code:

N is either of G, A, T and C

H is either of A, T and C

D is either of A, T and G

S is either of G and C

M is either of A and C

Y is either of C and T

W is either of A and T

Pst410: TCGAGCCACC GTATDHSGGC HHCTGCCGTG CTYWCNWCAN ACGCTACTTC TACAACGCCA AGGCCGGACT CTGTCAGACC TTTNHMTATG GTGGCTGCTT SGCAAAGCGT AACAATTTCG AATC SEQ ID NO:182

Pst411: GGCCGATTCG AAATTGTTAC GCTTTGCSAA GCAGCCACCA TAKDNAAAGG TCTGACAGAG TCCGGCCTTG GCGTTGTAGA AGTAGCGTNT GWNGWRAGCA CGGCAGDDGC CSDHATACGG TGGC SEQ ID NO:183

Annealing of the mutagenic oligonucleotides yielded a double stranded DNA fragment having XhoI and EagI cohesive termini. This fragment was ligated to fd-89 which had been digested with XhoI and EagI (VI). The ligated DNA was digested with FspI to counterselect parental phages (VI), and subsequently transformed by electroporation in *E. coli* WK62. Transformants were plated on LB agar containing tetracycline.

EXAMPLE 14

Panning of phase libraries with biotinylated factor Xa.

In another preferred panning protocol the phages described in example 13 were incubated with biotinylated factor Xa. Phages bound to factor Xa were separated by binding of the biotinylated factor Xa to streptavidin-coated magnetizable beads (Dynal) and eluted at low pH.

Factor Xa was biotinylated using Biotine-XX-NHS essentially according to the instructions of the manufacturer (Calbiochem).

Mutant BPTI-phages were isolated by scraping the tetracycline resistant transformants from the plates described in example 13. The cell suspension (LB medium) was cleared twice by centrifugation and the phages recov- ered from the supernatant by PEG precipitation. The phage pellet was resuspended in TBS (20 mM Tris buffered saline, pH 7.4). About $5 \times 10^{10}$ infectious particles (1 ml) were incubated with 10 nM biotinylated factor Xa (0.5% Tween 20 in TBS). The suspension was incubated at room temperature (about 20°–25° C.) during 20 min–2 h. Streptavidin-coated magnetizable beads were added in excess over factor Xa and incubation continued for 5–30 min. The beads were removed and washed 10 times with 1 ml TBS containing 0.5% Tween 20 and 0.1% BSA. Bound phages (i.e., those exercising a potential factor Xa inhibitor which binds to factor Xa) were eluted with 0.1N HCl/glycine pH 2 containing 0.15M NaCl, 0.05% BSA, and 0.5% Tween 20. Eluted phages, neutralized by addition of 1M Tris (pH 8), were amplified by infecting strain WK6 and plating for tetracycline resistant colonies. Cwirla, S. E., et al., Proc. Natl. Acad. Sci. USA, 87: 6378–6382 (1990). Phages were recovered as described above and the panning-amplification process repeated with decreasing factor Xa concentrations (e.g., 1 nM in the second round, 0.1 nM in the third round and 0.01 nM in the fourth and fifth rounds). After the final binding-selection the phage DNA was purified and sequenced using standard techniques. Selected phage clones were tested for inhibition of factor Xa amidolytic activity.

The BPTI-mutant encoding region of isolated phage clones was transferred to the pMa5-PI or pMc5-PI vectors described above for expression of the encoded factor Xa inhibitor in soluble form (as opposed to phage-attached). The inhibition constants of selected inhibitors were determined using the amidolytic assay as described above. The panning procedure described above allowed identification of factor Xa inhibitors from the 3L, 5L and 7L libraries with Ki values below 10 nM.

Other embodiments are within the following claims.

---

SEQUENCE LISTING ( 1 ) GENERAL INFORMATION:

( i i i ) NUMBER OF SEQUENCES: 284

( 2 ) INFORMATION FOR SEQ ID NO: 1:

( i ) SEQUENCE CHARACTERISTICS:
        ( A ) LENGTH: 58
        ( B ) TYPE: amino acid
        ( C ) STRANDEDNESS: single
        ( D ) TOPOLOGY: linear ( x i ) SEQUENCE DESCRIPTION: SEQ ID NO: 1:

Arg Pro Asp Phe Cys Leu Glu Pro Pro Tyr Thr Gly Pro Cys Lys Ala
                      5                      10                  15

Arg Ile Ile Arg Tyr Phe Tyr Asn Ala Lys Ala Gly Leu Cys Gln Thr
            20                    25                    30

Phe Val Tyr Gly Gly Cys Arg Ala Lys Arg Asn Asn Phe Lys Ser Ala
        35                      40                      45

Glu Asp Cys Met Arg Thr Cys Gly Gly Ala
    50                      55

( 2 ) INFORMATION FOR SEQ ID NO: 2:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( x i ) SEQUENCE DESCRIPTION: SEQ ID NO: 2:

Gly Pro Cys Lys Ala Arg Ile Ile
              5

( 2 ) INFORMATION FOR SEQ ID NO: 3:

( i ) SEQUENCE CHARACTERISTICS:
        ( A ) LENGTH: 51
        ( B ) TYPE: amino acid
        ( C ) STRANDEDNESS: single
        ( D ) TOPOLOGY: linear ( i x ) FEATURE:
        ( D ) OTHER INFORMATION: Xaa in position 7 is alanine, arginine, asparagine, aspartic acid, glutamic acid, glutamine, isoleucine, leucine, lysine, proline, serine, threonine, tryptophan, tyrosine, or valine; Xaa in position 9 is alanine, asparagine, aspartic acid, glutamine, glycine, histidine, isoleucine, leucine, methionine, phenylalanine, proline, serine, threonine, tryptophan, tyrosine, or valine; Xaa in position 10 is alanine, serine or cysteine. When Xaa in position 10 is cysteine, Xaa in position 34 must be cysteine; Xaa in position 11 is arginine; Xaa in position 12 is alanine or glycine; Xaa in position 13 is alanine, asparagine, aspartic acid, glutamine, histidine, isoleucine, leucine, methionine, phenylalanine, proline, serine, threonine, tryptophan, tyrosine or valine; Xaa in position 14, Xaa in position 15 and Xaa in position 16 is any natural amino acid; Xaa in position 30 is alanine, arginine, asparagine, aspartic acid, cysteine, glutamic acid, glutamine, glycine, histidine, isoleucine, leucine, methionine, phenylalanine, proline, serine, threonine, tryptophan, tyrosine or valine; Xaa in position 31 is phenylalanine or tyrosine; Xaa in position 34 is alanine, serine or cysteine. When Xaa in posiiton 34 is cysteine, Xaa in position 10 must be cysteine; Xaa in position 35 is glutamine, glycine, histidine, isoleucine, leucine, lysine, methionine, phenylalanine, proline, serine, threonine, tryptophan, tyrosine or valine; Xaa in position 41 is phenylalanine or tyrosine; and Xaa in position 42 is any natural amino acid.

(xi) SEQUENCE DESCRIPTION: SEQ ID NO: 3:

| Cys | Leu | Glu | Pro | Pro | Tyr | Xaa | Gly | Xaa | Xaa | Xaa | Xaa | Xaa | Xaa | Xaa |
|---|---|---|---|---|---|---|---|---|---|---|---|---|---|---|
| 1 | | | | 5 | | | | | 10 | | | | | 15 |

| Xaa | Tyr | Phe | Tyr | Asn | Ala | Lys | Ala | Gly | Leu | Cys | Gln | Thr | Phe | Xaa | Xaa | Gly |
|---|---|---|---|---|---|---|---|---|---|---|---|---|---|---|---|---|
| | | | | 20 | | | | | 25 | | | | | 30 | | |

| Gly | Xaa | Xaa | Ala | Lys | Arg | Asn | Asn | Xaa | Xaa | Ser | Ala | Glu | Asp | Cys | Met |
|---|---|---|---|---|---|---|---|---|---|---|---|---|---|---|---|
| | | 35 | | | | | 40 | | | | | 45 | | | |

Arg Thr Cys
        50

(2) INFORMATION FOR SEQ ID NO: 4:

(i) SEQUENCE CHARACTERISTICS:
    (A) LENGTH: 58
    (B) TYPE: amino acid
    (C) STRANDEDNESS: single
    (D) TOPOLOGY: linear (ix) FEATURE:
    (D) OTHER INFORMATION: Xaa in position 1 is alanine or arginine; Xaa in position 11 is alanine, arginine, aspartic acid, glutamic acid, glutamine, leucine, proline, serine, threonine or valine; Xaa in position 13 is asparagine, aspartic acid, histidine, isoleucine, leucine, methionine, phenylalanine, proline, tryptophan, tyrosine, or valine; Xaa in position 14 is cysteine; Xaa in position 15 is arginine; Xaa in position 16 is alanine or glycine; Xaa in position 17 is alanine, asparagine, histidine, isoleucine, leucine, methionine, phenylalanine, serine, tryptophan or tyrosine; Xaa in position 18 is asparagine, histidine, isoleucine, leucine, phenylalanine, tyrosine or valine; Xaa in position 19 is arginine, asparagine, glutamine, histidine, isoleucine, leucine, lysine, proline, threonine or valine, Xaa in position 20 is arginine, histidine, glutamic acid, glutamine, leucine, threonine or valine; Xaa in position 34 is alanine, glutamic acid, histidine, isoleucine, leucine, methionine, phenylalanine, serine, threonine, tryptophan, tyrosine or valine; Xaa in position 35 is phenylalanine or tyrosine; Xaa in position 38 is cysteine; Xaa in position 39 is glutamine, glycine, histidine, isoleucine, leucine, methionine, phenylalanine, serine, tryptophan, tyrosine or valine; Xaa in position 45 is phenylalanine; and Xaa in position 46 is glutamic acid, lysine or tyrosine.

(xi) SEQUENCE DESCRIPTION: SEQ ID NO: 4:

| Xaa | Pro | Asp | Phe | Cys | Leu | Glu | Pro | Pro | Tyr | Xaa | Gly | Xaa | Xaa | Xaa | Xaa |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Xaa | Xaa | Xaa | Xaa | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
|     |     | 20  |     |     |     |     |     | 25  |     |     |     |     | 30  |     |     |

| Phe | Xaa | Xaa | Gly | Gly | Xaa | Xaa | Ala | Lys | Arg | Asn | Asn | Xaa | Xaa | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Asp | Cys | Met | Arg | Thr | Cys | Gly | Gly | Ala |
|-----|-----|-----|-----|-----|-----|-----|-----|-----|-----|
|     | 50  |     |     |     |     | 55  |     |     |     |

(2) INFORMATION FOR SEQ ID NO: 5:

(i) SEQUENCE CHARACTERISTICS:
      (A) LENGTH: 36
      (B) TYPE: nucleic acid
      (C) STRANDEDNESS: single
      (D) TOPOLOGY: linear (xi) SEQUENCE DESCRIPTION: SEQ ID NO: 5:

CACTCCGCTC CGGACACTAG TGGTGGCGCC GCTGAA                                  36

(2) INFORMATION FOR SEQ ID NO: 6:

(i) SEQUENCE CHARACTERISTICS:
      (A) LENGTH: 24
      (B) TYPE: nucleic acid
      (C) STRANDEDNESS: single
      (D) TOPOLOGY: linear (xi) SEQUENCE DESCRIPTION: SEQ ID NO: 6:

GTTACGCTTT GCCCTGCAGC CACC                                              24

(2) INFORMATION FOR SEQ ID NO: 7:

(i) SEQUENCE CHARACTERISTICS:
      (A) LENGTH: 27
      (B) TYPE: nucleic acid
      (C) STRANDEDNESS: single
      (D) TOPOLOGY: linear (xi) SEQUENCE DESCRIPTION: SEQ ID NO: 7:

GCCTTGCAGG GGCCCGGTAT ACGGTGG                                           27

(2) INFORMATION FOR SEQ ID NO: 8:

(i) SEQUENCE CHARACTERISTICS:
      (A) LENGTH: 63
      (B) TYPE: nucleic acid
      (C) STRANDEDNESS: single
      (D) TOPOLOGY: linear (ix) FEATURE: R is an equimolar mixture of A and G; N
       is either of G, A, T and C; and K is
       either of G or T.

(xi) SEQUENCE DESCRIPTION: SEQ ID NO: 8:

TATACCGGGC CCTGCARGNN KNNKNNKNNK NNKTACTTCT ACAACGCCAA GGCCGGACTC       60

TGT                                                                     63

(2) INFORMATION FOR SEQ ID NO: 9:

( i ) SEQUENCE CHARACTERISTICS:
  ( A ) LENGTH: 63
  ( B ) TYPE: nucleic acid
  ( C ) STRANDEDNESS: single
  ( D ) TOPOLOGY: linear ( x i ) SEQUENCE DESCRIPTION: SEQ ID NO: 9:

```
CTTTGCCCTG CAGCCACCAT ATACAAAGGT CTGACAGAGT CCGGCCTTGG CGTTGTAGAA    60
GTA                                                                 63
```

( 2 ) INFORMATION FOR SEQ ID NO: 10:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 10:

```
Arg Pro Asp Phe Cys Leu Glu Pro Pro Tyr Thr Gly Ile Cys Arg Ala
1               5                   10                  15
Tyr Ile Thr Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 11:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 11:

```
Ala Pro Asp Phe Cys Leu Glu Pro Pro Tyr Thr Gly Ile Cys Arg Ala
1               5                   10                  15
Tyr Ile Thr Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 12:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 12:

```
Ala Pro Asp Phe Cys Leu Glu Pro Pro Tyr Thr Gly Ile Cys Arg Ala
1               5                   10                  15
Tyr Ile Thr Arg Tyr Phe Tyr Asn Ala Lys Ala Gly Leu Cys Gln Thr
            20                  25                  30
```

Phe Val Tyr Gly Gly Cys Leu Ala Lys Arg Asn Asn Phe Lys Ser Ala
          35                    40                      45

Glu Asp Cys Met Arg Thr Cys Gly Gly Ala
        50                  55

( 2 ) INFORMATION FOR SEQ ID NO: 13:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 13:

Ala Pro Asp Phe Cys Leu Glu Pro Pro Tyr Thr Gly Pro Cys Arg Ala
1                5                   10                    15

Tyr Ile Thr Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
          35                    40                      45

Glu Asp Cys Met Arg Thr Cys Gly Gly Ala
        50                  55

( 2 ) INFORMATION FOR SEQ ID NO: 14:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 14:

Ala Pro Asp Phe Cys Leu Glu Pro Pro Tyr Thr Gly Ile Cys Arg Ala
1                5                   10                    15

Tyr Ile Thr Arg Tyr Phe Tyr Asn Ala Lys Ala Gly Leu Cys Gln Arg
            20                  25                  30

Phe Val Tyr Gly Gly Cys Leu Ala Lys Arg Asn Asn Phe Glu Ser Ala
          35                    40                      45

Glu Asp Cys Met Arg Thr Cys Gly Gly Ala
        50                  55

( 2 ) INFORMATION FOR SEQ ID NO: 15:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 15:

Ala Pro Asp Phe Cys Leu Glu Pro Pro Tyr Glu Gly Ile Cys Arg Ala
1                5                   10                    15

Tyr Ile Thr Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
          35                    40                      45

Glu Asp Cys Met Arg Thr Cys Gly Gly Ala 50          55

( 2 ) INFORMATION FOR SEQ ID NO: 16:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 16:

```
Ala Pro Asp Phe Cys Leu Glu Pro Pro Tyr Thr Gly Ile Cys Arg Ala
 1               5                  10                 15

Tyr Ile Ile Arg Tyr Phe Tyr Asn Ala Lys Ala Gly Leu Cys Gln Thr
             20                 25                 30

Phe Val Tyr Gly Gly Cys Leu Ala Lys Arg Asn Asn Phe Lys Ser Ala
         35                 40                 45

Glu Asp Cys Met Arg Thr Cys Gly Gly Ala
         50                 55
```

( 2 ) INFORMATION FOR SEQ ID NO: 17:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 17:

```
Ala Pro Asp Phe Cys Leu Glu Pro Pro Tyr Thr Gly Phe Cys Arg Ala
 1               5                  10                 15

Tyr Ile Thr Arg Tyr Phe Tyr Asn Ala Lys Ala Gly Leu Cys Gln Thr
             20                 25                 30

Phe Val Tyr Gly Gly Cys Leu Ala Lys Arg Asn Asn Phe Lys Ser Ala
         35                 40                 45

Glu Asp Cys Met Arg Thr Cys Gly Gly Ala
         50                 55
```

( 2 ) INFORMATION FOR SEQ ID NO: 18:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 18:

```
Ala Pro Asp Phe Cys Leu Glu Pro Pro Tyr Thr Gly Ile Cys Arg Ala
 1               5                  10                 15

Tyr Ile Thr Arg Tyr Phe Tyr Asn Ala Lys Ala Gly Leu Cys Gln Thr
             20                 25                 30

Phe Val Tyr Gly Gly Cys Phe Ala Lys Arg Asn Asn Phe Lys Ser Ala
         35                 40                 45

Glu Asp Cys Met Arg Thr Cys Gly Gly Ala
         50                 55
```

( 2 ) INFORMATION FOR SEQ ID NO: 19:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 19:

```
Ala  Pro  Asp  Phe  Cys  Leu  Glu  Pro  Pro  Tyr  Thr  Gly  Ile  Cys  Arg  Ala
 1                  5                        10                            15

Phe  Ile  Thr  Arg  Tyr  Phe  Tyr  Asn  Ala  Lys  Ala  Gly  Leu  Cys  Gln  Thr
               20                        25                       30

Phe  Val  Tyr  Gly  Gly  Cys  Leu  Ala  Lys  Arg  Asn  Asn  Phe  Lys  Ser  Ala
               35                   40                        45

Glu  Asp  Cys  Met  Arg  Thr  Cys  Gly  Gly  Ala
     50                        55
```

( 2 ) INFORMATION FOR SEQ ID NO: 20:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 20:

```
Ala  Pro  Asp  Phe  Cys  Leu  Glu  Pro  Pro  Tyr  Thr  Gly  Pro  Cys  Arg  Ala
 1                  5                        10                            15

Tyr  Ile  Thr  Arg  Tyr  Phe  Tyr  Asn  Ala  Lys  Ala  Gly  Leu  Cys  Gln  Thr
               20                        25                       30

Phe  Val  Tyr  Gly  Gly  Cys  Tyr  Ala  Lys  Arg  Asn  Asn  Phe  Lys  Ser  Ala
               35                   40                        45

Glu  Asp  Cys  Met  Arg  Thr  Cys  Gly  Gly  Ala
     50                        55
```

( 2 ) INFORMATION FOR SEQ ID NO: 21:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 21:

```
Ala  Pro  Asp  Phe  Cys  Leu  Glu  Pro  Pro  Tyr  Thr  Gly  Pro  Cys  Arg  Ala
 1                  5                        10                            15

Tyr  Ile  Thr  Arg  Tyr  Phe  Tyr  Asn  Ala  Lys  Ala  Gly  Leu  Cys  Gln  Thr
               20                        25                       30

Phe  Val  Tyr  Gly  Gly  Cys  Ile  Ala  Lys  Arg  Asn  Asn  Phe  Lys  Ser  Ala
               35                   40                        45

Glu  Asp  Cys  Met  Arg  Thr  Cys  Gly  Gly  Ala
     50                        55
```

( 2 ) INFORMATION FOR SEQ ID NO: 22:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear (ii) MOLECULE TYPE: peptide (xi) SEQUENCE DESCRIPTION: SEQ ID NO: 22:

| Ala | Pro | Asp | Phe | Cys | Leu | Glu | Pro | Pro | Tyr | Thr | Gly | Pro | Cys | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Tyr | Ile | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Trp | Ala | Lys | Arg | Asn | Asn | Phe | Lys | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 23:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 23:

| Ala | Pro | Asp | Phe | Cys | Leu | Glu | Pro | Pro | Tyr | Thr | Gly | Pro | Cys | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Tyr | Ile | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Phe | Ala | Lys | Arg | Asn | Asn | Phe | Lys | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 24:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 24:

| Ala | Pro | Asp | Phe | Cys | Leu | Glu | Pro | Pro | Tyr | Thr | Gly | Pro | Cys | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Tyr | Ile | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | His | Ala | Lys | Arg | Asn | Asn | Phe | Lys | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 25:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 25:

```
Ala  Pro  Asp  Phe  Cys  Leu  Glu  Pro  Pro  Tyr  Thr  Gly  Pro  Cys  Arg  Ala
1                    5                        10                       15

Tyr  Ile  Thr  Arg  Tyr  Phe  Tyr  Asn  Ala  Lys  Ala  Gly  Leu  Cys  Gln  Thr
               20                        25                       30

Phe  Val  Tyr  Gly  Gly  Cys  Ser  Ala  Lys  Arg  Asn  Asn  Phe  Lys  Ser  Ala
               35                  40                       45

Glu  Asp  Cys  Met  Arg  Thr  Cys  Gly  Gly  Ala
          50                  55
```

( 2 ) INFORMATION FOR SEQ ID NO: 26:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 26:

```
Ala  Pro  Asp  Phe  Cys  Leu  Glu  Pro  Pro  Tyr  Thr  Gly  Pro  Cys  Arg  Ala
1                    5                        10                       15

Tyr  Ile  Thr  Arg  Tyr  Phe  Tyr  Asn  Ala  Lys  Ala  Gly  Leu  Cys  Gln  Thr
               20                        25                       30

Phe  Val  Tyr  Gly  Gly  Cys  Val  Ala  Lys  Arg  Asn  Asn  Phe  Lys  Ser  Ala
               35                  40                       45

Glu  Asp  Cys  Met  Arg  Thr  Cys  Gly  Gly  Ala
          50                  55
```

( 2 ) INFORMATION FOR SEQ ID NO: 27:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 27:

```
Arg  Pro  Asp  Phe  Cys  Leu  Glu  Pro  Pro  Tyr  Thr  Gly  Pro  Cys  Arg  Gly
1                    5                        10                       15

Trp  Phe  Arg  Gln  Tyr  Phe  Tyr  Asn  Ala  Lys  Ala  Gly  Leu  Cys  Gln  Thr
               20                        25                       30

Phe  Val  Tyr  Gly  Gly  Cys  Arg  Ala  Lys  Arg  Asn  Asn  Phe  Lys  Ser  Ala
               35                  40                       45

Glu  Asp  Cys  Met  Arg  Thr  Cys  Gly  Gly  Ala
          50                  55
```

( 2 ) INFORMATION FOR SEQ ID NO: 28:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 28:

```
Arg  Pro  Asp  Phe  Cys  Leu  Glu  Pro  Pro  Tyr  Thr  Gly  Ile  Cys  Arg  Gly
1                    5                        10                       15

Trp  Phe  Arg  Gln  Tyr  Phe  Tyr  Asn  Ala  Lys  Ala  Gly  Leu  Cys  Gln  Thr
               20                        25                       30
```

```
Phe Val Tyr Gly Gly Cys Leu Ala Lys Arg Asn Asn Phe Lys Ser Ala
        35                  40                  45

Glu Asp Cys Met Arg Thr Cys Gly Gly Ala
    50                  55
```

( 2 ) INFORMATION FOR SEQ ID NO: 29:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 29:

```
Arg Pro Asp Phe Cys Leu Glu Pro Pro Tyr Glu Gly Ile Cys Arg Gly
1                5                   10                  15

Trp Phe Arg Gln Tyr Phe Tyr Asn Ala Lys Ala Gly Leu Cys Gln Thr
            20                  25                  30

Phe Val Tyr Gly Gly Cys Leu Ala Lys Arg Asn Asn Phe Lys Ser Ala
        35                  40                  45

Glu Asp Cys Met Arg Thr Cys Gly Gly Ala
    50                  55
```

( 2 ) INFORMATION FOR SEQ ID NO: 30:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 30:

```
Arg Pro Asp Phe Cys Leu Glu Pro Pro Tyr Thr Gly Pro Cys Arg Ala
1                5                   10                  15

His Ile Thr Thr Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55
```

( 2 ) INFORMATION FOR SEQ ID NO: 31:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 31:

```
Arg Pro Asp Phe Cys Leu Glu Pro Pro Tyr Thr Gly Ile Cys Arg Ala
1                5                   10                  15

His Ile Thr Thr Tyr Phe Tyr Asn Ala Lys Ala Gly Leu Cys Gln Thr
            20                  25                  30

Phe Val Tyr Gly Gly Cys Leu Ala Lys Arg Asn Asn Phe Lys Ser Ala
        35                  40                  45

Glu Asp Cys Met Arg Thr Cys Gly Gly Ala
```

( 2 ) INFORMATION FOR SEQ ID NO: 32:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 32:

```
Arg Pro Asp Phe Cys Leu Glu Pro Pro Tyr Glu Gly Ile Cys Arg Ala
 1               5                  10                  15

His Ile Thr Thr Tyr Phe Tyr Asn Ala Lys Ala Gly Leu Cys Gln Thr
                 20                  25                  30

Phe Val Tyr Gly Gly Cys Leu Ala Lys Arg Asn Asn Phe Lys Ser Ala
             35                  40                  45

Glu Asp Cys Met Arg Thr Cys Gly Gly Ala
         50                  55
```

( 2 ) INFORMATION FOR SEQ ID NO: 33:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 33:

```
Arg Pro Asp Phe Cys Leu Glu Pro Pro Tyr Thr Gly Pro Cys Arg Ala
 1               5                  10                  15

His His Leu Val Tyr Phe Tyr Asn Ala Lys Ala Gly Leu Cys Gln Thr
                 20                  25                  30

Phe Val Tyr Gly Gly Cys Arg Ala Lys Arg Asn Asn Phe Lys Ser Ala
             35                  40                  45

Glu Asp Cys Met Arg Thr Cys Gly Gly Ala
         50                  55
```

( 2 ) INFORMATION FOR SEQ ID NO: 34:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 34:

```
Arg Pro Asp Phe Cys Leu Glu Pro Pro Tyr Thr Gly Ile Cys Arg Ala
 1               5                  10                  15

His His Leu Val Tyr Phe Tyr Asn Ala Lys Ala Gly Leu Cys Gln Thr
                 20                  25                  30

Phe Val Tyr Gly Gly Cys Leu Ala Lys Arg Asn Asn Phe Lys Ser Ala
             35                  40                  45

Glu Asp Cys Met Arg Thr Cys Gly Gly Ala
         50                  55
```

( 2 ) INFORMATION FOR SEQ ID NO: 35:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 35:

```
Arg Pro Asp Phe Cys Leu Glu Pro Pro Tyr Glu Gly Ile Cys Arg Ala
1               5                   10                  15
His His Leu Val Tyr Phe Tyr Asn Ala Lys Ala Gly Leu Cys Gln Thr
            20                  25                  30
Phe Val Tyr Gly Gly Cys Leu Ala Lys Arg Asn Asn Phe Lys Ser Ala
        35                  40                  45
Glu Asp Cys Met Arg Thr Cys Gly Gly Ala
    50                  55
```

( 2 ) INFORMATION FOR SEQ ID NO: 36:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 36:

```
Arg Pro Asp Phe Cys Leu Glu Pro Pro Tyr Thr Gly Pro Cys Arg Ala
1               5                   10                  15
His His Arg Glu Tyr Phe Tyr Asn Ala Lys Ala Gly Leu Cys Gln Thr
            20                  25                  30
Phe Val Tyr Gly Gly Cys Arg Ala Lys Arg Asn Asn Phe Lys Ser Ala
        35                  40                  45
Glu Asp Cys Met Arg Thr Cys Gly Gly Ala
    50                  55
```

( 2 ) INFORMATION FOR SEQ ID NO: 37:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 37:

```
Arg Pro Asp Phe Cys Leu Glu Pro Pro Tyr Thr Gly Ile Cys Arg Ala
1               5                   10                  15
His His Arg Glu Tyr Phe Tyr Asn Ala Lys Ala Gly Leu Cys Gln Thr
            20                  25                  30
Phe Val Tyr Gly Gly Cys Leu Ala Lys Arg Asn Asn Phe Lys Ser Ala
        35                  40                  45
Glu Asp Cys Met Arg Thr Cys Gly Gly Ala
    50                  55
```

( 2 ) INFORMATION FOR SEQ ID NO: 38:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 38:

| Arg | Pro | Asp | Phe | Cys | Leu | Glu | Pro | Pro | Tyr | Glu | Gly | Ile | Cys | Arg | Ala |
|---|---|---|---|---|---|---|---|---|---|---|---|---|---|---|---|
| 1 | | | | 5 | | | | | 10 | | | | | 15 | |

| His | His | Arg | Glu | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Leu | Ala | Lys | Arg | Asn | Asn | Phe | Lys | Ser | Ala |
|---|---|---|---|---|---|---|---|---|---|---|---|---|---|---|---|
| | | 35 | | | | 40 | | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO: 39:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 39:

| Arg | Pro | Asp | Phe | Cys | Leu | Glu | Pro | Pro | Tyr | Thr | Gly | Pro | Cys | Arg | Ala |
|---|---|---|---|---|---|---|---|---|---|---|---|---|---|---|---|
| 1 | | | | 5 | | | | | 10 | | | | | 15 | |

| His | Ile | Arg | Gln | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Arg | Ala | Lys | Arg | Asn | Asn | Phe | Lys | Ser | Ala |
|---|---|---|---|---|---|---|---|---|---|---|---|---|---|---|---|
| | | 35 | | | | 40 | | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO: 40:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 40:

| Arg | Pro | Asp | Phe | Cys | Leu | Glu | Pro | Pro | Tyr | Thr | Gly | Ile | Cys | Arg | Ala |
|---|---|---|---|---|---|---|---|---|---|---|---|---|---|---|---|
| 1 | | | | 5 | | | | | 10 | | | | | 15 | |

| His | Ile | Arg | Gln | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Leu | Ala | Lys | Arg | Asn | Asn | Phe | Lys | Ser | Ala |
|---|---|---|---|---|---|---|---|---|---|---|---|---|---|---|---|
| | | 35 | | | | 40 | | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO: 41:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 41:

```
Arg Pro Asp Phe Cys Leu Glu Pro Pro Tyr Glu Gly Ile Cys Arg Ala
 1               5                  10                  15
His Ile Arg Gln Tyr Phe Tyr Asn Ala Lys Ala Gly Leu Cys Gln Thr
             20                  25                  30
Phe Val Tyr Gly Gly Cys Leu Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 42:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 42:

```
Arg Pro Asp Phe Cys Leu Glu Pro Pro Tyr Thr Gly Pro Cys Arg Gly
 1               5                  10                  15
His His Arg Glu Tyr Phe Tyr Asn Ala Asn Ala Gly Leu Cys Gln Thr
             20                  25                  30
Phe Val Tyr Gly Gly Cys Arg Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 43:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 43:

```
Arg Pro Asp Phe Cys Leu Glu Pro Pro Tyr Thr Gly Ile Cys Arg Gly
 1               5                  10                  15
His His Arg Glu Tyr Phe Tyr Asn Ala Asn Ala Gly Leu Cys Gln Thr
             20                  25                  30
Phe Val Tyr Gly Gly Cys Leu Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 44:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 44:

```
Arg Pro Asp Phe Cys Leu Glu Pro Pro Tyr Glu Gly Ile Cys Arg Gly
 1               5                  10                  15
His His Arg Glu Tyr Phe Tyr Asn Ala Asn Ala Gly Leu Cys Gln Thr
             20                  25                  30
```

Phe Val Tyr Gly Gly Cys Leu Ala Lys Arg Asn Asn Phe Lys Ser Ala
    35                      40                  45

Glu Asp Cys Met Arg Thr Cys Gly Gly Ala
    50                  55

( 2 ) INFORMATION FOR SEQ ID NO: 45:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 45:

Arg Pro Asp Phe Cys Leu Glu Pro Pro Tyr Thr Gly Pro Cys Arg Ala
1               5                   10                  15

Tyr Phe Asn Leu Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
    35                      40                  45

Glu Asp Cys Met Arg Thr Cys Gly Gly Ala
    50                  55

( 2 ) INFORMATION FOR SEQ ID NO: 46:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 46:

Arg Pro Asp Phe Cys Leu Glu Pro Pro Tyr Thr Gly Ile Cys Arg Ala
1               5                   10                  15

Tyr Phe Asn Leu Tyr Phe Tyr Asn Ala Lys Ala Gly Leu Cys Gln Thr
            20                  25                  30

Phe Val Tyr Gly Gly Cys Leu Ala Lys Arg Asn Asn Phe Lys Ser Ala
    35                      40                  45

Glu Asp Cys Met Arg Thr Cys Gly Gly Ala
    50                  55

( 2 ) INFORMATION FOR SEQ ID NO: 47:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 47:

Arg Pro Asp Phe Cys Leu Glu Pro Pro Tyr Glu Gly Ile Cys Arg Ala
1               5                   10                  15

Tyr Phe Asn Leu Tyr Phe Tyr Asn Ala Lys Ala Gly Leu Cys Gln Thr
            20                  25                  30

Phe Val Tyr Gly Gly Cys Leu Ala Lys Arg Asn Asn Phe Lys Ser Ala
    35                      40                  45

Glu Asp Cys Met Arg Thr Cys Gly Gly Ala ( 2 ) INFORMATION FOR SEQ ID NO: 48:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 48:

```
Arg Pro Asp Phe Cys Leu Glu Pro Pro Tyr Thr Gly Pro Cys Arg Ala
 1               5                  10                 15
His Val Arg His Tyr Phe Tyr Asn Ala Lys Ala Gly Leu Cys Gln Thr
                20                  25                 30
Phe Val Tyr Gly Gly Cys Arg Ala Lys Arg Asn Asn Phe Lys Ser Ala
            35              40              45
Glu Asp Cys Met Arg Thr Cys Gly Gly Ala
        50              55
```

( 2 ) INFORMATION FOR SEQ ID NO: 49:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 49:

```
Arg Pro Asp Phe Cys Leu Glu Pro Pro Tyr Thr Gly Ile Cys Arg Ala
 1               5                  10                 15
His Val Arg His Tyr Phe Tyr Asn Ala Lys Ala Gly Leu Cys Gln Thr
                20                  25                 30
Phe Val Tyr Gly Gly Cys Leu Ala Lys Arg Asn Asn Phe Lys Ser Ala
            35              40              45
Glu Asp Cys Met Arg Thr Cys Gly Gly Ala
        50              55
```

( 2 ) INFORMATION FOR SEQ ID NO: 50:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 50:

```
Arg Pro Asp Phe Cys Leu Glu Pro Pro Tyr Glu Gly Ile Cys Arg Ala
 1               5                  10                 15
His Val Arg His Tyr Phe Tyr Asn Ala Lys Ala Gly Leu Cys Gln Thr
                20                  25                 30
Phe Val Tyr Gly Gly Cys Leu Ala Lys Arg Asn Asn Phe Lys Ser Ala
            35              40              45
Glu Asp Cys Met Arg Thr Cys Gly Gly Ala
        50              55
```

( 2 ) INFORMATION FOR SEQ ID NO: 51:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 51:

| Arg | Pro | Asp | Phe | Cys | Leu | Glu | Pro | Pro | Tyr | Thr | Gly | Ile | Cys | Arg | Ala |
|---|---|---|---|---|---|---|---|---|---|---|---|---|---|---|---|
| 1 | | | | 5 | | | | | 10 | | | | | 15 | |
| Asn | Phe | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Leu | Ala | Lys | Arg | Asn | Asn | Phe | Glu | Ser | Ala |
| | | | 35 | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 52:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 52:

| Arg | Pro | Asp | Phe | Cys | Leu | Glu | Pro | Pro | Tyr | Thr | Gly | Ile | Cys | Arg | Ala |
|---|---|---|---|---|---|---|---|---|---|---|---|---|---|---|---|
| 1 | | | | 5 | | | | | 10 | | | | | 15 | |
| Ser | Phe | Asn | Arg | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Leu | Ala | Lys | Arg | Asn | Asn | Phe | Glu | Ser | Ala |
| | | | 35 | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 53:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 53:

| Arg | Pro | Asp | Phe | Cys | Leu | Glu | Pro | Pro | Tyr | Thr | Gly | Ile | Cys | Arg | Ala |
|---|---|---|---|---|---|---|---|---|---|---|---|---|---|---|---|
| 1 | | | | 5 | | | | | 10 | | | | | 15 | |
| Ala | Phe | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Leu | Ala | Lys | Arg | Asn | Asn | Phe | Glu | Ser | Ala |
| | | | 35 | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 54:

(i) SEQUENCE CHARACTERISTICS:
  (A) LENGTH: 58 amino acids
  (B) TYPE: amino acid
  (C) STRANDEDNESS: single
  (D) TOPOLOGY: linear ( i i ) MOLECULE TYPE: peptide ( x i ) SEQUENCE DESCRIPTION: SEQ ID NO: 54:

Arg Pro Asp Phe Cys Leu Glu Pro Pro Tyr Thr Gly Ile Cys Arg Ser
1               5                   10                  15

Tyr Phe Lys Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35              40                  45

Glu Asp Cys Met Arg Thr Cys Gly Gly Ala
    50              55

( 2 ) INFORMATION FOR SEQ ID NO: 55:

( i ) SEQUENCE CHARACTERISTICS:
       ( A ) LENGTH: 58 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO: 55:

Arg Pro Asp Phe Cys Leu Glu Pro Pro Tyr Thr Gly Ile Cys Arg Ala
1               5                   10                  15

Ser Phe Lys Leu Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35              40                  45

Glu Asp Cys Met Arg Thr Cys Gly Gly Ala
    50              55

( 2 ) INFORMATION FOR SEQ ID NO: 56:

( i ) SEQUENCE CHARACTERISTICS:
       ( A ) LENGTH: 58 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO: 56:

Arg Pro Asp Phe Cys Leu Glu Pro Pro Tyr Thr Gly Ile Cys Arg Ala
1               5                   10                  15

His Tyr Lys Leu Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35              40                  45

Glu Asp Cys Met Arg Thr Cys Gly Gly Ala
    50              55

( 2 ) INFORMATION FOR SEQ ID NO: 57:

( i ) SEQUENCE CHARACTERISTICS:
       ( A ) LENGTH: 58 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO: 57:

| Arg | Pro | Asp | Phe | Cys | Leu | Glu | Pro | Pro | Tyr | Thr | Gly | Ile | Cys | Arg | Ala |
| 1 | | | | 5 | | | | | 10 | | | | | 15 | |

| Ser | Phe | Thr | Leu | Tyr | Phe | Tyr | Asn | Ala | Lys | Ala | Gly | Leu | Cys | Gln | Thr |
| | | | 20 | | | | 25 | | | | | 30 | | | |

| Phe | Val | Tyr | Gly | Gly | Cys | Leu | Ala | Lys | Arg | Asn | Asn | Phe | Glu | Ser | Ala |
| | | 35 | | | | 40 | | | | | | 45 | | | |

| Glu | Asp | Cys | Met | Arg | Thr | Cys | Gly | Gly | Ala |
| | 50 | | | | | 55 | | | |

( 2 ) INFORMATION FOR SEQ ID NO: 58:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 58:

| Arg | Pro | Asp | Phe | Cys | Leu | Glu | Pro | Pro | Tyr | Thr | Gly | Ile | Cys | Arg | Ala |
| 1 | | | | 5 | | | | | 10 | | | | | 15 | |

| Ser | Tyr | Thr | Leu | Tyr | Phe | Tyr | Asn | Ala | Lys | Ala | Gly | Leu | Cys | Gln | Thr |
| | | | 20 | | | | 25 | | | | | 30 | | | |

| Phe | Val | Tyr | Gly | Gly | Cys | Leu | Ala | Lys | Arg | Asn | Asn | Phe | Glu | Ser | Ala |
| | | 35 | | | | 40 | | | | | | 45 | | | |

| Glu | Asp | Cys | Met | Arg | Thr | Cys | Gly | Gly | Ala |
| | 50 | | | | | 55 | | | |

( 2 ) INFORMATION FOR SEQ ID NO: 59:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 59:

| Arg | Pro | Asp | Phe | Cys | Leu | Glu | Pro | Pro | Tyr | Thr | Gly | Ile | Cys | Arg | Ala |
| 1 | | | | 5 | | | | | 10 | | | | | 15 | |

| Ser | Tyr | Lys | Leu | Tyr | Phe | Tyr | Asn | Ala | Lys | Ala | Gly | Leu | Cys | Gln | Thr |
| | | | 20 | | | | 25 | | | | | 30 | | | |

| Phe | Val | Tyr | Gly | Gly | Cys | Leu | Ala | Lys | Arg | Asn | Asn | Phe | Glu | Ser | Ala |
| | | 35 | | | | 40 | | | | | | 45 | | | |

| Glu | Asp | Cys | Met | Arg | Thr | Cys | Gly | Gly | Ala |
| | 50 | | | | | 55 | | | |

( 2 ) INFORMATION FOR SEQ ID NO: 60:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 60:

| Arg | Pro | Asp | Phe | Cys | Leu | Glu | Pro | Pro | Tyr | Thr | Gly | Ile | Cys | Arg | Ala |
| 1 | | | | 5 | | | | | 10 | | | | | 15 | |

| Met | Phe | His | Leu | Tyr | Phe | Tyr | Asn | Ala | Lys | Ala | Gly | Leu | Cys | Gln | Thr |
| | | | 20 | | | | 25 | | | | | 30 | | | |

```
Phe  Val  Tyr  Gly  Gly  Cys  Leu  Ala  Lys  Arg  Asn  Asn  Phe  Glu  Ser  Ala
          35                  40                           45

Glu  Asp  Cys  Met  Arg  Thr  Cys  Gly  Gly  Ala
     50                       55
```

( 2 ) INFORMATION FOR SEQ ID NO: 61:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 61:

```
Arg  Pro  Asp  Phe  Cys  Leu  Glu  Pro  Pro  Tyr  Thr  Gly  Ile  Cys  Arg  Ala
1               5                        10                            15

Ile  Tyr  Val  Leu  Tyr  Phe  Tyr  Asn  Ala  Lys  Ala  Gly  Leu  Cys  Gln  Thr
          20                       25                           30

Phe  Val  Tyr  Gly  Gly  Cys  Leu  Ala  Lys  Arg  Asn  Asn  Phe  Glu  Ser  Ala
          35                  40                           45

Glu  Asp  Cys  Met  Arg  Thr  Cys  Gly  Gly  Ala
     50                       55
```

( 2 ) INFORMATION FOR SEQ ID NO: 62:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 62:

```
Arg  Pro  Asp  Phe  Cys  Leu  Glu  Pro  Pro  Tyr  Thr  Gly  Ile  Cys  Arg  Ala
1               5                        10                            15

Asn  Phe  Asn  Leu  Tyr  Phe  Tyr  Asn  Ala  Lys  Ala  Gly  Leu  Cys  Gln  Thr
          20                       25                           30

Phe  Val  Tyr  Gly  Gly  Cys  Leu  Ala  Lys  Arg  Asn  Asn  Phe  Glu  Ser  Ala
          35                  40                           45

Glu  Asp  Cys  Met  Arg  Thr  Cys  Gly  Gly  Ala
     50                       55
```

( 2 ) INFORMATION FOR SEQ ID NO: 63:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 63:

```
Arg  Pro  Asp  Phe  Cys  Leu  Glu  Pro  Pro  Tyr  Thr  Gly  Ile  Cys  Arg  Ala
1               5                        10                            15

Tyr  Tyr  Lys  Leu  Tyr  Phe  Tyr  Asn  Ala  Lys  Ala  Gly  Leu  Cys  Gln  Thr
          20                       25                           30

Phe  Val  Tyr  Gly  Gly  Cys  Leu  Ala  Lys  Arg  Asn  Asn  Phe  Glu  Ser  Ala
          35                  40                           45

Glu  Asp  Cys  Met  Arg  Thr  Cys  Gly  Gly  Ala
```

(2) INFORMATION FOR SEQ ID NO: 64:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 64:

Arg Pro Asp Phe Cys Leu Glu Pro Pro Tyr Thr Gly Ile Cys Arg Ala
1               5                   10                  15
Ala Phe Lys Leu Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
        50                  55

(2) INFORMATION FOR SEQ ID NO: 65:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 65:

Arg Pro Asp Phe Cys Leu Glu Pro Pro Tyr Thr Gly Ile Cys Arg Ala
1               5                   10                  15
Leu His Ile Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
        50                  55

(2) INFORMATION FOR SEQ ID NO: 66:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 66:

Arg Pro Asp Phe Cys Leu Glu Pro Pro Tyr Thr Gly Ile Cys Arg Ala
1               5                   10                  15
Ile Tyr Lys Leu Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
        50                  55

(2) INFORMATION FOR SEQ ID NO: 67:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 67:

```
Arg Pro Asp Phe Cys Leu Glu Pro Pro Tyr Thr Gly Ile Cys Arg Ala
1               5                   10                  15

Ala Phe Asn Leu Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 68:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 68:

```
Arg Pro Asp Phe Cys Leu Glu Pro Pro Tyr Thr Gly Ile Cys Arg Ala
1               5                   10                  15

Phe Tyr Lys Leu Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 69:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 69:

```
Arg Pro Asp Phe Cys Leu Glu Pro Pro Tyr Thr Gly Ile Cys Arg Ala
1               5                   10                  15

Leu Tyr Lys Leu Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 70:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 70:

| Arg | Pro | Asp | Phe | Cys | Leu | Glu | Pro | Pro | Tyr | Asp | Gly | Pro | Cys | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | His | Leu | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Tyr | Tyr | Gly | Gly | Cys | Leu | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |     |     |     |     |     |     |
|     | 50  |     |     |     |     | 55  |     |     |     |     |     |     |     |     |     |

( 2 ) INFORMATION FOR SEQ ID NO: 71:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 71:

| Arg | Pro | Asp | Phe | Cys | Leu | Glu | Pro | Pro | Tyr | Pro | Gly | Tyr | Cys | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | His | Leu | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Thr | Tyr | Gly | Gly | Cys | His | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |     |     |     |     |     |     |
|     | 50  |     |     |     |     | 55  |     |     |     |     |     |     |     |     |     |

( 2 ) INFORMATION FOR SEQ ID NO: 72:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 72:

| Arg | Pro | Asp | Phe | Cys | Leu | Glu | Pro | Pro | Tyr | Thr | Gly | Pro | Cys | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | His | His | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Phe | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |     |     |     |     |     |     |
|     | 50  |     |     |     |     | 55  |     |     |     |     |     |     |     |     |     |

( 2 ) INFORMATION FOR SEQ ID NO: 73:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 73:

```
Arg  Pro  Asp  Phe  Cys  Leu  Glu  Pro  Pro  Tyr  Pro  Gly  Ile  Cys  Arg  Ala
1              5                        10                       15

Leu  His  Pro  Arg  Tyr  Phe  Tyr  Asn  Ala  Lys  Ala  Gly  Leu  Cys  Gln  Thr
          20                       25                            30

Phe  His  Tyr  Gly  Gly  Cys  Leu  Ala  Lys  Arg  Asn  Asn  Phe  Glu  Ser  Ala
          35                  40                            45

Glu  Asp  Cys  Met  Arg  Thr  Cys  Gly  Gly  Ala
     50                       55
```

( 2 ) INFORMATION FOR SEQ ID NO: 74:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 74:

```
Arg  Pro  Asp  Phe  Cys  Leu  Glu  Pro  Pro  Tyr  Val  Gly  Ile  Cys  Arg  Ala
1              5                        10                       15

Leu  His  Thr  Arg  Tyr  Phe  Tyr  Asn  Ala  Lys  Ala  Gly  Leu  Cys  Gln  Thr
          20                       25                            30

Phe  Ser  Tyr  Gly  Gly  Cys  Phe  Ala  Lys  Arg  Asn  Asn  Phe  Glu  Ser  Ala
          35                  40                            45

Glu  Asp  Cys  Met  Arg  Thr  Cys  Gly  Gly  Ala
     50                       55
```

( 2 ) INFORMATION FOR SEQ ID NO: 75:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 75:

```
Arg  Pro  Asp  Phe  Cys  Leu  Glu  Pro  Pro  Tyr  Ser  Gly  Leu  Cys  Arg  Ala
1              5                        10                       15

Leu  His  Lys  Arg  Tyr  Phe  Tyr  Asn  Ala  Lys  Ala  Gly  Leu  Cys  Gln  Thr
          20                       25                            30

Phe  Tyr  Tyr  Gly  Gly  Cys  Tyr  Ala  Lys  Arg  Asn  Asn  Phe  Glu  Ser  Ala
          35                  40                            45

Glu  Asp  Cys  Met  Arg  Thr  Cys  Gly  Gly  Ala
     50                       55
```

( 2 ) INFORMATION FOR SEQ ID NO: 76:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 76:

```
Arg  Pro  Asp  Phe  Cys  Leu  Glu  Pro  Pro  Tyr  Leu  Gly  Ile  Cys  Arg  Ala
1              5                        10                       15

Leu  His  Thr  Arg  Tyr  Phe  Tyr  Asn  Ala  Lys  Ala  Gly  Leu  Cys  Gln  Thr
          20                       25                            30
```

```
Phe  Ser  Tyr  Gly  Gly  Cys  Leu  Ala  Lys  Arg  Asn  Asn  Phe  Glu  Ser  Ala
          35                  40                           45

Glu  Asp  Cys  Met  Arg  Thr  Cys  Gly  Gly  Ala
     50                       55
```

( 2 ) INFORMATION FOR SEQ ID NO: 77:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 77:

```
Arg  Pro  Asp  Phe  Cys  Leu  Glu  Pro  Pro  Tyr  Pro  Gly  Ile  Cys  Arg  Ala
1                   5                        10                          15

Leu  His  Lys  Arg  Tyr  Phe  Tyr  Asn  Ala  Lys  Ala  Gly  Leu  Cys  Gln  Thr
               20                       25                           30

Phe  His  Tyr  Gly  Gly  Cys  Phe  Ala  Lys  Arg  Asn  Asn  Phe  Glu  Ser  Ala
          35                  40                           45

Glu  Asp  Cys  Met  Arg  Thr  Cys  Gly  Gly  Ala
     50                       55
```

( 2 ) INFORMATION FOR SEQ ID NO: 78:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 78:

```
Arg  Pro  Asp  Phe  Cys  Leu  Glu  Pro  Pro  Tyr  Ser  Gly  Leu  Cys  Arg  Ala
1                   5                        10                          15

Leu  His  Lys  Arg  Tyr  Phe  Tyr  Asn  Ala  Lys  Ala  Gly  Leu  Cys  Gln  Thr
               20                       25                           30

Phe  Tyr  Tyr  Gly  Gly  Cys  Phe  Ala  Lys  Arg  Asn  Asn  Phe  Glu  Ser  Ala
          35                  40                           45

Glu  Asp  Cys  Met  Arg  Thr  Cys  Gly  Gly  Ala
     50                       55
```

( 2 ) INFORMATION FOR SEQ ID NO: 79:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 79:

```
Arg  Pro  Asp  Phe  Cys  Leu  Glu  Pro  Pro  Tyr  Pro  Gly  Ile  Cys  Arg  Ala
1                   5                        10                          15

Leu  His  Lys  Arg  Tyr  Phe  Tyr  Asn  Ala  Lys  Ala  Gly  Leu  Cys  Gln  Thr
               20                       25                           30

Phe  Tyr  Tyr  Gly  Gly  Cys  Met  Ala  Lys  Arg  Asn  Asn  Phe  Glu  Ser  Ala
          35                  40                           45

Glu  Asp  Cys  Met  Arg  Thr  Cys  Gly  Gly  Ala
```

(2) INFORMATION FOR SEQ ID NO: 80:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

```
Arg Pro Asp Phe Cys Leu Glu Pro Pro Tyr Glu Gly Met Cys Arg Ala
  1               5                  10                  15

Ile His Lys Arg Tyr Phe Tyr Asn Ala Lys Ala Gly Leu Cys Gln Thr
             20                  25                  30

Phe Thr Tyr Gly Gly Cys Met Ala Lys Arg Asn Asn Phe Glu Ser Ala
         35                  40                  45

Glu Asp Cys Met Arg Thr Cys Gly Gly Ala
         50                  55
```

(2) INFORMATION FOR SEQ ID NO: 81:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

```
Arg Pro Asp Phe Cys Leu Glu Pro Pro Tyr Pro Gly Val Cys Arg Ala
  1               5                  10                  15

Leu His Lys Arg Tyr Phe Tyr Asn Ala Lys Ala Gly Leu Cys Gln Thr
             20                  25                  30

Phe Ser Tyr Gly Gly Cys Gln Ala Lys Arg Asn Asn Phe Glu Ser Ala
         35                  40                  45

Glu Asp Cys Met Arg Thr Cys Gly Gly Ala
         50                  55
```

(2) INFORMATION FOR SEQ ID NO: 82:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

```
Arg Pro Asp Phe Cys Leu Glu Pro Pro Tyr Arg Gly Val Cys Arg Ala
  1               5                  10                  15

Ile His Lys Arg Tyr Phe Tyr Asn Ala Lys Ala Gly Leu Cys Gln Thr
             20                  25                  30

Phe Leu Tyr Gly Gly Cys Met Ala Lys Arg Asn Asn Phe Glu Ser Ala
         35                  40                  45

Glu Asp Cys Met Arg Thr Cys Gly Gly Ala
         50                  55
```

(2) INFORMATION FOR SEQ ID NO: 83:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 83:

```
Arg Pro Asp Phe Cys Leu Glu Pro Pro Tyr Pro Gly Leu Cys Arg Ala
 1               5                  10                  15

Leu His Lys Arg Tyr Phe Tyr Asn Ala Lys Ala Gly Leu Cys Gln Thr
            20                  25                  30

Phe Tyr Tyr Gly Gly Cys Tyr Ala Lys Arg Asn Asn Phe Glu Ser Ala
            35                  40                  45

Glu Asp Cys Met Arg Thr Cys Gly Gly Ala
        50                  55
```

( 2 ) INFORMATION FOR SEQ ID NO: 84:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 84:

```
Arg Pro Asp Phe Cys Leu Glu Pro Pro Tyr Ala Gly Tyr Cys Arg Ala
 1               5                  10                  15

Leu His Lys Arg Tyr Phe Tyr Asn Ala Lys Ala Gly Leu Cys Gln Thr
            20                  25                  30

Phe Tyr Tyr Gly Gly Cys Phe Ala Lys Arg Asn Asn Phe Glu Ser Ala
            35                  40                  45

Glu Asp Cys Met Arg Thr Cys Gly Gly Ala
        50                  55
```

( 2 ) INFORMATION FOR SEQ ID NO: 85:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 85:

```
Arg Pro Asp Phe Cys Leu Glu Pro Pro Tyr Arg Gly Val Cys Arg Ala
 1               5                  10                  15

Ile His Gln Arg Tyr Phe Tyr Asn Ala Lys Ala Gly Leu Cys Gln Thr
            20                  25                  30

Phe Ile Tyr Gly Gly Cys Met Ala Lys Arg Asn Asn Phe Glu Ser Ala
            35                  40                  45

Glu Asp Cys Met Arg Thr Cys Gly Gly Ala
        50                  55
```

( 2 ) INFORMATION FOR SEQ ID NO: 86:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 86:

| Arg | Pro | Asp | Phe | Cys | Leu | Glu | Pro | Pro | Tyr | Thr | Gly | Tyr | Cys | Arg | Ala |
|-----|-----|-----|-----|-----|-----|-----|-----|-----|-----|-----|-----|-----|-----|-----|-----|
| 1 | | | | 5 | | | | | 10 | | | | | 15 | |

| Leu | His | Lys | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
| | | | 20 | | | | | 25 | | | | | 30 | | |

| Phe | Tyr | Tyr | Gly | Gly | Cys | Phe | Ala | Lys | Arg | Asn | Asn | Phe | Glu | Ser | Ala |
|-----|-----|-----|-----|-----|-----|-----|-----|-----|-----|-----|-----|-----|-----|-----|-----|
| | | 35 | | | | | 40 | | | | | 45 | | | |

| Glu | Asp | Cys | Met | Arg | Thr | Cys | Gly | Gly | Ala |
|-----|-----|-----|-----|-----|-----|-----|-----|-----|-----|
| | 50 | | | | | 55 | | | |

( 2 ) INFORMATION FOR SEQ ID NO: 87:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 87:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
| 1 | | | | 5 | | | | | 10 | | | | | 15 | |

| Leu | His | Lys | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
| | | | 20 | | | | | 25 | | | | | 30 | | |

| Phe | Trp | Tyr | Gly | Gly | Cys | Leu | Ala | Lys | Arg | Asn | Asn | Phe | Glu | Ser | Ala |
|-----|-----|-----|-----|-----|-----|-----|-----|-----|-----|-----|-----|-----|-----|-----|-----|
| | | 35 | | | | | 40 | | | | | 45 | | | |

| Glu | Asp | Cys | Met | Arg | Thr | Cys | Gly | Gly | Ala |
|-----|-----|-----|-----|-----|-----|-----|-----|-----|-----|
| | 50 | | | | | 55 | | | |

( 2 ) INFORMATION FOR SEQ ID NO: 88:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 88:

| Arg | Pro | Asp | Phe | Cys | Leu | Glu | Pro | Pro | Tyr | Gln | Gly | Ile | Cys | Arg | Ala |
|-----|-----|-----|-----|-----|-----|-----|-----|-----|-----|-----|-----|-----|-----|-----|-----|
| 1 | | | | 5 | | | | | 10 | | | | | 15 | |

| Leu | His | Lys | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
| | | | 20 | | | | | 25 | | | | | 30 | | |

| Phe | Met | Tyr | Gly | Gly | Cys | Leu | Ala | Lys | Arg | Asn | Asn | Phe | Glu | Ser | Ala |
|-----|-----|-----|-----|-----|-----|-----|-----|-----|-----|-----|-----|-----|-----|-----|-----|
| | | 35 | | | | | 40 | | | | | 45 | | | |

| Glu | Asp | Cys | Met | Arg | Thr | Cys | Gly | Gly | Ala |
|-----|-----|-----|-----|-----|-----|-----|-----|-----|-----|
| | 50 | | | | | 55 | | | |

( 2 ) INFORMATION FOR SEQ ID NO: 89:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 89:

```
Arg  Pro  Asp  Phe  Cys  Leu  Glu  Pro  Pro  Tyr  Pro  Gly  Ile  Cys  Arg  Ala
1                   5                        10                       15

Leu  His  Lys  Arg  Tyr  Phe  Tyr  Asn  Ala  Lys  Ala  Gly  Leu  Cys  Gln  Thr
               20                       25                       30

Phe  Tyr  Tyr  Gly  Gly  Cys  Met  Ala  Lys  Arg  Asn  Asn  Phe  Glu  Ser  Ala
          35                       40                       45

Glu  Asp  Cys  Met  Arg  Thr  Cys  Gly  Gly  Ala
     50                       55
```

( 2 ) INFORMATION FOR SEQ ID NO: 90:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 90:

```
Arg  Pro  Asp  Phe  Cys  Leu  Glu  Pro  Pro  Tyr  Glu  Gly  Leu  Cys  Arg  Ala
1                   5                        10                       15

Leu  His  Lys  Arg  Tyr  Phe  Tyr  Asn  Ala  Lys  Ala  Gly  Leu  Cys  Gln  Thr
               20                       25                       30

Phe  Tyr  Tyr  Gly  Gly  Cys  Phe  Ala  Lys  Arg  Asn  Asn  Phe  Glu  Ser  Ala
          35                       40                       45

Glu  Asp  Cys  Met  Arg  Thr  Cys  Gly  Gly  Ala
     50                       55
```

( 2 ) INFORMATION FOR SEQ ID NO: 91:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 91:

```
Arg  Pro  Asp  Phe  Cys  Leu  Glu  Pro  Pro  Tyr  Glu  Gly  Phe  Cys  Arg  Ala
1                   5                        10                       15

Tyr  Phe  Lys  Arg  Tyr  Phe  Tyr  Asn  Ala  Lys  Ala  Gly  Leu  Cys  Gln  Thr
               20                       25                       30

Phe  Thr  Tyr  Gly  Gly  Cys  Phe  Ala  Lys  Arg  Asn  Asn  Phe  Glu  Ser  Ala
          35                       40                       45

Glu  Asp  Cys  Met  Arg  Thr  Cys  Gly  Gly  Ala
     50                       55
```

( 2 ) INFORMATION FOR SEQ ID NO: 92:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 92:

```
Arg  Pro  Asp  Phe  Cys  Leu  Glu  Pro  Pro  Tyr  Val  Gly  Asp  Cys  Arg  Ala
1                   5                        10                       15

Tyr  Phe  Lys  Arg  Tyr  Phe  Tyr  Asn  Ala  Lys  Ala  Gly  Leu  Cys  Gln  Thr
               20                       25                       30
```

```
Phe Val Phe Gly Gly Cys Leu Ala Lys Arg Asn Asn Phe Glu Ser Ala
        35              40                      45

Glu Asp Cys Met Arg Thr Cys Gly Gly Ala
    50                  55
```

( 2 ) INFORMATION FOR SEQ ID NO: 93:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 93:

```
Arg Pro Asp Phe Cys Leu Glu Pro Pro Tyr Glu Gly Phe Cys Arg Ala
1                5                   10                  15

His Phe Lys Arg Tyr Phe Tyr Asn Ala Lys Ala Gly Leu Cys Gln Ser
            20                  25                  30

Phe Val Tyr Gly Gly Cys Phe Ala Lys Arg Asn Asn Phe Glu Ser Ala
        35              40                      45

Glu Asp Cys Met Arg Thr Cys Gly Gly Ala
    50                  55
```

( 2 ) INFORMATION FOR SEQ ID NO: 94:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 94:

```
Arg Pro Asp Phe Cys Leu Glu Pro Ala Tyr Glu Gly Tyr Cys Arg Ala
1                5                   10                  15

Tyr Ile Lys Arg Tyr Phe Phe Asn Ala Lys Ala Gly Leu Cys Gln Thr
            20                  25                  30

Phe His Tyr Gly Gly Cys Phe Ala Lys Arg Asn Asn Phe Glu Ser Ala
        35              40                      45

Glu Asp Cys Met Arg Thr Cys Gly Gly Ala
    50                  55
```

( 2 ) INFORMATION FOR SEQ ID NO: 95:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 95:

```
Arg Pro Asp Phe Cys Leu Glu Pro Pro Tyr Thr Gly His Cys Arg Ala
1                5                   10                  15

Phe Phe Thr Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
        35              40                      45

Glu Asp Cys Met Arg Thr Cys Gly Gly Ala
```

( 2 ) INFORMATION FOR SEQ ID NO: 96:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 96:

Arg Pro Asp Phe Cys Leu Glu Pro Pro Tyr Thr Gly His Cys Arg Ala
1               5                   10                  15

Tyr Phe Lys Arg Tyr Phe Tyr Asn Ala Lys Ala Gly Leu Cys Gln Thr
            20                  25                  30

Phe Ile Tyr Gly Gly Cys Phe Ala Lys Arg Asn Asn Phe Glu Ser Ala
        35                  40                  45

Glu Asp Cys Met Arg Thr Cys Gly Gly Ala
        50                  55

( 2 ) INFORMATION FOR SEQ ID NO: 97:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 97:

Arg Pro Asp Phe Cys Leu Glu Pro Ala Tyr Glu Gly Phe Cys Arg Ala
1               5                   10                  15

Tyr Phe Phe Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
        35                  40                  45

Glu Asp Cys Met Arg Thr Cys Gly Gly Ala
        50                  55

( 2 ) INFORMATION FOR SEQ ID NO: 98:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 98:

Arg Pro Asp Phe Cys Leu Glu Pro Pro His Ser Gly Ile Cys Arg Ala
1               5                   10                  15

Tyr Phe Lys Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
        35                  40                  45

Glu Asp Cys Met Arg Thr Cys Gly Gly Ala
        50                  55

( 2 ) INFORMATION FOR SEQ ID NO: 99:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 99:

```
Arg Pro Asp Phe Cys Leu Glu Pro Pro Tyr Glu Gly Ile Cys Arg Ala
 1               5                  10                  15
Leu Phe Thr Arg Tyr Phe Tyr Asn Ala Lys Ala Gly Leu Cys Gln Thr
             20                  25                  30
Phe His Tyr Gly Gly Cys Leu Ala Lys Arg Asn Asn Phe Glu Ser Ala
             35                  40                  45
Glu Asp Cys Met Arg Thr Cys Gly Gly Ala
 50                      55
```

( 2 ) INFORMATION FOR SEQ ID NO: 100:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 100:

```
Arg Pro Asp Phe Cys Leu Glu Pro Pro Ser Glu Gly Ile Cys Arg Ala
 1               5                  10                  15
Tyr His Lys Arg Tyr Phe Tyr Asn Ala Lys Ala Gly Leu Cys Gln Thr
             20                  25                  30
Phe Val Tyr Gly Gly Cys Leu Ala Lys Arg Asn Asn Phe Glu Ser Ala
             35                  40                  45
Glu Asp Cys Met Arg Thr Cys Gly Gly Ala
 50                      55
```

( 2 ) INFORMATION FOR SEQ ID NO: 101:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 101:

```
Arg Pro Asp Phe Cys Leu Glu Pro Pro Tyr Glu Gly Asn Cys Arg Ala
 1               5                  10                  15
Phe Phe Arg Arg Tyr Phe Tyr Asn Ala Lys Ala Gly Leu Cys Gln Thr
             20                  25                  30
Phe Ile Tyr Gly Gly Cys Leu Ala Lys Arg Asn Asn Phe Glu Ser Ala
             35                  40                  45
Glu Asp Cys Met Arg Thr Cys Gly Gly Ala
 50                      55
```

( 2 ) INFORMATION FOR SEQ ID NO: 102:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear (i i) MOLECULE TYPE: peptide (x i) SEQUENCE DESCRIPTION: SEQ ID NO: 102:

| Arg | Pro | Asp | Phe | Cys | Leu | Glu | Pro | Pro | Tyr | Leu | Gly | Ile | Cys | Arg | Ala |
|---|---|---|---|---|---|---|---|---|---|---|---|---|---|---|---|
| 1 | | | | 5 | | | | | 10 | | | | | 15 | |
| Tyr | Leu | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Tyr | Tyr | Gly | Gly | Cys | Leu | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 103:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 103:

| Arg | Pro | Asp | Phe | Cys | Leu | Glu | Pro | Pro | Tyr | Glu | Gly | Asn | Cys | Arg | Ala |
|---|---|---|---|---|---|---|---|---|---|---|---|---|---|---|---|
| 1 | | | | 5 | | | | | 10 | | | | | 15 | |
| Tyr | Leu | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Ala | Tyr | Gly | Gly | Cys | Phe | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 104:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 104:

| Arg | Pro | Asp | Phe | Cys | Leu | Glu | Pro | Pro | Tyr | Glu | Gly | Ile | Cys | Arg | Ala |
|---|---|---|---|---|---|---|---|---|---|---|---|---|---|---|---|
| 1 | | | | 5 | | | | | 10 | | | | | 15 | |
| Tyr | Phe | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Ser | Tyr | Gly | Gly | Cys | Phe | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 105:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 105:

Arg Pro Asp Phe Cys Leu Glu Pro Pro Tyr Glu Gly Ile Cys Arg Ala
1               5                   10                  15

Phe Asn Lys Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35                  40                  45

Glu Asp Cys Met Arg Thr Cys Gly Gly Ala
50                      55

( 2 ) INFORMATION FOR SEQ ID NO: 106:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 106:

Arg Pro Asp Phe Cys Leu Glu Ser Pro Tyr Ala Gly Ile Cys Arg Ala
1               5                   10                  15

Tyr Ile Lys Arg Tyr Phe Tyr Asn Ala Lys Ala Gly Leu Cys Gln Thr
            20                  25                  30

Phe Tyr Tyr Gly Gly Cys Phe Ala Lys Arg Asn Asn Phe Glu Ser Ala
        35                  40                  45

Glu Asp Cys Met Arg Thr Cys Gly Gly Ala
50                      55

( 2 ) INFORMATION FOR SEQ ID NO: 107:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 107:

Arg Pro Asp Phe Cys Leu Glu Pro Pro Tyr Glu Gly Ile Cys Arg Ala
1               5                   10                  15

Leu His Lys Arg Tyr Phe Tyr Asn Ala Lys Ala Gly Leu Cys Gln Thr
            20                  25                  30

Phe Tyr Tyr Gly Gly Cys Leu Ala Lys Arg Asn Asn Phe Glu Ser Ala
        35                  40                  45

Glu Asp Cys Met Arg Thr Cys Gly Gly Ala
50                      55

( 2 ) INFORMATION FOR SEQ ID NO: 108:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 108:

Arg Pro Asp Phe Cys Leu Glu Pro Pro Tyr Glu Gly Ile Cys Arg Ala
1               5                   10                  15

Tyr Phe Lys Arg Tyr Phe Tyr Asn Ala Lys Ala Gly Leu Cys Gln Thr
            20                  25                  30

Phe Glu Tyr Gly Gly Cys Leu Ala Lys Arg Asn Asn Phe Glu Ser Ala
            35                          40                          45

Glu Asp Cys Met Arg Thr Cys Gly Gly Ala
        50                      55

( 2 ) INFORMATION FOR SEQ ID NO: 109:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 109:

Arg Pro Asp Phe Cys Leu Glu Pro Pro Tyr Thr Gly Ile Cys Arg Ala
1               5                   10                      15

Tyr Ile Thr Arg Tyr Phe Tyr Asn Ala Lys Ala Gly Leu Cys Gln Thr
            20                  25                      30

Phe Val Tyr Gly Gly Cys Leu Ala Lys Arg Asn Asn Phe Glu Ser Ala
            35                          40                          45

Glu Asp Cys Met Arg Thr Cys Gly Gly Ala
        50                      55

( 2 ) INFORMATION FOR SEQ ID NO: 110:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 110:

Ala Pro Asp Phe Cys Leu Glu Pro Pro Tyr Thr Gly Ile Cys Arg Ala
1               5                   10                      15

Tyr Ile Thr Arg Tyr Phe Tyr Asn Ala Lys Ala Gly Leu Cys Gln Thr
            20                  25                      30

Phe Val Tyr Gly Gly Cys Leu Ala Lys Arg Asn Asn Phe Glu Ser Ala
            35                          40                          45

Glu Asp Cys Met Arg Thr Cys Gly Gly Ala
        50                      55

( 2 ) INFORMATION FOR SEQ ID NO: 111:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 111:

Ala Pro Asp Phe Cys Leu Glu Pro Pro Tyr Thr Gly Ile Cys Arg Ala
1               5                   10                      15

Tyr Ile Thr Arg Tyr Phe Tyr Asn Ala Lys Ala Gly Leu Cys Gln Thr
            20                  25                      30

Phe Val Tyr Gly Gly Cys Leu Ala Lys Arg Asn Asn Phe Lys Ser Ala
            35                          40                          45

Glu Asp Cys Met Arg Thr Cys Gly Gly Ala ( 2 ) INFORMATION FOR SEQ ID NO: 112:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 112:

```
Ala  Pro  Asp  Phe  Cys  Leu  Glu  Pro  Pro  Tyr  Thr  Gly  Pro  Cys  Arg  Ala
 1              5                        10                       15
Tyr  Ile  Thr  Arg  Tyr  Phe  Tyr  Asn  Ala  Lys  Ala  Gly  Leu  Cys  Gln  Thr
              20                        25                       30
Phe  Val  Tyr  Gly  Gly  Cys  Leu  Ala  Lys  Arg  Asn  Asn  Phe  Glu  Ser  Ala
              35                        40                       45
Glu  Asp  Cys  Met  Arg  Thr  Cys  Gly  Gly  Ala
         50                   55
```

( 2 ) INFORMATION FOR SEQ ID NO: 113:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 113:

```
Ala  Pro  Asp  Phe  Cys  Leu  Glu  Pro  Pro  Tyr  Thr  Gly  Ile  Cys  Arg  Ala
 1              5                        10                       15
Tyr  Ile  Thr  Arg  Tyr  Phe  Tyr  Asn  Ala  Lys  Ala  Gly  Leu  Cys  Gln  Arg
              20                        25                       30
Phe  Val  Tyr  Gly  Gly  Cys  Leu  Ala  Lys  Arg  Asn  Asn  Phe  Glu  Ser  Ala
              35                        40                       45
Glu  Asp  Cys  Met  Arg  Thr  Cys  Gly  Gly  Ala
         50                   55
```

( 2 ) INFORMATION FOR SEQ ID NO: 114:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 114:

```
Ala  Pro  Asp  Phe  Cys  Leu  Glu  Pro  Pro  Tyr  Thr  Gly  Ile  Cys  Arg  Ala
 1              5                        10                       15
Tyr  Ile  Ile  Arg  Tyr  Phe  Tyr  Asn  Ala  Lys  Ala  Gly  Leu  Cys  Gln  Thr
              20                        25                       30
Phe  Val  Tyr  Gly  Gly  Cys  Leu  Ala  Lys  Arg  Asn  Asn  Phe  Lys  Ser  Ala
              35                        40                       45
Glu  Asp  Cys  Met  Arg  Thr  Cys  Gly  Gly  Ala
         50                   55
```

( 2 ) INFORMATION FOR SEQ ID NO: 115:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 115:

```
Ala Pro Asp Phe Cys Leu Glu Pro Pro Tyr Thr Gly Phe Cys Arg Ala
1               5                   10                  15
Tyr Ile Thr Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Lys Ser Ala
            35              40                  45
Glu Asp Cys Met Arg Thr Cys Gly Gly Ala
50                      55
```

( 2 ) INFORMATION FOR SEQ ID NO: 116:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 116:

```
Ala Pro Asp Phe Cys Leu Glu Pro Pro Tyr Thr Gly Ile Cys Arg Ala
1               5                   10                  15
Tyr Ile Thr Arg Tyr Phe Tyr Asn Ala Lys Ala Gly Leu Cys Gln Thr
            20                  25                  30
Phe Val Tyr Gly Gly Cys Phe Ala Lys Arg Asn Asn Phe Lys Ser Ala
            35              40                  45
Glu Asp Cys Met Arg Thr Cys Gly Gly Ala
50                      55
```

( 2 ) INFORMATION FOR SEQ ID NO: 117:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 117:

```
Ala Pro Asp Phe Cys Leu Glu Pro Pro Tyr Thr Gly Ile Cys Arg Ala
1               5                   10                  15
Phe Ile Thr Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Lys Ser Ala
            35              40                  45
Glu Asp Cys Met Arg Thr Cys Gly Gly Ala
50                      55
```

( 2 ) INFORMATION FOR SEQ ID NO: 118:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 118:

Ala Pro Asp Phe Cys Leu Glu Pro Pro Tyr Thr Gly Pro Cys Arg Ala
1               5                   10                  15

Tyr Ile Thr Arg Tyr Phe Tyr Asn Ala Lys Ala Gly Leu Cys Gln Thr
            20                  25                  30

Phe Val Tyr Gly Gly Cys Tyr Ala Lys Arg Asn Asn Phe Lys Ser Ala
            35                  40                  45

Glu Asp Cys Met Arg Thr Cys Gly Gly Ala
    50                  55

( 2 ) INFORMATION FOR SEQ ID NO: 119:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 119:

Ala Pro Asp Phe Cys Leu Glu Pro Pro Tyr Thr Gly Pro Cys Arg Ala
1               5                   10                  15

Tyr Ile Thr Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Lys Ser Ala
            35                  40                  45

Glu Asp Cys Met Arg Thr Cys Gly Gly Ala
    50                  55

( 2 ) INFORMATION FOR SEQ ID NO: 120:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 120:

Ala Pro Asp Phe Cys Leu Glu Pro Pro Tyr Thr Gly Ile Cys Arg Ala
1               5                   10                  15

Tyr Ile Lys Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
    50                  55

( 2 ) INFORMATION FOR SEQ ID NO: 121:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 121:

```
Ala Pro Asp Phe Cys Leu Glu Pro Pro Tyr Thr Gly Pro Cys Arg Ala
1               5                   10                  15

Tyr Ile Thr Arg Tyr Phe Tyr Asn Ala Lys Ala Gly Leu Cys Gln Thr
            20                  25                  30

Phe Val Tyr Gly Gly Cys Tyr Ala Lys Arg Asn Asn Phe Tyr Ser Ala
            35                  40                  45

Glu Asp Cys Met Arg Thr Cys Gly Gly Ala
    50                  55
```

( 2 ) INFORMATION FOR SEQ ID NO: 122:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 122:

```
Arg Pro Asp Phe Cys Leu Glu Pro Pro Tyr Thr Gly Ile Cys Arg Ala
1               5                   10                  15

Ala Phe Asn Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 123:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 123:

```
Arg Pro Asp Phe Cys Leu Glu Pro Pro Tyr Thr Gly Ile Cys Arg Ala
1               5                   10                  15

Ala Phe Lys Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 124:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 124:

```
Arg Pro Asp Phe Cys Leu Glu Pro Pro Tyr Thr Gly Ile Cys Arg Ala
1               5                   10                  15

Ser Phe Lys Arg Tyr Phe Tyr Asn Ala Lys Ala Gly Leu Cys Gln Thr
            20                  25                  30
```

```
Phe  Val  Tyr  Gly  Gly  Cys  Leu  Ala  Lys  Arg  Asn  Asn  Phe  Glu  Ser  Ala
          35                       40                      45

Glu  Asp  Cys  Met  Arg  Thr  Cys  Gly  Gly  Ala
     50                       55
```

(2) INFORMATION FOR SEQ ID NO: 125:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 125:

```
Arg  Pro  Asp  Phe  Cys  Leu  Glu  Pro  Pro  Tyr  Thr  Gly  Ile  Cys  Arg  Ala
1                   5                        10                       15

Tyr  Tyr  Lys  Arg  Tyr  Phe  Tyr  Asn  Ala  Lys  Ala  Gly  Leu  Cys  Gln  Thr
               20                       25                            30

Phe  Val  Tyr  Gly  Gly  Cys  Leu  Ala  Lys  Arg  Asn  Asn  Phe  Glu  Ser  Ala
          35                       40                      45

Glu  Asp  Cys  Met  Arg  Thr  Cys  Gly  Gly  Ala
     50                       55
```

(2) INFORMATION FOR SEQ ID NO: 126:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 126:

```
Arg  Pro  Asp  Phe  Cys  Leu  Glu  Pro  Pro  Tyr  Thr  Gly  Ile  Cys  Arg  Ala
1                   5                        10                       15

Ser  Phe  Thr  Arg  Tyr  Phe  Tyr  Asn  Ala  Lys  Ala  Gly  Leu  Cys  Gln  Thr
               20                       25                            30

Phe  Val  Tyr  Gly  Gly  Cys  Leu  Ala  Lys  Arg  Asn  Asn  Phe  Glu  Ser  Ala
          35                       40                      45

Glu  Asp  Cys  Met  Arg  Thr  Cys  Gly  Gly  Ala
     50                       55
```

(2) INFORMATION FOR SEQ ID NO: 127:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 127:

```
Arg  Pro  Asp  Phe  Cys  Leu  Glu  Pro  Pro  Tyr  Pro  Gly  Ile  Cys  Arg  Ala
1                   5                        10                       15

Leu  His  Lys  Arg  Tyr  Phe  Tyr  Asn  Ala  Lys  Ala  Gly  Leu  Cys  Gln  Thr
               20                       25                            30

Phe  Tyr  Tyr  Gly  Gly  Cys  Met  Ala  Lys  Arg  Asn  Asn  Phe  Glu  Ser  Ala
          35                       40                      45

Glu  Asp  Cys  Met  Arg  Thr  Cys  Gly  Gly  Ala
```

-continued

```
        50                              55
```

( 2 ) INFORMATION FOR SEQ ID NO: 128:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 128:

```
Arg Pro Asp Phe Cys Leu Glu Pro Pro Tyr Glu Gly Leu Cys Arg Ala
1                5                   10                  15
Leu His Lys Arg Tyr Phe Tyr Asn Ala Lys Ala Gly Leu Cys Gln Thr
                20                  25                  30
Phe Tyr Tyr Gly Gly Cys Phe Ala Lys Arg Asn Asn Phe Glu Ser Ala
            35              40                  45
Glu Asp Cys Met Arg Thr Cys Gly Gly Ala
    50                  55
```

( 2 ) INFORMATION FOR SEQ ID NO: 129:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 129:

```
Arg Pro Asp Phe Cys Leu Glu Pro Pro Tyr Ser Gly Leu Cys Arg Ala
1                5                   10                  15
Leu His Lys Arg Tyr Phe Tyr Asn Ala Lys Ala Gly Leu Cys Gln Thr
                20                  25                  30
Phe Tyr Tyr Gly Gly Cys Phe Ala Lys Arg Asn Asn Phe Glu Ser Ala
            35              40                  45
Glu Asp Cys Met Arg Thr Cys Gly Gly Ala
    50                  55
```

( 2 ) INFORMATION FOR SEQ ID NO: 130:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 130:

```
Arg Pro Asp Phe Cys Leu Glu Pro Pro Tyr Ser Gly Leu Cys Arg Ala
1                5                   10                  15
Leu His Lys Arg Tyr Phe Tyr Asn Ala Lys Ala Gly Leu Cys Gln Thr
                20                  25                  30
Phe Tyr Tyr Gly Gly Cys Tyr Ala Lys Arg Asn Asn Phe Glu Ser Ala
            35              40                  45
Glu Asp Cys Met Arg Thr Cys Gly Gly Ala
    50                  55
```

( 2 ) INFORMATION FOR SEQ ID NO: 131:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 131:

```
Arg Pro Asp Phe Cys Leu Glu Pro Pro Tyr Glu Gly Trp Cys Arg Ala
1               5                   10                  15
Leu His His Arg Tyr Phe Tyr Asn Ala Lys Ala Gly Leu Cys Gln Thr
                20                  25              30
Phe Ile Tyr Gly Gly Cys Gly Ala Lys Arg Asn Asn Phe Glu Ser Ala
        35              40                  45
Glu Asp Cys Met Arg Thr Cys Gly Gly Ala
    50              55
```

(2) INFORMATION FOR SEQ ID NO: 132:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 132:

```
Arg Pro Asp Phe Cys Leu Glu Pro Pro Tyr Glu Gly Phe Cys Arg Ala
1               5                   10                  15
His Phe Lys Arg Tyr Phe Tyr Asn Ala Lys Ala Gly Leu Cys Gln Ser
                20                  25              30
Phe Val Tyr Gly Gly Cys Phe Ala Lys Arg Asn Asn Phe Glu Ser Ala
        35              40                  45
Glu Asp Cys Met Arg Thr Cys Gly Gly Ala
    50              55
```

(2) INFORMATION FOR SEQ ID NO: 133:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 133:

```
Arg Pro Asp Phe Cys Leu Glu Pro Pro Tyr Glu Gly Phe Cys Arg Ala
1               5                   10                  15
Tyr Phe Lys Arg Tyr Phe Tyr Asn Ala Lys Ala Gly Leu Cys Gln Thr
                20                  25              30
Phe Thr Tyr Gly Gly Cys Phe Ala Lys Arg Asn Asn Phe Glu Ser Ala
        35              40                  45
Glu Asp Cys Met Arg Thr Cys Gly Gly Ala
    50              55
```

(2) INFORMATION FOR SEQ ID NO: 134:

(i) SEQUENCE CHARACTERISTICS:
  (A) LENGTH: 58 amino acids
  (B) TYPE: amino acid
  (C) STRANDEDNESS: single
  (D) TOPOLOGY: linear ( i i ) MOLECULE TYPE: peptide ( x i ) SEQUENCE DESCRIPTION: SEQ ID NO: 134:

| Arg | Pro | Asp | Phe | Cys | Leu | Glu | Pro | Pro | Tyr | Thr | Gly | His | Cys | Arg | Ala |
|---|---|---|---|---|---|---|---|---|---|---|---|---|---|---|---|
| 1 | | | | 5 | | | | | 10 | | | | | 15 | |

| Tyr | Phe | Lys | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Ile | Tyr | Gly | Gly | Cys | Phe | Ala | Lys | Arg | Asn | Asn | Phe | Glu | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO: 135:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 135:

| Arg | Pro | Asp | Phe | Cys | Leu | Glu | Pro | Pro | His | Ser | Gly | Ile | Cys | Arg | Ala |
|---|---|---|---|---|---|---|---|---|---|---|---|---|---|---|---|
| 1 | | | | 5 | | | | | 10 | | | | | 15 | |

| Tyr | Phe | Lys | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Phe | Ala | Lys | Arg | Asn | Asn | Phe | Glu | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO: 136:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 136:

| Arg | Pro | Asp | Phe | Cys | Leu | Glu | Pro | Pro | Tyr | Val | Gly | Phe | Cys | Arg | Ala |
|---|---|---|---|---|---|---|---|---|---|---|---|---|---|---|---|
| 1 | | | | 5 | | | | | 10 | | | | | 15 | |

| Tyr | Tyr | Ile | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Phe | Ala | Lys | Arg | Asn | Asn | Phe | Glu | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO: 137:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( x i ) SEQUENCE DESCRIPTION: SEQ ID NO: 137:

GAAGTAGCGG GTAATATAAG CCCGGCATAT GCCGGTATAC GG    42

( 2 ) INFORMATION FOR SEQ ID NO: 138:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 138:

GCTTTGCAAG GCAGCCACC 19

( 2 ) INFORMATION FOR SEQ ID NO: 139:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO: 139:

CCTCGGCCGA TTCGAAATTG TTAC 24

( 2 ) INFORMATION FOR SEQ ID NO: 140:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 140:

CCGGCATATG CCCTCATACG GTGGC 25

( 2 ) INFORMATION FOR SEQ ID NO: 141:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 141:

TTATTCGAAA CGATGTTCTC T 21

( 2 ) INFORMATION FOR SEQ ID NO: 142:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 142:

GTCTTCGCTC GAGAATTCCC CGGGATCCTT AGACAT 36

( 2 ) INFORMATION FOR SEQ ID NO: 143:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 143:

Ala Pro Asp Phe Cys Leu Glu Pro Pro Tyr Thr Gly Ile Cys Arg Ala
              5                      10                  15

Tyr Ile Thr Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
        50              55

( 2 ) INFORMATION FOR SEQ ID NO: 144:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 144:

Ala Pro Asp Phe Cys Leu Glu Pro Pro Tyr Thr Gly Ile Cys Arg Ala
                5                   10                  15

Tyr Ile Thr Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Lys Ser Ala
            35                  40                  45

Glu Asp Cys Met Arg Thr Cys Gly Gly Ala
        50              55

( 2 ) INFORMATION FOR SEQ ID NO: 145:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 145:

Ala Pro Asp Phe Cys Leu Glu Pro Pro Tyr Thr Gly Pro Cys Arg Ala
                5                   10                  15

Tyr Ile Thr Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
        50              55

( 2 ) INFORMATION FOR SEQ ID NO: 146:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 146:

Ala Pro Asp Phe Cys Leu Glu Pro Pro Tyr Thr Gly Ile Cys Arg Ala
                5                   10                  15

Tyr Ile Thr Arg Tyr Phe Tyr Asn Ala Lys Ala Gly Leu Cys Gln Arg
            20                  25                  30

Phe Val Tyr Gly Gly Cys Leu Ala Lys Arg Asn Asn Phe Glu Ser Ala (2) INFORMATION FOR SEQ ID NO: 147:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 147:

```
Ala Pro Asp Phe Cys Leu Glu Pro Pro Tyr Glu Gly Ile Cys Arg Ala
                  5                  10                  15
Tyr Ile Thr Arg Tyr Phe Tyr Asn Ala Lys Ala Gly Leu Cys Gln Arg
                 20                  25                  30
Phe Val Tyr Gly Gly Cys Leu Ala Lys Arg Asn Asn Phe Glu Ser Ala
                 35                  40                  45
Glu Asp Cys Met Arg Thr Cys Gly Gly Ala
50                  55
```

(2) INFORMATION FOR SEQ ID NO: 148:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 148:

```
Ala Pro Asp Phe Cys Leu Glu Pro Pro Tyr Thr Gly Ile Cys Arg Ala
                  5                  10                  15
Arg Ile Thr Arg Tyr Phe Tyr Asn Ala Lys Ala Gly Leu Cys Gln Thr
                 20                  25                  30
Phe Val Tyr Gly Gly Cys Leu Ala Lys Arg Asn Asn Phe Lys Ser Ala
                 35                  40                  45
Glu Asp Cys Met Arg Thr Cys Gly Gly Ala
50                  55
```

(2) INFORMATION FOR SEQ ID NO: 149:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 149:

```
Ala Pro Asp Phe Cys Leu Glu Pro Pro Tyr Thr Gly Phe Cys Arg Ala
                  5                  10                  15
Tyr Ile Thr Arg Tyr Phe Tyr Asn Ala Lys Ala Gly Leu Cys Gln Thr
                 20                  25                  30
Phe Val Tyr Gly Gly Cys Leu Ala Lys Arg Asn Asn Phe Lys Ser Ala
                 35                  40                  45
Glu Asp Cys Met Arg Thr Cys Gly Gly Ala
50                  55
```

( 2 ) INFORMATION FOR SEQ ID NO: 150:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 150:

```
Ala Pro Asp Phe Cys Leu Glu Pro Pro Tyr Thr Gly Ile Cys Arg Ala
                 5                  10                  15
Tyr Ile Thr Arg Tyr Phe Tyr Asn Ala Lys Ala Gly Leu Cys Gln Thr
             20                  25                  30
Phe Val Tyr Gly Gly Cys Phe Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 151:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 151:

```
Ala Pro Asp Phe Cys Leu Glu Pro Pro Tyr Thr Gly Ile Cys Arg Ala
                 5                  10                  15
Phe Ile Thr Arg Tyr Phe Tyr Asn Ala Lys Ala Gly Leu Cys Gln Thr
             20                  25                  30
Phe Val Tyr Gly Gly Cys Leu Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 152:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 152:

```
Ala Pro Asp Phe Cys Leu Glu Pro Pro Tyr Thr Gly Pro Cys Arg Ala
                 5                  10                  15
Tyr Ile Thr Arg Tyr Phe Tyr Asn Ala Lys Ala Gly Leu Cys Gln Thr
             20                  25                  30
Phe Val Tyr Gly Gly Cys Tyr Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 153:

( i ) SEQUENCE CHARACTERISTICS:
        ( A ) LENGTH: 58 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 153:

Ala Pro Asp Phe Cys Leu Glu Pro Pro Tyr Thr Gly Pro Cys Arg Ala
                  5                   10                  15

Tyr Ile Thr Arg Tyr Phe Tyr Asn Ala Lys Ala Gly Leu Cys Gln Thr
            20                  25                  30

Phe Val Tyr Gly Gly Cys Ile Ala Lys Arg Asn Asn Phe Lys Ser Ala
        35              40                  45

Glu Asp Cys Met Arg Thr Cys Gly Gly Ala
    50              55

( 2 ) INFORMATION FOR SEQ ID NO: 154:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 154:

Ala Pro Asp Phe Cys Leu Glu Pro Pro Tyr Thr Gly Pro Cys Arg Ala
                  5                   10                  15

Tyr Ile Thr Arg Tyr Phe Tyr Asn Ala Lys Ala Gly Leu Cys Gln Thr
            20                  25                  30

Phe Val Tyr Gly Gly Cys Trp Ala Lys Arg Asn Asn Phe Lys Ser Ala
        35              40                  45

Glu Asp Cys Met Arg Thr Cys Gly Gly Ala
    50              55

( 2 ) INFORMATION FOR SEQ ID NO: 155:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 155:

Ala Pro Asp Phe Cys Leu Glu Pro Pro Tyr Thr Gly Pro Cys Arg Ala
                  5                   10                  15

Tyr Ile Thr Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Lys Ser Ala
        35              40                  45

Glu Asp Cys Met Arg Thr Cys Gly Gly Ala
    50              55

( 2 ) INFORMATION FOR SEQ ID NO: 156:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 156:

Ala Pro Asp Phe Cys Leu Glu Pro Pro Tyr Thr Gly Ile Cys Arg Ala
                  5                   10                  15

Tyr Ile Lys Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35                  40                  45

Glu Asp Cys Met Arg Thr Cys Gly Gly Ala
    50                  55

( 2 ) INFORMATION FOR SEQ ID NO: 157:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 157:

Ala Pro Asp Phe Cys Leu Glu Pro Pro Tyr Thr Gly Pro Cys Arg Ala
                  5                   10                  15

Tyr Ile Thr Arg Tyr Phe Tyr Asn Ala Lys Ala Gly Leu Cys Gln Thr
            20                  25                  30

Phe Val Tyr Gly Gly Cys Tyr Ala Lys Arg Asn Asn Phe Tyr Ser Ala
        35                  40                  45

Glu Asp Cys Met Arg Thr Cys Gly Gly Ala
    50                  55

( 2 ) INFORMATION FOR SEQ ID NO: 158:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 158:

Arg Pro Asp Phe Cys Leu Glu Pro Pro Tyr Thr Gly Ile Cys Arg Ala
                  5                   10                  15

Ala Phe Asn Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35                  40                  45

Glu Asp Cys Met Arg Thr Cys Gly Gly Ala
    50                  55

( 2 ) INFORMATION FOR SEQ ID NO: 159:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 159:

Arg Pro Asp Phe Cys Leu Glu Pro Pro Tyr Thr Gly Ile Cys Arg Ala
                  5                   10                  15

Ala Phe Lys Arg Tyr Phe Tyr Asn Ala Lys Ala Gly Leu Cys Gln Thr
                    20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
        50                  55

( 2 ) INFORMATION FOR SEQ ID NO: 160:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 160:

Arg Pro Asp Phe Cys Leu Glu Pro Pro Tyr Thr Gly Ile Cys Arg Ala
                5                   10                  15

Ser Phe Lys Arg Tyr Phe Tyr Asn Ala Lys Ala Gly Leu Cys Gln Thr
                    20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
        50                  55

( 2 ) INFORMATION FOR SEQ ID NO: 161:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 161:

Arg Pro Asp Phe Cys Leu Glu Pro Pro Tyr Thr Gly Ile Cys Arg Ala
                5                   10                  15

Tyr Tyr Lys Arg Tyr Phe Tyr Asn Ala Lys Ala Gly Leu Cys Gln Thr
                    20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
        50                  55

( 2 ) INFORMATION FOR SEQ ID NO: 162:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 162:

Arg Pro Asp Phe Cys Leu Glu Pro Pro Tyr Thr Gly Ile Cys Arg Ala
                5                   10                  15

Ser Phe Thr Arg Tyr Phe Tyr Asn Ala Lys Ala Gly Leu Cys Gln Thr
                    20                  25                  30

Phe Val Tyr Gly Gly Cys Leu Ala Lys Arg Asn Asn Phe Glu Ser Ala

```
                        3 5                           4 0                           4 5

Glu Asp Cys Met Arg Thr Cys Gly Gly Ala
 5 0                     5 5
```

( 2 ) INFORMATION FOR SEQ ID NO: 163:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 163:

```
Arg Pro Asp Phe Cys Leu Glu Pro Pro Tyr Pro Gly Ile Cys Arg Ala
                 5                   1 0                     1 5

Leu His Lys Arg Tyr Phe Tyr Asn Ala Lys Ala Gly Leu Cys Gln Thr
             2 0                 2 5                 3 0

Phe Tyr Tyr Gly Gly Cys Met Ala Lys Arg Asn Asn Phe Glu Ser Ala
         3 5                 4 0                 4 5

Glu Asp Cys Met Arg Thr Cys Gly Gly Ala
 5 0                     5 5
```

( 2 ) INFORMATION FOR SEQ ID NO: 164:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 164:

```
Arg Pro Asp Phe Cys Leu Glu Pro Pro Tyr Glu Gly Leu Cys Arg Ala
                 5                   1 0                     1 5

Leu His Lys Arg Tyr Phe Tyr Asn Ala Lys Ala Gly Leu Cys Gln Thr
             2 0                 2 5                 3 0

Phe Tyr Tyr Gly Gly Cys Phe Ala Lys Arg Asn Asn Phe Glu Ser Ala
         3 5                 4 0                 4 5

Glu Asp Cys Met Arg Thr Cys Gly Gly Ala
 5 0                     5 5
```

( 2 ) INFORMATION FOR SEQ ID NO: 165:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 165:

```
Arg Pro Asp Phe Cys Leu Glu Pro Pro Tyr Ser Gly Leu Cys Arg Ala
                 5                   1 0                     1 5

Leu His Lys Arg Tyr Phe Tyr Asn Ala Lys Ala Gly Leu Cys Gln Thr
             2 0                 2 5                 3 0

Phe Tyr Tyr Gly Gly Cys Phe Ala Lys Arg Asn Asn Phe Glu Ser Ala
         3 5                 4 0                 4 5

Glu Asp Cys Met Arg Thr Cys Gly Gly Ala
 5 0                     5 5
```

( 2 ) INFORMATION FOR SEQ ID NO: 166:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 166:

```
Arg Pro Asp Phe Cys Leu Glu Pro Pro Tyr Ser Gly Leu Cys Arg Ala
                 5                   10                  15
Leu His Lys Arg Tyr Phe Tyr Asn Ala Lys Ala Gly Leu Cys Gln Thr
             20                  25                  30
Phe Tyr Tyr Gly Gly Cys Tyr Ala Lys Arg Asn Asn Phe Glu Ser Ala
         35                  40                  45
Glu Asp Cys Met Arg Thr Cys Gly Gly Ala
     50                  55
```

( 2 ) INFORMATION FOR SEQ ID NO: 167:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 167:

```
Arg Pro Asp Phe Cys Leu Glu Pro Pro Tyr Glu Gly Trp Cys Arg Ala
                 5                   10                  15
Leu His His Arg Tyr Phe Tyr Asn Ala Lys Ala Gly Leu Cys Gln Thr
             20                  25                  30
Phe Ile Tyr Gly Gly Cys Gly Ala Lys Arg Asn Asn Phe Glu Ser Ala
         35                  40                  45
Glu Asp Cys Met Arg Thr Cys Gly Gly Ala
     50                  55
```

( 2 ) INFORMATION FOR SEQ ID NO: 168:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 168:

```
Arg Pro Asp Phe Cys Leu Glu Pro Pro Tyr Glu Gly Phe Cys Arg Ala
                 5                   10                  15
His Phe Lys Arg Tyr Phe Tyr Asn Ala Lys Ala Gly Leu Cys Gln Ser
             20                  25                  30
Phe Val Tyr Gly Gly Cys Phe Ala Lys Arg Asn Asn Phe Glu Ser Ala
         35                  40                  45
Glu Asp Cys Met Arg Thr Cys Gly Gly Ala
     50                  55
```

( 2 ) INFORMATION FOR SEQ ID NO: 169:

( i ) SEQUENCE CHARACTERISTICS:
        ( A ) LENGTH: 58 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 169:

```
Arg Pro Asp Phe Cys Leu Glu Pro Pro Tyr Glu Gly Phe Cys Arg Ala
                 5                   10                  15
Tyr Phe Lys Arg Tyr Phe Tyr Asn Ala Lys Ala Gly Leu Cys Gln Thr
            20                  25                  30
Phe Thr Tyr Gly Gly Cys Phe Ala Lys Arg Asn Asn Phe Glu Ser Ala
        35              40                  45
Glu Asp Cys Met Arg Thr Cys Gly Gly Ala
    50                  55
```

( 2 ) INFORMATION FOR SEQ ID NO: 170:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 170:

```
Arg Pro Asp Phe Cys Leu Glu Pro Pro Tyr Thr Gly His Cys Arg Ala
                 5                   10                  15
Tyr Phe Lys Arg Tyr Phe Tyr Asn Ala Lys Ala Gly Leu Cys Gln Thr
            20                  25                  30
Phe Ile Tyr Gly Gly Cys Phe Ala Lys Arg Asn Asn Phe Glu Ser Ala
        35              40                  45
Glu Asp Cys Met Arg Thr Cys Gly Gly Ala
    50                  55
```

( 2 ) INFORMATION FOR SEQ ID NO: 171:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 171:

```
Arg Pro Asp Phe Cys Leu Glu Pro Pro His Ser Gly Ile Cys Arg Ala
                 5                   10                  15
Tyr Phe Lys Arg Tyr Phe Tyr Asn Ala Lys Ala Gly Leu Cys Gln Thr
            20                  25                  30
Phe Val Tyr Gly Gly Cys Phe Ala Lys Arg Asn Asn Phe Glu Ser Ala
        35              40                  45
Glu Asp Cys Met Arg Thr Cys Gly Gly Ala
    50                  55
```

( 2 ) INFORMATION FOR SEQ ID NO: 172:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 172:

Arg Pro Asp Phe Cys Leu Glu Pro Pro Tyr Val Gly Phe Cys Arg Ala
                  5                   10                  15

Tyr Tyr Ile Arg Tyr Phe Tyr Asn Ala Lys Ala Gly Leu Cys Gln Thr
                20              25                  30

Phe Val Tyr Gly Gly Cys Phe Ala Lys Arg Asn Asn Phe Glu Ser Ala
            35              40                  45

Glu Asp Cys Met Arg Thr Cys Gly Gly Ala
50                      55

( 2 ) INFORMATION FOR SEQ ID NO: 173:

( i ) SEQUENCE CHARACTERISTICS:
        ( A ) LENGTH: 79
        ( B ) TYPE: nucleic acid
        ( C ) STRANDEDNESS: single
        ( D ) TOPOLOGY: linear ( x i ) SEQUENCE DESCRIPTION: SEQ ID NO: 173:

GGTCTGACAG AGACCGGCCT TGGCGTTGTG TCTTCGGTTA ATTTAAATGC GCAGAAGACC    60

CGGTATACGG TGGCTCGAG                                                 79

( 2 ) INFORMATION FOR SEQ ID NO: 174:

( i ) SEQUENCE CHARACTERISTICS:
        ( A ) LENGTH: 172
        ( B ) TYPE: nucleic acid
        ( C ) STRANDEDNESS: single
        ( D ) TOPOLOGY: linear ( x i ) SEQUENCE DESCRIPTION: SEQ ID NO: 174:

GCTCCGGACT TCTGTCTCGA GCCACCGTAT ACCGGGTCTT CTGCGCATTT AAATTAACCG    60

AAGACACAAC GCCAAGGCCG GACTCTGTCA GACCTTTGTA TATGGTGGCT GCCTTGCAAA   120

GCGTAACAAT TTCGAATCGG CCGAGGACTG CATGCGTACC TGTGGTGGCG CC           172

( 2 ) INFORMATION FOR SEQ ID NO: 175:

( i ) SEQUENCE CHARACTERISTICS:
        ( A ) LENGTH: 12
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 175:

Ala Pro Asp Phe Cys Leu Glu Pro Pro Tyr Thr Gly
                  5                   10

( 2 ) INFORMATION FOR SEQ ID NO: 176:

( i ) SEQUENCE CHARACTERISTICS:
        ( A ) LENGTH: 35
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 176:

Asn Ala Lys Ala Gly Leu Cys Gln Thr Phe Val Tyr Gly Gly Cys Leu
                5                   10                  15

Ala Lys Arg Asn Asn Phe Glu Ser Ala Glu Asp Cys Met Arg Thr Cys

```
                    20                          25                          30
Gly Gly Ala
         35
```

( 2 ) INFORMATION FOR SEQ ID NO: 177:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( i x ) FEATURE: N is either of G, A, T and C; K is
            either G or T.

( x i ) SEQUENCE DESCRIPTION: SEQ ID NO: 177:

```
TACCGGCATC  TGCCGCNNKN  NKNNKNNKCG  CTACTTCTAC                              40
```

( 2 ) INFORMATION FOR SEQ ID NO: 178:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( x i ) SEQUENCE DESCRIPTION: SEQ ID NO: 178:

```
GCGGCAGATG  CC                                                             12
```

( 2 ) INFORMATION FOR SEQ ID NO: 179:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( x i ) SEQUENCE DESCRIPTION: SEQ ID NO: 179:

```
CGTTGTAGAA  GTAGCG                                                         16
```

( 2 ) INFORMATION FOR SEQ ID NO: 180:

( i ) SEQUENCE CHARACTERISTICS:
        ( A ) LENGTH: 124
        ( B ) TYPE: nucleic acid
        ( C ) STRANDEDNESS: single
        ( D ) TOPOLOGY: linear ( i x ) FEATURE:
        ( D ) OTHER INFORMATION: N is either of G, A, T and C; H is
            either of A, T and C; D is either of A,
            T and G; S is either of G and C; M is
            either of A and C; K is either of G
            and T ( x i ) SEQUENCE DESCRIPTION: SEQ ID NO: 180:

```
TCGAGCCACC  GTATNNSGGT  NNSTGCCGTG  CTMTTCATMH  SCGCTACTTC  TACAACGCCA     60

AGGCCGGTCT  CTGTCAGACC  TTTNNSTATG  GTGGCTGCNN  SGCAAAGCGT  AACAATTTCG    120

AATC                                                                     124
```

( 2 ) INFORMATION FOR SEQ ID NO: 181:

( i ) SEQUENCE CHARACTERISTICS:
        ( A ) LENGTH: 124
        ( B ) TYPE: nucleic acid
        ( C ) STRANDEDNESS: single
        ( D ) TOPOLOGY: linear ( i x ) FEATURE:
  ( D ) OTHER INFORMATION: N is either of G, A, T and C; H is
    either of A, T and C; D is either of A,
    T and G; S is either of G and C; M is
    either of A and C; K is either of G
    and T ( x i ) SEQUENCE DESCRIPTION: SEQ ID NO: 181:

GGCCGATTCG AAATTGTTAC GCTTTGCSNN GCAGCCACCA TASNNAAAGG TCTGACAGAG   60

ACCGGCCTTG GCGTTGTAGA AGTAGCGSDK ATGAAKAGCA CGGCASNNAC CSNNATACGG   120

TGGC   124

( 2 ) INFORMATION FOR SEQ ID NO: 182:

( i ) SEQUENCE CHARACTERISTICS:
    ( A ) LENGTH: 124
    ( B ) TYPE: nucleic acid
    ( C ) STRANDEDNESS: single
    ( D ) TOPOLOGY: linear ( i x ) FEATURE:
    ( D ) OTHER INFORMATION: N is either of G, A, T and C; H is
      either of A, T and C; D is either of A,
      T and G; S is either of G and C; M is
      either of A and C; Y is either of C
      and T; W is either of A and T ( x i ) SEQUENCE DESCRIPTION: SEQ ID NO: 182:

TCGAGCCACC GTATDHSGGC HHCTGCCGTG CTYWCNWCAN ACGCTACTTC TACAACGCCA   60

AGGCCGGACT CTGTCAGACC TTTNHMTATG GTGGCTGCTT SGCAAAGCGT AACAATTTCG   120

AATC   124

( 2 ) INFORMATION FOR SEQ ID NO: 183:

( i ) SEQUENCE CHARACTERISTICS:
    ( A ) LENGTH: 124
    ( B ) TYPE: nucleic acid
    ( C ) STRANDEDNESS: single
    ( D ) TOPOLOGY: linear ( i x ) FEATURE:
    ( D ) OTHER INFORMATION: N is either of G, A, T and C; H is
      either of A, T and C; D is either of A,
      T and G; S is either of G and C; M is
      either of A and C; Y is either of C
      and T; W is either of A and T ( x i ) SEQUENCE DESCRIPTION: SEQ ID NO: 183:

GGCCGATTCG AAATTGTTAC GCTTTGCSAA GCAGCCACCA TAKDNAAAGG TCTGACAGAG   60

TCCGGCCTTG GCGTTGTAGA AGTAGCGTNT GWNGWRAGCA CGGCAGDDGC CSDHATACGG   120

TGGC   124

( 2 ) INFORMATION FOR SEQ ID NO: 184:

( i ) SEQUENCE CHARACTERISTICS:
    ( A ) LENGTH: 50
    ( B ) TYPE: amino acid
    ( C ) STRANDEDNESS: single
    ( D ) TOPOLOGY: linear ( x i ) FEATURE:
    ( D ) OTHER INFORMATION: Xaa in position 7 is alanine,
      arginine, asparagine, aspartic acid, glutamic
      acid; gluamine, isoleucine, leucine,
      lysine, proline, serine, threonine,
      tryptophan, tyrosine, or valine; Xaa in
      position 9 is alanine, asparagine,
      aspartic acid, glutamine, glycine,
      histidine, isoleucine, leucine, methionine, phenylalanine, proline, serine, threonine, tryptophan, tyrosine, or valine; Xaa in position 10 is alanine, cysteine when Xaa in position 33 is cysteine, glycine or serine; Xaa in position 11 is arginine; Xaa in position 12 is alanine or glycine; Xaa in position 13 is alanine, asparagine, aspartic acid, glutamine, histidine, isoleucine, leucine, methionine, phenylalanin, proline, serine, threonine, tryptophan, tyrosine or valine; Xaa in position 14, Xaa in position 15 and Xaa in position 16 is any natural amino acid; Xaa in position 30 is alanine, arginine, asparagine, aspartic acid, cysteine, glutamic acid, glutamine, glycine, histidine, isoleucine, leucine, methionine, phenylalanine, proline, serine, threonine, tryptophan, tyrosine or valine; Xaa in position 31 is phenylalanine or tyrosine; Xaa in position 33 is alanine, cysteine when Xaa in position 10 is cysteine, glycine or serine; Xaa in position 34 is glutamine, glycine, histidine, isoleucine, leucine, lysine, methionine, phenylalanine, proline, serine, threonine, tryptophan, tyrosine or valine; Xaa in position 40 is phenylalanine or tyrosine; and Xaa in position 41 is any natural amino acid.

( x i ) SEQUENCE DESCRIPTION: SEQ ID NO: 184:

```
Cys Leu Glu Pro Pro Tyr Xaa Gly Xaa Xaa Xaa Xaa Xaa Xaa Xaa Xaa
1               5                   10                      15

Tyr Phe Tyr Asn Ala Lys Ala Gly Leu Cys Gln Thr Phe Xaa Xaa Gly
            20                  25                  30

Xaa Xaa Ala Lys Arg Asn Asn Xaa Xaa Ser Ala Glu Asp Cys Met Arg
        35              40              45

Thr Cys
    50
```

( 2 ) INFORMATION FOR SEQ ID NO: 185:

( i ) SEQUENCE CHARACTERISTICS:
        ( A ) LENGTH: 58
        ( B ) TYPE: amino acid
        ( C ) STRANDEDNESS: single
        ( D ) TOPOLOGY: linear ( i x ) FEATURE:
        ( D ) OTHER INFORMATION: Xaa in position 1 is alanine or arginine; Xaa in position 11 is alanine, arginine, aspartic acid, glutamic acid, glutamine, leucine, proline, serine, threonine or valine; Xaa in position 13 is asparagine, aspartic acid, histidine, isoleucine, leucine, methionine, phenylalanine, proline, tryptophan, tyrosine, or valine; Xaa in position 14 is cysteine; Xaa in position 15 is arginine; Xaa in position 16 is alanine or glycine; Xaa in position 17 is alanine, asparagine, histidine, isoleucine, leucine, methionine, phenylalanine, serine, tryptophan or tyrosine; Xaa in position 18 is asparagine, histidine, isoleucine, leucine, phenylalanine, tyrosine or valine; Xaa in position 19 is arginine, asparagine, glutamine, histidine, isoleucine, leucine, lysine, proline, threonine or valine; Xaa in position 20 is arginine, histidine, glutamic acid, glutamine, leucine, threonine or valine; Xaa in position 34 is alanine, glutamic acid, histidine, isoleucine, leucine, methionine, phenylalanine, serine, threonine, tryptophan, tyrosine or valine; Xaa in position 35 is phenylalanine or tyrosine; Xaa in position 38 is cysteine; Xaa in position 39 is glutamine, glycine, histidine, isoleucine, leucine, methionine, phenylalanine, serine, tryptophan, tyrosine or valine; Xaa in position 45 is phenylalanine; and Xaa in position 46 is glutamic acid, lysine or tyrosine.

( x i ) SEQUENCE DESCRIPTION: SEQ ID NO: 185:

```
Xaa Pro Asp Phe Cys Leu Glu Pro Pro Tyr Xaa Gly Xaa Xaa Xaa
                  5                   10                  15
Xaa Xaa Xaa Xaa Tyr Phe Tyr Asn Ala Lys Ala Gly Leu Cys Gln Thr
            20                  25                  30
Phe Xaa Xaa Gly Gly Xaa Xaa Ala Lys Arg Asn Asn Xaa Xaa Ser Ala
        35                  40                  45
Glu Asp Cys Met Arg Thr Cys Gly Gly Ala
    50                  55
```

( 2 ) INFORMATION FOR SEQ ID NO: 186:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 186:

```
Arg Pro Asp Phe Cys Leu Glu Pro Pro Tyr Thr Gly Ile Cys Arg Ala
                  5                   10                  15
Tyr Ile Thr Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 187:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 187:

```
Ala Pro Asp Phe Cys Leu Glu Pro Pro Tyr Thr Gly Ile Cys Arg Ala
                  5                   10                  15
Tyr Ile Thr Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 188:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 188:

| Ala | Pro | Asp | Phe | Cys<br>5 | Leu | Glu | Pro | Pro | Tyr<br>10 | Thr | Gly | Ile | Cys | Arg<br>15 | Ala |
|---|---|---|---|---|---|---|---|---|---|---|---|---|---|---|---|
| Tyr | Ile | Thr | Arg<br>20 | Tyr | Phe | Tyr | Asn | Ala<br>25 | Lys | Ala | Gly | Leu | Cys<br>30 | Gln | Thr |
| Phe | Val | Tyr<br>35 | Gly | Gly | Cys | Leu | Ala<br>40 | Lys | Arg | Asn | Asn | Phe<br>45 | Lys | Ser | Ala |
| Glu | Asp<br>50 | Cys | Met | Arg | Thr | Cys<br>55 | Gly | Gly | Ala | | | | | | |

( 2 ) INFORMATION FOR SEQ ID NO: 189:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 189:

| Ala | Pro | Asp | Phe | Cys<br>5 | Leu | Glu | Pro | Pro | Tyr<br>10 | Thr | Gly | Pro | Cys | Arg<br>15 | Ala |
|---|---|---|---|---|---|---|---|---|---|---|---|---|---|---|---|
| Tyr | Ile | Thr | Arg<br>20 | Tyr | Phe | Tyr | Asn | Ala<br>25 | Lys | Ala | Gly | Leu | Cys<br>30 | Gln | Thr |
| Phe | Val | Tyr<br>35 | Gly | Gly | Cys | Leu | Ala<br>40 | Lys | Arg | Asn | Asn | Phe<br>45 | Glu | Ser | Ala |
| Glu | Asp<br>50 | Cys | Met | Arg | Thr | Cys<br>55 | Gly | Gly | Ala | | | | | | |

( 2 ) INFORMATION FOR SEQ ID NO: 190:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 190:

| Ala | Pro | Asp | Phe | Cys<br>5 | Leu | Glu | Pro | Pro | Tyr<br>10 | Thr | Gly | Ile | Cys | Arg<br>15 | Ala |
|---|---|---|---|---|---|---|---|---|---|---|---|---|---|---|---|
| Tyr | Ile | Thr | Arg<br>20 | Tyr | Phe | Tyr | Asn | Ala<br>25 | Lys | Ala | Gly | Leu | Cys<br>30 | Gln | Arg |
| Phe | Val | Tyr<br>35 | Gly | Gly | Cys | Leu | Ala<br>40 | Lys | Arg | Asn | Asn | Phe<br>45 | Glu | Ser | Ala |
| Glu | Asp<br>50 | Cys | Met | Arg | Thr | Cys<br>55 | Gly | Gly | Ala | | | | | | |

( 2 ) INFORMATION FOR SEQ ID NO: 191:

( i ) SEQUENCE CHARACTERISTICS:

( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 191:

Ala Pro Asp Phe Cys Leu Glu Pro Pro Tyr Glu Gly Ile Cys Arg Ala
                  5                  10                 15
Tyr Ile Thr Arg Tyr Phe Tyr Asn Ala Lys Ala Gly Leu Cys Gln Arg
            20                  25                 30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
    50                  55

( 2 ) INFORMATION FOR SEQ ID NO: 192:

( i ) SEQUENCE CHARACTERISTICS:
            ( A ) LENGTH: 58 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO: 192:

Ala Pro Asp Phe Cys Leu Glu Pro Pro Tyr Thr Gly Ile Cys Arg Ala
                  5                  10                 15
Tyr Ile Ile Arg Tyr Phe Tyr Asn Ala Lys Ala Gly Leu Cys Gln Thr
            20                  25                 30
Phe Val Tyr Gly Gly Cys Leu Ala Lys Arg Asn Asn Phe Lys Ser Ala
        35                  40                  45
Glu Asp Cys Met Arg Thr Cys Gly Gly Ala
    50                  55

( 2 ) INFORMATION FOR SEQ ID NO: 193:

( i ) SEQUENCE CHARACTERISTICS:
            ( A ) LENGTH: 58 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO: 193:

Ala Pro Asp Phe Cys Leu Glu Pro Pro Tyr Thr Gly Phe Cys Arg Ala
                  5                  10                 15
Tyr Ile Thr Arg Tyr Phe Tyr Asn Ala Lys Ala Gly Leu Cys Gln Thr
            20                  25                 30
Phe Val Tyr Gly Gly Cys Leu Ala Lys Arg Asn Asn Phe Lys Ser Ala
        35                  40                  45
Glu Asp Cys Met Arg Thr Cys Gly Gly Ala
    50                  55

( 2 ) INFORMATION FOR SEQ ID NO: 194:

( i ) SEQUENCE CHARACTERISTICS:
            ( A ) LENGTH: 58 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO: 194:

| Ala | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Tyr | Ile | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Phe | Ala | Lys | Arg | Asn | Asn | Phe | Lys | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

( 2 ) INFORMATION FOR SEQ ID NO: 195:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 195:

| Ala | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Phe | Ile | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Leu | Ala | Lys | Arg | Asn | Asn | Phe | Lys | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

( 2 ) INFORMATION FOR SEQ ID NO: 196:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 196:

| Ala | Pro | Asp | Phe | Cys | Leu | Glu | Pro | Pro | Tyr | Thr | Gly | Pro | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Tyr | Ile | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Tyr | Ala | Lys | Arg | Asn | Asn | Phe | Lys | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

( 2 ) INFORMATION FOR SEQ ID NO: 197:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 197:

| Ala | Pro | Asp | Phe | Cys | Leu | Glu | Pro | Pro | Tyr | Thr | Gly | Pro | Cys | Arg | Ala |

```
                            5                              10                             15
Tyr  Ile  Thr  Arg  Tyr  Phe  Tyr  Asn  Ala  Lys  Ala  Gly  Leu  Cys  Gln  Thr
               20                        25                        30

Phe  Val  Tyr  Gly  Gly  Cys  Ile  Ala  Lys  Arg  Asn  Asn  Phe  Lys  Ser  Ala
               35                        40                        45

Glu  Asp  Cys  Met  Arg  Thr  Cys  Gly  Gly  Ala
     50                        55
```

( 2 ) INFORMATION FOR SEQ ID NO: 198:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 198:

```
Ala  Pro  Asp  Phe  Cys  Leu  Glu  Pro  Pro  Tyr  Thr  Gly  Pro  Cys  Arg  Ala
               5                         10                        15

Tyr  Ile  Thr  Arg  Tyr  Phe  Tyr  Asn  Ala  Lys  Ala  Gly  Leu  Cys  Gln  Thr
               20                        25                        30

Phe  Val  Tyr  Gly  Gly  Cys  Trp  Ala  Lys  Arg  Asn  Asn  Phe  Lys  Ser  Ala
               35                        40                        45

Glu  Asp  Cys  Met  Arg  Thr  Cys  Gly  Gly  Ala
     50                        55
```

( 2 ) INFORMATION FOR SEQ ID NO: 199:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 199:

```
Ala  Pro  Asp  Phe  Cys  Leu  Glu  Pro  Pro  Tyr  Thr  Gly  Pro  Cys  Arg  Ala
               5                         10                        15

Tyr  Ile  Thr  Arg  Tyr  Phe  Tyr  Asn  Ala  Lys  Ala  Gly  Leu  Cys  Gln  Thr
               20                        25                        30

Phe  Val  Tyr  Gly  Gly  Cys  Phe  Ala  Lys  Arg  Asn  Asn  Phe  Lys  Ser  Ala
               35                        40                        45

Glu  Asp  Cys  Met  Arg  Thr  Cys  Gly  Gly  Ala
     50                        55
```

( 2 ) INFORMATION FOR SEQ ID NO: 200:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 200:

```
Ala  Pro  Asp  Phe  Cys  Leu  Glu  Pro  Pro  Tyr  Thr  Gly  Pro  Cys  Arg  Ala
               5                         10                        15

Tyr  Ile  Thr  Arg  Tyr  Phe  Tyr  Asn  Ala  Lys  Ala  Gly  Leu  Cys  Gln  Thr
               20                        25                        30
```

Phe Val Tyr Gly Gly Cys His Ala Lys Arg Asn Asn Phe Lys Ser Ala
        35                      40                          45

Glu Asp Cys Met Arg Thr Cys Gly Gly Ala
 50                      55

( 2 ) INFORMATION FOR SEQ ID NO: 201:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 201:

Ala Pro Asp Phe Cys Leu Glu Pro Pro Tyr Thr Gly Pro Cys Arg Ala
                 5                   10                      15

Tyr Ile Thr Arg Tyr Phe Tyr Asn Ala Lys Ala Gly Leu Cys Gln Thr
            20                      25                  30

Phe Val Tyr Gly Gly Cys Ser Ala Lys Arg Asn Asn Phe Lys Ser Ala
        35                      40                          45

Glu Asp Cys Met Arg Thr Cys Gly Gly Ala
 50                      55

( 2 ) INFORMATION FOR SEQ ID NO: 202:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 202:

Ala Pro Asp Phe Cys Leu Glu Pro Pro Tyr Thr Gly Pro Cys Arg Ala
                 5                   10                      15

Tyr Ile Thr Arg Tyr Phe Tyr Asn Ala Lys Ala Gly Leu Cys Gln Thr
            20                      25                  30

Phe Val Tyr Gly Gly Cys Val Ala Lys Arg Asn Asn Phe Lys Ser Ala
        35                      40                          45

Glu Asp Cys Met Arg Thr Cys Gly Gly Ala
 50                      55

( 2 ) INFORMATION FOR SEQ ID NO: 203:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 203:

Arg Pro Asp Phe Cys Leu Glu Pro Pro Tyr Thr Gly Pro Cys Arg Gly
                 5                   10                      15

Trp Phe Arg Gln Tyr Phe Tyr Asn Ala Lys Ala Gly Leu Cys Gln Thr
            20                      25                  30

Phe Val Tyr Gly Gly Cys Arg Ala Lys Arg Asn Asn Phe Lys Ser Ala
        35                      40                          45

Glu Asp Cys Met Arg Thr Cys Gly Gly Ala
 50                      55

( 2 ) INFORMATION FOR SEQ ID NO: 204:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 204:

```
Arg Pro Asp Phe Cys Leu Glu Pro Pro Tyr Thr Gly Ile Cys Arg Gly
                 5                  10                 15
Trp Phe Arg Gln Tyr Phe Tyr Asn Ala Lys Ala Gly Leu Cys Gln Thr
             20              25                 30
Phe Val Tyr Gly Gly Cys Leu Ala Lys Arg Asn Asn Phe Lys Ser Ala
         35              40              45
Glu Asp Cys Met Arg Thr Cys Gly Gly Ala
     50              55
```

( 2 ) INFORMATION FOR SEQ ID NO: 205:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 205:

```
Arg Pro Asp Phe Cys Leu Glu Pro Pro Tyr Glu Gly Ile Cys Arg Gly
                 5                  10                 15
Trp Phe Arg Gln Tyr Phe Tyr Asn Ala Lys Ala Gly Leu Cys Gln Thr
             20              25                 30
Phe Val Tyr Gly Gly Cys Leu Ala Lys Arg Asn Asn Phe Lys Ser Ala
         35              40              45
Glu Asp Cys Met Arg Thr Cys Gly Gly Ala
     50              55
```

( 2 ) INFORMATION FOR SEQ ID NO: 206:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 206:

```
Arg Pro Asp Phe Cys Leu Glu Pro Pro Tyr Thr Gly Pro Cys Arg Ala
                 5                  10                 15
His Ile Thr Thr Tyr Phe Tyr Asn Ala Lys Ala Gly Leu Cys Gln Thr
             20              25                 30
Phe Val Tyr Gly Gly Cys Arg Ala Lys Arg Asn Asn Phe Lys Ser Ala
         35              40              45
Glu Asp Cys Met Arg Thr Cys Gly Gly Ala
     50              55
```

( 2 ) INFORMATION FOR SEQ ID NO: 207:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 207:

| Arg | Pro | Asp | Phe | Cys | Leu | Glu | Pro | Pro | Tyr | Thr | Gly | Ile | Cys | Arg | Ala |
|---|---|---|---|---|---|---|---|---|---|---|---|---|---|---|---|
| | | | | 5 | | | | | 10 | | | | | 15 | |
| His | Ile | Thr | Thr | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Leu | Ala | Lys | Arg | Asn | Asn | Phe | Lys | Ser | Ala |
| | | | 35 | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 208:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 208:

| Arg | Pro | Asp | Phe | Cys | Leu | Glu | Pro | Pro | Tyr | Glu | Gly | Ile | Cys | Arg | Ala |
|---|---|---|---|---|---|---|---|---|---|---|---|---|---|---|---|
| | | | | 5 | | | | | 10 | | | | | 15 | |
| His | Ile | Thr | Thr | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Leu | Ala | Lys | Arg | Asn | Asn | Phe | Lys | Ser | Ala |
| | | | 35 | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 209:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 209:

| Arg | Pro | Asp | Phe | Cys | Leu | Glu | Pro | Pro | Tyr | Thr | Gly | Pro | Cys | Arg | Ala |
|---|---|---|---|---|---|---|---|---|---|---|---|---|---|---|---|
| | | | | 5 | | | | | 10 | | | | | 15 | |
| His | His | Leu | Val | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Arg | Ala | Lys | Arg | Asn | Asn | Phe | Lys | Ser | Ala |
| | | | 35 | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 210:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 210:

Arg Pro Asp Phe Cys Leu Glu Pro Pro Tyr Thr Gly Ile Cys Arg Ala
                 5                  10                      15

His His Leu Val Tyr Phe Tyr Asn Ala Lys Ala Gly Leu Cys Gln Thr
             20              25                      30

Phe Val Tyr Gly Gly Cys Leu Ala Lys Arg Asn Asn Phe Lys Ser Ala
         35              40                  45

Glu Asp Cys Met Arg Thr Cys Gly Gly Ala
    50              55

( 2 ) INFORMATION FOR SEQ ID NO: 211:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 211:

Arg Pro Asp Phe Cys Leu Glu Pro Pro Tyr Glu Gly Ile Cys Arg Ala
                 5                  10                      15

His His Leu Val Tyr Phe Tyr Asn Ala Lys Ala Gly Leu Cys Gln Thr
             20              25                      30

Phe Val Tyr Gly Gly Cys Leu Ala Lys Arg Asn Asn Phe Lys Ser Ala
         35              40                  45

Glu Asp Cys Met Arg Thr Cys Gly Gly Ala
    50              55

( 2 ) INFORMATION FOR SEQ ID NO: 212:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 212:

Arg Pro Asp Phe Cys Leu Glu Pro Pro Tyr Thr Gly Pro Cys Arg Ala
                 5                  10                      15

His His Arg Glu Tyr Phe Tyr Asn Ala Lys Ala Gly Leu Cys Gln Thr
             20              25                      30

Phe Val Tyr Gly Gly Cys Arg Ala Lys Arg Asn Asn Phe Lys Ser Ala
         35              40                  45

Glu Asp Cys Met Arg Thr Cys Gly Gly Ala
    50              55

( 2 ) INFORMATION FOR SEQ ID NO: 213:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 213:

Arg Pro Asp Phe Cys Leu Glu Pro Pro Tyr Thr Gly Ile Cys Arg Ala

|   |   |   | 5 |   |   |   |   | 10 |   |   |   |   | 15 |   |
|---|---|---|---|---|---|---|---|---|---|---|---|---|---|---|

His His Arg Glu Tyr Phe Tyr Asn Ala Lys Ala Gly Leu Cys Gln Thr
          20              25             30

Phe Val Tyr Gly Gly Cys Leu Ala Lys Arg Asn Asn Phe Lys Ser Ala
      35              40              45

Glu Asp Cys Met Arg Thr Cys Gly Gly Ala
    50             55

( 2 ) INFORMATION FOR SEQ ID NO: 214:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 214:

Arg Pro Asp Phe Cys Leu Glu Pro Pro Tyr Glu Gly Ile Cys Arg Ala
            5                  10              15

His His Arg Glu Tyr Phe Tyr Asn Ala Lys Ala Gly Leu Cys Gln Thr
          20              25             30

Phe Val Tyr Gly Gly Cys Leu Ala Lys Arg Asn Asn Phe Lys Ser Ala
      35              40              45

Glu Asp Cys Met Arg Thr Cys Gly Gly Ala
    50             55

( 2 ) INFORMATION FOR SEQ ID NO: 215:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 215:

Arg Pro Asp Phe Cys Leu Glu Pro Pro Tyr Thr Gly Pro Cys Arg Ala
            5                  10              15

His Ile Arg Gln Tyr Phe Tyr Asn Ala Lys Ala Gly Leu Cys Gln Thr
          20              25             30

Phe Val Tyr Gly Gly Cys Arg Ala Lys Arg Asn Asn Phe Lys Ser Ala
      35              40              45

Glu Asp Cys Met Arg Thr Cys Gly Gly Ala
    50             55

( 2 ) INFORMATION FOR SEQ ID NO: 216:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 216:

Arg Pro Asp Phe Cys Leu Glu Pro Pro Tyr Thr Gly Ile Cys Arg Ala
            5                  10              15

His Ile Arg Gln Tyr Phe Tyr Asn Ala Lys Ala Gly Leu Cys Gln Thr
          20              25             30

```
Phe  Val  Tyr  Gly  Gly  Cys  Leu  Ala  Lys  Arg  Asn  Asn  Phe  Lys  Ser  Ala
          35                  40                       45

Glu  Asp  Cys  Met  Arg  Thr  Cys  Gly  Gly  Ala
          50                  55
```

( 2 ) INFORMATION FOR SEQ ID NO: 217:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 217:

```
Arg  Pro  Asp  Phe  Cys  Leu  Glu  Pro  Pro  Tyr  Glu  Gly  Ile  Cys  Arg  Ala
                    5                        10                      15

His  Ile  Arg  Gln  Tyr  Phe  Tyr  Asn  Ala  Lys  Ala  Gly  Leu  Cys  Gln  Thr
          20                       25                            30

Phe  Val  Tyr  Gly  Gly  Cys  Leu  Ala  Lys  Arg  Asn  Asn  Phe  Lys  Ser  Ala
          35                  40                       45

Glu  Asp  Cys  Met  Arg  Thr  Cys  Gly  Gly  Ala
          50                  55
```

( 2 ) INFORMATION FOR SEQ ID NO: 218:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 218:

```
Arg  Pro  Asp  Phe  Cys  Leu  Glu  Pro  Pro  Tyr  Thr  Gly  Pro  Cys  Arg  Gly
                    5                        10                      15

His  His  Arg  Glu  Tyr  Phe  Tyr  Asn  Ala  Asn  Ala  Gly  Leu  Cys  Gln  Thr
          20                       25                            30

Phe  Val  Tyr  Gly  Gly  Cys  Arg  Ala  Lys  Arg  Asn  Asn  Phe  Lys  Ser  Ala
          35                  40                       45

Glu  Asp  Cys  Met  Arg  Thr  Cys  Gly  Gly  Ala
          50                  55
```

( 2 ) INFORMATION FOR SEQ ID NO: 219:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 219:

```
Arg  Pro  Asp  Phe  Cys  Leu  Glu  Pro  Pro  Tyr  Thr  Gly  Ile  Cys  Arg  Gly
                    5                        10                      15

His  His  Arg  Glu  Tyr  Phe  Tyr  Asn  Ala  Asn  Ala  Gly  Leu  Cys  Gln  Thr
          20                       25                            30

Phe  Val  Tyr  Gly  Gly  Cys  Leu  Ala  Lys  Arg  Asn  Asn  Phe  Lys  Ser  Ala
          35                  40                       45

Glu  Asp  Cys  Met  Arg  Thr  Cys  Gly  Gly  Ala
          50                  55
```

( 2 ) INFORMATION FOR SEQ ID NO: 220:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 220:

```
Arg Pro Asp Phe Cys Leu Glu Pro Pro Tyr Glu Gly Ile Cys Arg Gly
                  5                  10                  15
His His Arg Glu Tyr Phe Tyr Asn Ala Asn Ala Gly Leu Cys Gln Thr
             20                  25                  30
Phe Val Tyr Gly Gly Cys Leu Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 221:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 221:

```
Arg Pro Asp Phe Cys Leu Glu Pro Pro Tyr Thr Gly Pro Cys Arg Ala
                  5                  10                  15
Tyr Phe Asn Leu Tyr Phe Tyr Asn Ala Lys Ala Gly Leu Cys Gln Thr
             20                  25                  30
Phe Val Tyr Gly Gly Cys Arg Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 222:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 222:

```
Arg Pro Asp Phe Cys Leu Glu Pro Pro Tyr Thr Gly Ile Cys Arg Ala
                  5                  10                  15
Tyr Phe Asn Leu Tyr Phe Tyr Asn Ala Lys Ala Gly Leu Cys Gln Thr
             20                  25                  30
Phe Val Tyr Gly Gly Cys Leu Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO: 223:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 223:

| Arg | Pro | Asp | Phe | Cys | Leu | Glu | Pro | Pro | Tyr | Glu | Gly | Ile | Cys | Arg | Ala |
|---|---|---|---|---|---|---|---|---|---|---|---|---|---|---|---|
|  |  |  |  | 5 |  |  |  |  | 10 |  |  |  |  | 15 |  |
| Tyr | Phe | Asn | Leu | Tyr | Phe | Tyr | Asn | Ala | Lys | Ala | Gly | Leu | Cys | Gln | Thr |
|  |  |  | 20 |  |  |  | 25 |  |  |  |  | 30 |  |  |  |
| Phe | Val | Tyr | Gly | Gly | Cys | Leu | Ala | Lys | Arg | Asn | Asn | Phe | Lys | Ser | Ala |
|  |  | 35 |  |  |  |  | 40 |  |  |  |  | 45 |  |  |  |
| Glu | Asp | Cys | Met | Arg | Thr | Cys | Gly | Gly | Ala |
|  | 50 |  |  |  |  | 55 |  |  |  |

(2) INFORMATION FOR SEQ ID NO: 224:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 224:

| Arg | Pro | Asp | Phe | Cys | Leu | Glu | Pro | Pro | Tyr | Thr | Gly | Pro | Cys | Arg | Ala |
|---|---|---|---|---|---|---|---|---|---|---|---|---|---|---|---|
|  |  |  |  | 5 |  |  |  |  | 10 |  |  |  |  | 15 |  |
| His | Val | Arg | His | Tyr | Phe | Tyr | Asn | Ala | Lys | Ala | Gly | Leu | Cys | Gln | Thr |
|  |  |  | 20 |  |  |  | 25 |  |  |  |  | 30 |  |  |  |
| Phe | Val | Tyr | Gly | Gly | Cys | Arg | Ala | Lys | Arg | Asn | Asn | Phe | Lys | Ser | Ala |
|  |  | 35 |  |  |  |  | 40 |  |  |  |  | 45 |  |  |  |
| Glu | Asp | Cys | Met | Arg | Thr | Cys | Gly | Gly | Ala |
|  | 50 |  |  |  |  | 55 |  |  |  |

(2) INFORMATION FOR SEQ ID NO: 225:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 225:

| Arg | Pro | Asp | Phe | Cys | Leu | Glu | Pro | Pro | Tyr | Thr | Gly | Ile | Cys | Arg | Ala |
|---|---|---|---|---|---|---|---|---|---|---|---|---|---|---|---|
|  |  |  |  | 5 |  |  |  |  | 10 |  |  |  |  | 15 |  |
| His | Val | Arg | His | Tyr | Phe | Tyr | Asn | Ala | Lys | Ala | Gly | Leu | Cys | Gln | Thr |
|  |  |  | 20 |  |  |  | 25 |  |  |  |  | 30 |  |  |  |
| Phe | Val | Tyr | Gly | Gly | Cys | Leu | Ala | Lys | Arg | Asn | Asn | Phe | Lys | Ser | Ala |
|  |  | 35 |  |  |  |  | 40 |  |  |  |  | 45 |  |  |  |
| Glu | Asp | Cys | Met | Arg | Thr | Cys | Gly | Gly | Ala |
|  | 50 |  |  |  |  | 55 |  |  |  |

(2) INFORMATION FOR SEQ ID NO: 226:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 226:

Arg Pro Asp Phe Cys Leu Glu Pro Pro Tyr Glu Gly Ile Cys Arg Ala
                 5                  10                 15
His Val Arg His Tyr Phe Tyr Asn Ala Lys Ala Gly Leu Cys Gln Thr
             20                  25                 30
Phe Val Tyr Gly Gly Cys Leu Ala Lys Arg Asn Asn Phe Lys Ser Ala
         35                  40                  45
Glu Asp Cys Met Arg Thr Cys Gly Gly Ala
     50                  55

( 2 ) INFORMATION FOR SEQ ID NO: 227:

( i ) SEQUENCE CHARACTERISTICS:
       ( A ) LENGTH: 58 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO: 227:

Arg Pro Asp Phe Cys Leu Glu Pro Pro Tyr Thr Gly Ile Cys Arg Ala
                 5                  10                 15
Asn Phe Lys Arg Tyr Phe Tyr Asn Ala Lys Ala Gly Leu Cys Gln Thr
             20                  25                 30
Phe Val Tyr Gly Gly Cys Leu Ala Lys Arg Asn Asn Phe Glu Ser Ala
         35                  40                  45
Glu Asp Cys Met Arg Thr Cys Gly Gly Ala
     50                  55

( 2 ) INFORMATION FOR SEQ ID NO: 228:

( i ) SEQUENCE CHARACTERISTICS:
       ( A ) LENGTH: 58 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO: 228:

Arg Pro Asp Phe Cys Leu Glu Pro Pro Tyr Thr Gly Ile Cys Arg Ala
                 5                  10                 15
Ser Phe Asn Arg Tyr Phe Tyr Asn Ala Lys Ala Gly Leu Cys Gln Thr
             20                  25                 30
Phe Val Tyr Gly Gly Cys Leu Ala Lys Arg Asn Asn Phe Glu Ser Ala
         35                  40                  45
Glu Asp Cys Met Arg Thr Cys Gly Gly Ala
     50                  55

( 2 ) INFORMATION FOR SEQ ID NO: 229:

( i ) SEQUENCE CHARACTERISTICS:
       ( A ) LENGTH: 58 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO: 229:

Arg Pro Asp Phe Cys Leu Glu Pro Pro Tyr Thr Gly Ile Cys Arg Ala

Ala Phe Lys Arg Tyr Phe Tyr Asn Ala Lys Ala Gly Leu Cys Gln Thr
                20                  25                  30

Phe Val Tyr Gly Gly Cys Leu Ala Lys Arg Asn Asn Phe Glu Ser Ala
        35                  40                  45

Glu Asp Cys Met Arg Thr Cys Gly Gly Ala
    50                  55

( 2 ) INFORMATION FOR SEQ ID NO: 230:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 230:

Arg Pro Asp Phe Cys Leu Glu Pro Pro Tyr Thr Gly Ile Cys Arg Ser
                5                   10                  15

Tyr Phe Lys Arg Tyr Phe Tyr Asn Ala Lys Ala Gly Leu Cys Gln Thr
                20                  25                  30

Phe Val Tyr Gly Gly Cys Leu Ala Lys Arg Asn Asn Phe Glu Ser Ala
        35                  40                  45

Glu Asp Cys Met Arg Thr Cys Gly Gly Ala
    50                  55

( 2 ) INFORMATION FOR SEQ ID NO: 231:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 231:

Arg Pro Asp Phe Cys Leu Glu Pro Pro Tyr Thr Gly Ile Cys Arg Ala
                5                   10                  15

Ser Phe Lys Arg Tyr Phe Tyr Asn Ala Lys Ala Gly Leu Cys Gln Thr
                20                  25                  30

Phe Val Tyr Gly Gly Cys Leu Ala Lys Arg Asn Asn Phe Glu Ser Ala
        35                  40                  45

Glu Asp Cys Met Arg Thr Cys Gly Gly Ala
    50                  55

( 2 ) INFORMATION FOR SEQ ID NO: 232:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 232:

Arg Pro Asp Phe Cys Leu Glu Pro Pro Tyr Thr Gly Ile Cys Arg Ala
                5                   10                  15

His Tyr Lys Arg Tyr Phe Tyr Asn Ala Lys Ala Gly Leu Cys Gln Thr
                20                  25                  30

```
Phe Val Tyr Gly Gly Cys Leu Ala Lys Arg Asn Asn Phe Glu Ser Ala
         35                    40                        45

Glu Asp Cys Met Arg Thr Cys Gly Gly Ala
         50              55
```

( 2 ) INFORMATION FOR SEQ ID NO: 233:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 233:

```
Arg Pro Asp Phe Cys Leu Glu Pro Pro Tyr Thr Gly Ile Cys Arg Ala
                 5                   10                      15

Ser Phe Thr Arg Tyr Phe Tyr Asn Ala Lys Ala Gly Leu Cys Gln Thr
            20                   25                  30

Phe Val Tyr Gly Gly Cys Leu Ala Lys Arg Asn Asn Phe Glu Ser Ala
         35                    40                        45

Glu Asp Cys Met Arg Thr Cys Gly Gly Ala
         50              55
```

( 2 ) INFORMATION FOR SEQ ID NO: 234:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 234:

```
Arg Pro Asp Phe Cys Leu Glu Pro Pro Tyr Thr Gly Ile Cys Arg Ala
                 5                   10                      15

Ser Tyr Thr Arg Tyr Phe Tyr Asn Ala Lys Ala Gly Leu Cys Gln Thr
            20                   25                  30

Phe Val Tyr Gly Gly Cys Leu Ala Lys Arg Asn Asn Phe Glu Ser Ala
         35                    40                        45

Glu Asp Cys Met Arg Thr Cys Gly Gly Ala
         50              55
```

( 2 ) INFORMATION FOR SEQ ID NO: 235:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 235:

```
Arg Pro Asp Phe Cys Leu Glu Pro Pro Tyr Thr Gly Ile Cys Arg Ala
                 5                   10                      15

Ser Tyr Lys Arg Tyr Phe Tyr Asn Ala Lys Ala Gly Leu Cys Gln Thr
            20                   25                  30

Phe Val Tyr Gly Gly Cys Leu Ala Lys Arg Asn Asn Phe Glu Ser Ala
         35                    40                        45

Glu Asp Cys Met Arg Thr Cys Gly Gly Ala
         50              55
```

( 2 ) INFORMATION FOR SEQ ID NO: 236:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 236:

```
Arg Pro Asp Phe Cys Leu Glu Pro Pro Tyr Thr Gly Ile Cys Arg Ala
                 5                  10                     15
Met Phe His Arg Tyr Phe Tyr Asn Ala Lys Ala Gly Leu Cys Gln Thr
             20              25                      30
Phe Val Tyr Gly Gly Cys Leu Ala Lys Arg Asn Asn Phe Glu Ser Ala
         35              40                  45
Glu Asp Cys Met Arg Thr Cys Gly Gly Ala
     50              55
```

( 2 ) INFORMATION FOR SEQ ID NO: 237:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 237:

```
Arg Pro Asp Phe Cys Leu Glu Pro Pro Tyr Thr Gly Ile Cys Arg Ala
                 5                  10                     15
Ile Tyr Val Arg Tyr Phe Tyr Asn Ala Lys Ala Gly Leu Cys Gln Thr
             20              25                      30
Phe Val Tyr Gly Gly Cys Leu Ala Lys Arg Asn Asn Phe Glu Ser Ala
         35              40                  45
Glu Asp Cys Met Arg Thr Cys Gly Gly Ala
     50              55
```

( 2 ) INFORMATION FOR SEQ ID NO: 238:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 238:

```
Arg Pro Asp Phe Cys Leu Glu Pro Pro Tyr Thr Gly Ile Cys Arg Ala
                 5                  10                     15
Asn Phe Asn Arg Tyr Phe Tyr Asn Ala Lys Ala Gly Leu Cys Gln Thr
             20              25                      30
Phe Val Tyr Gly Gly Cys Leu Ala Lys Arg Asn Asn Phe Glu Ser Ala
         35              40                  45
Glu Asp Cys Met Arg Thr Cys Gly Gly Ala
     50              55
```

( 2 ) INFORMATION FOR SEQ ID NO: 239:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 239:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Tyr | Tyr | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Leu | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 240:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 240:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Ala | Phe | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Leu | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 241:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 241:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Leu | His | Ile | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Leu | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 242:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 242:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |

| Ile | Tyr | Lys | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
|     |     |     | 20  |     |     |     |     |     | 25  |     |     |     |     |     | 30  |

| Phe | Val | Tyr | Gly | Gly | Cys | Leu | Ala | Lys | Arg | Asn | Asn | Phe | Glu | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Asp | Cys | Met | Arg | Thr | Cys | Gly | Gly | Ala |
|-----|-----|-----|-----|-----|-----|-----|-----|-----|-----|
|     | 50  |     |     |     |     | 55  |     |     |     |

( 2 ) INFORMATION FOR SEQ ID NO: 243:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 243:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |

| Ala | Phe | Asn | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
|     |     |     | 20  |     |     |     |     |     | 25  |     |     |     |     |     | 30  |

| Phe | Val | Tyr | Gly | Gly | Cys | Leu | Ala | Lys | Arg | Asn | Asn | Phe | Glu | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Asp | Cys | Met | Arg | Thr | Cys | Gly | Gly | Ala |
|-----|-----|-----|-----|-----|-----|-----|-----|-----|-----|
|     | 50  |     |     |     |     | 55  |     |     |     |

( 2 ) INFORMATION FOR SEQ ID NO: 244:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 244:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |

| Phe | Tyr | Lys | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
|     |     |     | 20  |     |     |     |     |     | 25  |     |     |     |     |     | 30  |

| Phe | Val | Tyr | Gly | Gly | Cys | Leu | Ala | Lys | Arg | Asn | Asn | Phe | Glu | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Asp | Cys | Met | Arg | Thr | Cys | Gly | Gly | Ala |
|-----|-----|-----|-----|-----|-----|-----|-----|-----|-----|
|     | 50  |     |     |     |     | 55  |     |     |     |

( 2 ) INFORMATION FOR SEQ ID NO: 245:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 245:

| Arg | Pro | Asp | Phe | Cys | Leu | Glu | Pro | Pro | Tyr | Thr | Gly | Ile | Cys | Arg | Ala |
|-----|-----|-----|-----|-----|-----|-----|-----|-----|-----|-----|-----|-----|-----|-----|-----|

|   |   |   |   | 5 |   |   |   |   | 10 |   |   |   |   | 15 |   |
|---|---|---|---|---|---|---|---|---|---|---|---|---|---|---|---|

Leu Tyr Lys Arg Tyr Phe Tyr Asn Ala Lys Ala Gly Leu Cys Gln Thr
          20                    25                30

Phe Val Tyr Gly Gly Cys Leu Ala Lys Arg Asn Asn Phe Glu Ser Ala
        35                  40              45

Glu Asp Cys Met Arg Thr Cys Gly Gly Ala
    50                55

( 2 ) INFORMATION FOR SEQ ID NO: 246:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 246:

Arg Pro Asp Phe Cys Leu Glu Pro Pro Tyr Asp Gly Pro Cys Arg Ala
                5                    10              15

Leu His Leu Arg Tyr Phe Tyr Asn Ala Lys Ala Gly Leu Cys Gln Thr
          20                    25                30

Phe Tyr Tyr Gly Gly Cys Leu Ala Lys Arg Asn Asn Phe Glu Ser Ala
        35                  40              45

Glu Asp Cys Met Arg Thr Cys Gly Gly Ala
    50                55

( 2 ) INFORMATION FOR SEQ ID NO: 247:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 247:

Arg Pro Asp Phe Cys Leu Glu Pro Pro Tyr Pro Gly Tyr Cys Arg Ala
                5                    10              15

Leu His Leu Arg Tyr Phe Tyr Asn Ala Lys Ala Gly Leu Cys Gln Thr
          20                    25                30

Phe Thr Tyr Gly Gly Cys His Ala Lys Arg Asn Asn Phe Glu Ser Ala
        35                  40              45

Glu Asp Cys Met Arg Thr Cys Gly Gly Ala
    50                55

( 2 ) INFORMATION FOR SEQ ID NO: 248:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 248:

Arg Pro Asp Phe Cys Leu Glu Pro Pro Tyr Thr Gly Pro Cys Arg Ala
                5                    10              15

Leu His His Arg Tyr Phe Tyr Asn Ala Lys Ala Gly Leu Cys Gln Thr
          20                    25                30

```
Phe  Phe  Tyr  Gly  Gly  Cys  Phe  Ala  Lys  Arg  Asn  Asn  Phe  Glu  Ser  Ala
          35                       40                      45

Glu  Asp  Cys  Met  Arg  Thr  Cys  Gly  Gly  Ala
     50                       55
```

(2) INFORMATION FOR SEQ ID NO: 249:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 249:

```
Arg  Pro  Asp  Phe  Cys  Leu  Glu  Pro  Pro  Tyr  Pro  Gly  Ile  Cys  Arg  Ala
               5                        10                      15

Leu  His  Pro  Arg  Tyr  Phe  Tyr  Asn  Ala  Lys  Ala  Gly  Leu  Cys  Gln  Thr
               20                       25                      30

Phe  His  Tyr  Gly  Gly  Cys  Leu  Ala  Lys  Arg  Asn  Asn  Phe  Glu  Ser  Ala
          35                       40                      45

Glu  Asp  Cys  Met  Arg  Thr  Cys  Gly  Gly  Ala
     50                       55
```

(2) INFORMATION FOR SEQ ID NO: 250:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 250:

```
Arg  Pro  Asp  Phe  Cys  Leu  Glu  Pro  Pro  Tyr  Val  Gly  Ile  Cys  Arg  Ala
               5                        10                      15

Leu  His  Thr  Arg  Tyr  Phe  Tyr  Asn  Ala  Lys  Ala  Gly  Leu  Cys  Gln  Thr
               20                       25                      30

Phe  Ser  Tyr  Gly  Gly  Cys  Phe  Ala  Lys  Arg  Asn  Asn  Phe  Glu  Ser  Ala
          35                       40                      45

Glu  Asp  Cys  Met  Arg  Thr  Cys  Gly  Gly  Ala
     50                       55
```

(2) INFORMATION FOR SEQ ID NO: 251:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 251:

```
Arg  Pro  Asp  Phe  Cys  Leu  Glu  Pro  Pro  Tyr  Ser  Gly  Leu  Cys  Arg  Ala
               5                        10                      15

Leu  His  Lys  Arg  Tyr  Phe  Tyr  Asn  Ala  Lys  Ala  Gly  Leu  Cys  Gln  Thr
               20                       25                      30

Phe  Tyr  Tyr  Gly  Gly  Cys  Tyr  Ala  Lys  Arg  Asn  Asn  Phe  Glu  Ser  Ala
          35                       40                      45

Glu  Asp  Cys  Met  Arg  Thr  Cys  Gly  Gly  Ala
     50                       55
```

( 2 ) INFORMATION FOR SEQ ID NO: 252:

( i ) SEQUENCE CHARACTERISTICS:
　　　　　　　　( A ) LENGTH: 58 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: peptide ( x i ) SEQUENCE DESCRIPTION: SEQ ID NO: 252:

Arg Pro Asp Phe Cys Leu Glu Pro Pro Tyr Leu Gly Ile Cys Arg Ala
                  5                  10                 15

Leu His Thr Arg Tyr Phe Tyr Asn Ala Lys Ala Gly Leu Cys Gln Thr
             20                  25                 30

Phe Ser Tyr Gly Gly Cys Leu Ala Lys Arg Asn Asn Phe Glu Ser Ala
         35              40                  45

Glu Asp Cys Met Arg Thr Cys Gly Gly Ala
     50                  55

( 2 ) INFORMATION FOR SEQ ID NO: 253:

( i ) SEQUENCE CHARACTERISTICS:
　　　　　　　　( A ) LENGTH: 58 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: peptide ( x i ) SEQUENCE DESCRIPTION: SEQ ID NO: 253:

Arg Pro Asp Phe Cys Leu Glu Pro Pro Tyr Pro Gly Ile Cys Arg Ala
                  5                  10                 15

Leu His Lys Arg Tyr Phe Tyr Asn Ala Lys Ala Gly Leu Cys Gln Thr
             20                  25                 30

Phe His Tyr Gly Gly Cys Phe Ala Lys Arg Asn Asn Phe Glu Ser Ala
         35              40                  45

Glu Asp Cys Met Arg Thr Cys Gly Gly Ala
     50                  55

( 2 ) INFORMATION FOR SEQ ID NO: 254:

( i ) SEQUENCE CHARACTERISTICS:
　　　　　　　　( A ) LENGTH: 58 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: peptide ( x i ) SEQUENCE DESCRIPTION: SEQ ID NO: 254:

Arg Pro Asp Phe Cys Leu Glu Pro Pro Tyr Ser Gly Leu Cys Arg Ala
                  5                  10                 15

Leu His Lys Arg Tyr Phe Tyr Asn Ala Lys Ala Gly Leu Cys Gln Thr
             20                  25                 30

Phe Tyr Tyr Gly Gly Cys Phe Ala Lys Arg Asn Asn Phe Glu Ser Ala
         35              40                  45

Glu Asp Cys Met Arg Thr Cys Gly Gly Ala
     50                  55

( 2 ) INFORMATION FOR SEQ ID NO: 255:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 255:

| Arg | Pro | Asp | Phe | Cys | Leu | Glu | Pro | Pro | Tyr | Pro | Gly | Ile | Cys | Arg | Ala |
|---|---|---|---|---|---|---|---|---|---|---|---|---|---|---|---|
| | | | | 5 | | | | | 10 | | | | | 15 | |
| Leu | His | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Tyr | Tyr | Gly | Gly | Cys | Met | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala |
| | 50 | | | | | 55 | | | |

(2) INFORMATION FOR SEQ ID NO: 256:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 256:

| Arg | Pro | Asp | Phe | Cys | Leu | Glu | Pro | Pro | Tyr | Glu | Gly | Met | Cys | Arg | Ala |
|---|---|---|---|---|---|---|---|---|---|---|---|---|---|---|---|
| | | | | 5 | | | | | 10 | | | | | 15 | |
| Ile | His | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Thr | Tyr | Gly | Gly | Cys | Met | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala |
| | 50 | | | | | 55 | | | |

(2) INFORMATION FOR SEQ ID NO: 257:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 257:

| Arg | Pro | Asp | Phe | Cys | Leu | Glu | Pro | Pro | Tyr | Pro | Gly | Val | Cys | Arg | Ala |
|---|---|---|---|---|---|---|---|---|---|---|---|---|---|---|---|
| | | | | 5 | | | | | 10 | | | | | 15 | |
| Leu | His | Lys | Arg | Tyr | Phe | Tyr | Asn | Ala | Lys | Ala | Gly | Leu | Cys | Gln | Thr |
| | | | 20 | | | | | 25 | | | | | 30 | | |
| Phe | Ser | Tyr | Gly | Gly | Cys | Gln | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala |
| | 50 | | | | | 55 | | | |

(2) INFORMATION FOR SEQ ID NO: 258:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 258:

```
Arg Pro Asp Phe Cys Leu Glu Pro Pro Tyr Arg Gly Val Cys Arg Ala
                  5                   10                  15

Ile His Lys Arg Tyr Phe Tyr Asn Ala Lys Ala Gly Leu Cys Gln Thr
                20                  25                  30

Phe Leu Tyr Gly Gly Cys Met Ala Lys Arg Asn Asn Phe Glu Ser Ala
            35                  40                  45

Glu Asp Cys Met Arg Thr Cys Gly Gly Ala
        50                  55
```

( 2 ) INFORMATION FOR SEQ ID NO: 259:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 259:

```
Arg Pro Asp Phe Cys Leu Glu Pro Pro Tyr Pro Gly Leu Cys Arg Ala
                  5                   10                  15

Leu His Lys Arg Tyr Phe Tyr Asn Ala Lys Ala Gly Leu Cys Gln Thr
                20                  25                  30

Phe Tyr Tyr Gly Gly Cys Tyr Ala Lys Arg Asn Asn Phe Glu Ser Ala
            35                  40                  45

Glu Asp Cys Met Arg Thr Cys Gly Gly Ala
        50                  55
```

( 2 ) INFORMATION FOR SEQ ID NO: 260:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 260:

```
Arg Pro Asp Phe Cys Leu Glu Pro Pro Tyr Ala Gly Tyr Cys Arg Ala
                  5                   10                  15

Leu His Lys Arg Tyr Phe Tyr Asn Ala Lys Ala Gly Leu Cys Gln Thr
                20                  25                  30

Phe Tyr Tyr Gly Gly Cys Phe Ala Lys Arg Asn Asn Phe Glu Ser Ala
            35                  40                  45

Glu Asp Cys Met Arg Thr Cys Gly Gly Ala
        50                  55
```

( 2 ) INFORMATION FOR SEQ ID NO: 261:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 261:

```
Arg Pro Asp Phe Cys Leu Glu Pro Pro Tyr Arg Gly Val Cys Arg Ala
```

Ile His Gln Arg Tyr Phe Tyr Asn Ala Lys Ala Gly Leu Cys Gln Thr
                20                  25                  30

Phe Ile Tyr Gly Gly Cys Met Ala Lys Arg Asn Asn Phe Glu Ser Ala
            35                  40                  45

Glu Asp Cys Met Arg Thr Cys Gly Gly Ala
        50              55

( 2 ) INFORMATION FOR SEQ ID NO: 262:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 262:

Arg Pro Asp Phe Cys Leu Glu Pro Pro Tyr Thr Gly Tyr Cys Arg Ala
                5                   10                  15

Leu His Lys Arg Tyr Phe Tyr Asn Ala Lys Ala Gly Leu Cys Gln Thr
                20                  25                  30

Phe Tyr Tyr Gly Gly Cys Phe Ala Lys Arg Asn Asn Phe Glu Ser Ala
            35                  40                  45

Glu Asp Cys Met Arg Thr Cys Gly Gly Ala
        50              55

( 2 ) INFORMATION FOR SEQ ID NO: 263:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 263:

Arg Pro Asp Phe Cys Leu Glu Pro Pro Tyr Thr Gly Ile Cys Arg Ala
                5                   10                  15

Leu His Lys Arg Tyr Phe Tyr Asn Ala Lys Ala Gly Leu Cys Gln Thr
                20                  25                  30

Phe Trp Tyr Gly Gly Cys Leu Ala Lys Arg Asn Asn Phe Glu Ser Ala
            35                  40                  45

Glu Asp Cys Met Arg Thr Cys Gly Gly Ala
        50              55

( 2 ) INFORMATION FOR SEQ ID NO: 264:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 264:

Arg Pro Asp Phe Cys Leu Glu Pro Pro Tyr Gln Gly Ile Cys Arg Ala
                5                   10                  15

Leu His Lys Arg Tyr Phe Tyr Asn Ala Lys Ala Gly Leu Cys Gln Thr
                20                  25                  30

```
Phe Met Tyr Gly Gly Cys Leu Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 265:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 265:

```
Arg Pro Asp Phe Cys Leu Glu Pro Pro Tyr Pro Gly Ile Cys Arg Ala
                5                   10                      15

Leu His Lys Arg Tyr Phe Tyr Asn Ala Lys Ala Gly Leu Cys Gln Thr
            20                  25                  30

Phe Tyr Tyr Gly Gly Cys Met Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 266:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 266:

```
Arg Pro Asp Phe Cys Leu Glu Pro Pro Tyr Glu Gly Leu Cys Arg Ala
                5                   10                      15

Leu His Lys Arg Tyr Phe Tyr Asn Ala Lys Ala Gly Leu Cys Gln Thr
            20                  25                  30

Phe Tyr Tyr Gly Gly Cys Phe Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 267:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 267:

```
Arg Pro Asp Phe Cys Leu Glu Pro Pro Tyr Glu Gly Phe Cys Arg Ala
                5                   10                      15

Tyr Phe Lys Arg Tyr Phe Tyr Asn Ala Lys Ala Gly Leu Cys Gln Thr
            20                  25                  30

Phe Thr Tyr Gly Gly Cys Phe Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 268:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 268:

```
Arg Pro Asp Phe Cys Leu Glu Pro Pro Tyr Val Gly Asp Cys Arg Ala
                  5                  10                 15
Tyr Phe Lys Arg Tyr Phe Tyr Asn Ala Lys Ala Gly Leu Cys Gln Thr
             20                  25                 30
Phe Val Phe Gly Gly Cys Leu Ala Lys Arg Asn Asn Phe Glu Ser Ala
         35                  40                 45
Glu Asp Cys Met Arg Thr Cys Gly Gly Ala
 50                  55
```

( 2 ) INFORMATION FOR SEQ ID NO: 269:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 269:

```
Arg Pro Asp Phe Cys Leu Glu Pro Pro Tyr Glu Gly Phe Cys Arg Ala
                  5                  10                 15
His Phe Lys Arg Tyr Phe Tyr Asn Ala Lys Ala Gly Leu Cys Gln Ser
             20                  25                 30
Phe Val Tyr Gly Gly Cys Phe Ala Lys Arg Asn Asn Phe Glu Ser Ala
         35                  40                 45
Glu Asp Cys Met Arg Thr Cys Gly Gly Ala
 50                  55
```

( 2 ) INFORMATION FOR SEQ ID NO: 270:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 270:

```
Arg Pro Asp Phe Cys Leu Glu Pro Ala Tyr Glu Gly Tyr Cys Arg Ala
                  5                  10                 15
Tyr Ile Lys Arg Tyr Phe Phe Asn Ala Lys Ala Gly Leu Cys Gln Thr
             20                  25                 30
Phe His Tyr Gly Gly Cys Phe Ala Lys Arg Asn Asn Phe Glu Ser Ala
         35                  40                 45
Glu Asp Cys Met Arg Thr Cys Gly Gly Ala
 50                  55
```

( 2 ) INFORMATION FOR SEQ ID NO: 271:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 271:

| Arg | Pro | Asp | Phe | Cys | Leu | Glu | Pro | Pro | Tyr | Thr | Gly | His | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Phe | Phe | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 272:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 272:

| Arg | Pro | Asp | Phe | Cys | Leu | Glu | Pro | Pro | Tyr | Thr | Gly | His | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Tyr | Phe | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Ile | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 273:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 273:

| Arg | Pro | Asp | Phe | Cys | Leu | Glu | Pro | Ala | Tyr | Glu | Gly | Phe | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Tyr | Phe | Ile | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Val | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 274:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 274:

| Arg | Pro | Asp | Phe | Cys | Leu | Glu | Pro | Pro | His | Ser | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |
| Tyr | Phe | Thr | Arg | Tyr | Phe | Tyr | Asn | Ala | Lys | Ala | Gly | Leu | Cys | Gln | Thr |
|     |     |     | 20  |     |     |     |     |     | 25  |     |     |     |     | 30  |     |
| Phe | His | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

( 2 ) INFORMATION FOR SEQ ID NO: 275:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 275:

| Arg | Pro | Asp | Phe | Cys | Leu | Glu | Pro | Pro | Tyr | Glu | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |
| Leu | Phe | Thr | Arg | Tyr | Phe | Tyr | Asn | Ala | Lys | Ala | Gly | Leu | Cys | Gln | Thr |
|     |     |     | 20  |     |     |     |     |     | 25  |     |     |     |     | 30  |     |
| Phe | His | Tyr | Gly | Gly | Cys | Leu | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

( 2 ) INFORMATION FOR SEQ ID NO: 276:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 276:

| Arg | Pro | Asp | Phe | Cys | Leu | Glu | Pro | Pro | Ser | Glu | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |
| Tyr | His | Lys | Arg | Tyr | Phe | Tyr | Asn | Ala | Lys | Ala | Gly | Leu | Cys | Gln | Thr |
|     |     |     | 20  |     |     |     |     |     | 25  |     |     |     |     | 30  |     |
| Phe | Val | Tyr | Gly | Gly | Cys | Leu | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

( 2 ) INFORMATION FOR SEQ ID NO: 277:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 277:

| Arg | Pro | Asp | Phe | Cys | Leu | Glu | Pro | Pro | Tyr | Glu | Gly | Asn | Cys | Arg | Ala |
|-----|-----|-----|-----|-----|-----|-----|-----|-----|-----|-----|-----|-----|-----|-----|-----|

```
Phe  Phe  Arg  Arg  Tyr  Phe  Tyr  Asn  Ala  Lys  Ala  Gly  Leu  Cys  Gln  Thr
               20                  25                       30

Phe  Ile  Tyr  Gly  Gly  Cys  Leu  Ala  Lys  Arg  Asn  Asn  Phe  Glu  Ser  Ala
          35                  40                       45

Glu  Asp  Cys  Met  Arg  Thr  Cys  Gly  Gly  Ala
     50                       55
```

( 2 ) INFORMATION FOR SEQ ID NO: 278:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 278:

```
Arg  Pro  Asp  Phe  Cys  Leu  Glu  Pro  Pro  Tyr  Leu  Gly  Ile  Cys  Arg  Ala
                    5                        10                       15

Tyr  Leu  Lys  Arg  Tyr  Phe  Tyr  Asn  Ala  Lys  Ala  Gly  Leu  Cys  Gln  Thr
               20                  25                       30

Phe  Tyr  Tyr  Gly  Gly  Cys  Leu  Ala  Lys  Arg  Asn  Asn  Phe  Glu  Ser  Ala
          35                  40                       45

Glu  Asp  Cys  Met  Arg  Thr  Cys  Gly  Gly  Ala
     50                       55
```

( 2 ) INFORMATION FOR SEQ ID NO: 279:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 279:

```
Arg  Pro  Asp  Phe  Cys  Leu  Glu  Pro  Pro  Tyr  Glu  Gly  Asn  Cys  Arg  Ala
                    5                        10                       15

Tyr  Leu  Lys  Arg  Tyr  Phe  Tyr  Asn  Ala  Lys  Ala  Gly  Leu  Cys  Gln  Thr
               20                  25                       30

Phe  Ala  Tyr  Gly  Gly  Cys  Phe  Ala  Lys  Arg  Asn  Asn  Phe  Glu  Ser  Ala
          35                  40                       45

Glu  Asp  Cys  Met  Arg  Thr  Cys  Gly  Gly  Ala
     50                       55
```

( 2 ) INFORMATION FOR SEQ ID NO: 280:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 280:

```
Arg  Pro  Asp  Phe  Cys  Leu  Glu  Pro  Pro  Tyr  Glu  Gly  Ile  Cys  Arg  Ala
                    5                        10                       15

Tyr  Phe  Lys  Arg  Tyr  Phe  Tyr  Asn  Ala  Lys  Ala  Gly  Leu  Cys  Gln  Thr
               20                  25                       30
```

Phe Ser Tyr Gly Gly Cys Phe Ala Lys Arg Asn Asn Phe Glu Ser Ala
     35                  40                     45

Glu Asp Cys Met Arg Thr Cys Gly Gly Ala
    50                  55

( 2 ) INFORMATION FOR SEQ ID NO: 281:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 281:

Arg Pro Asp Phe Cys Leu Glu Pro Pro Tyr Glu Gly Ile Cys Arg Ala
                 5                  10                     15

Phe Asn Lys Arg Tyr Phe Tyr Asn Ala Lys Ala Gly Leu Cys Gln Thr
             20                  25                  30

Phe Val Tyr Gly Gly Cys Leu Ala Lys Arg Asn Asn Phe Glu Ser Ala
         35                  40                     45

Glu Asp Cys Met Arg Thr Cys Gly Gly Ala
    50                  55

( 2 ) INFORMATION FOR SEQ ID NO: 282:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 282:

Arg Pro Asp Phe Cys Leu Glu Ser Pro Tyr Ala Gly Ile Cys Arg Ala
                 5                  10                     15

Tyr Ile Lys Arg Tyr Phe Tyr Asn Ala Lys Ala Gly Leu Cys Gln Thr
             20                  25                  30

Phe Tyr Tyr Gly Gly Cys Phe Ala Lys Arg Asn Asn Phe Glu Ser Ala
         35                  40                     45

Glu Asp Cys Met Arg Thr Cys Gly Gly Ala
    50                  55

( 2 ) INFORMATION FOR SEQ ID NO: 283:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 283:

Arg Pro Asp Phe Cys Leu Glu Pro Pro Tyr Glu Gly Ile Cys Arg Ala
                 5                  10                     15

Leu His Lys Arg Tyr Phe Tyr Asn Ala Lys Ala Gly Leu Cys Gln Thr
             20                  25                  30

Phe Tyr Tyr Gly Gly Cys Leu Ala Lys Arg Asn Asn Phe Glu Ser Ala
         35                  40                     45

Glu Asp Cys Met Arg Thr Cys Gly Gly Ala
    50                  55

(2) INFORMATION FOR SEQ ID NO: 284:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 284:

```
Arg Pro Asp Phe Cys Leu Glu Pro Pro Tyr Glu Gly Ile Cys Arg Ala
                  5                   10                      15

Tyr Phe Lys Arg Tyr Phe Tyr Asn Ala Lys Ala Gly Leu Cys Gln Thr
            20                  25                      30

Phe Glu Tyr Gly Gly Cys Leu Ala Lys Arg Asn Asn Phe Glu Ser Ala
            35              40                      45

Glu Asp Cys Met Arg Thr Cys Gly Gly Ala
        50              55
```

We claim:

1. A compound derived from bovine pancreatic trypsin inhibitor which inhibits Factor Xa with an inhibition constant less than 50 nM selected from the group consisting of:

BPTI (13Ile 15Arg 17Tyr 19Thr 39Leu 46Glu),
BPTI (1Ala 13Ile 15Arg 17Tyr 19Thr 39Leu 46Glu),
BPTI (1Ala 13Ile 15Arg 17Tyr 19Thr 39Leu),
BPTI (1Ala 13Ile 15Arg 17Tyr 19Thr 39Leu 46Glu),
BPTI (1Ala 13Ile 15Arg 17Tyr 19Thr 32Arg 39Leu 46Glu),
BPTI (1Ala 11Glu 13Ile 15Arg 17Tyr 19Thr 39Leu 46Glu),
BPTI (1Ala 13Ile 15Arg 17Tyr 39Leu),
BPTI (1Ala 13Phe 15Arg 17Tyr 39Thr 39Leu),
BPTI (1Ala 13Ile 15Arg 17Tyr 19Thr 39Phe),
BPTI (1Ala 13Ile 15Arg 17Phe 19Thr 39Leu),
BPTI (1Ala 15Arg 17Tyr 19Thr 39Tyr),
BPTI (1Ala 15Arg 17Tyr 19Thr 39Ile),
BPTI (1Ala 15Arg 17Tyr 19Thr 39Trp),
BPTI (1Ala 15Arg 17Tyr 19Thr 39Phe),
BPTI (1Ala 15Arg 17Tyr 19Thr 39His),
BPTI (1Ala 15Arg 17Tyr 19Thr 39Ser),
BPTI (1Ala 15Arg 17Tyr 19Thr 39Val),
BPTI (15Arg 16Gly 17Trp 18Phe 9Arg 20Gln),
BPTI (13Ile 15Arg 16Gly 17Trp 18Phe 19Arg 20Gln 39Leu),
BPTI (11Glu 13Ile 15Arg 16Gry 17Trp 18Phe 19Arg 20Gln 39Leu),
BPTI (15Arg 16Ala 17His 18Ile 19Thr 20Thr),
BPTI (13Ile 15Arg 16Ala 17His 18Ile 19Thr 20Thr 39Leu),
BPTI (11Glu 13Ile 15Arg 16Ala 17His 18Ile 19Thr 20Thr 39Leu),
BPTI (15Arg 16Ala 17His 18His 19Leu 20Val),
BPTI (13Ile 15Arg 16Ala 17His 18His 19Leu 20Val 39Leu),
BPTI (11Glu 13Ile 15Arg 16Ala 17His 18His 19Leu 20Val 39Leu),
BPTI (15Arg 16Ala 17His 18His 19Arg 20Glu),
BPTI (13Ile 15Arg 16Ala 17His 18His 19Arg 20Glu 39Leu),
BPTI (11Glu 13Ile 15Arg 16Ala 17His 18His 19Arg 20Glu 39Leu),
BPTI (15Arg 16Ala 17His 18Ile 19Arg 20Gln),
BPTI (13Ile 15Arg 16Ala 17His 18Ile 19Arg 20Gln 39Leu),
BPTI (11Glu 13Ile 15Arg 16Ala 17His 18Ile 19Arg 20Gln 39Leu),
BPTI (15Arg 16Gly 17His 18His 19Arg 20Glu 26Asn),
BPTI (13Ile 15Arg 16Gly 17His 18His 19Arg 20Glu 26Asn 39Leu),
BPTI (11Glu 13Ile 15Arg 16Gly 17His 18His 19Arg 20Glu 26Asn 39Leu),
BPTI (15Arg 16Ala 17Tyr 18Phe 19Asn 20Leu),
BPTI (13Ile 15Arg 16Ala 17Tyr 18Phe 19Asn 20Leu 39Leu),
BPTI (11Glu 13Ile 15Arg 16Ala 17Tyr 18Phe 19Asn 20Leu 39Leu),
BPTI (15Arg 16Ala 17His 18Val 19Arg 20His),
BPTI (13Ile 15Arg 16Ala 17His 18Val 19Arg 20His 39Leu), and
BPTI (11Glu 13Ile 15Arg 16Ala 17His 18Val 19Arg 20His 39Leu)
BPTI (13Ile 15Arg 17Asn 18Phe 19Lys 39Leu 46Glu)
BPTI (13Ile 15Arg 17Ser 18Phe 19Asn 39Leu 46Glu)
BPTI (13Ile 15Arg 17Ala 18Phe 19Lys 39Leu 46Glu)
BPTI (13Ile 15Arg 16Ser 17Tyr 18Phe 19Lys 39Leu 46Glu)
BPTI (13Ile 15Arg 17Ser 18Phe 19Lys 39Leu 46Glu)
BPTI (13Ile 15Arg 17His 18Tyr 19Lys 39Leu 46Glu)
BPTI (13Ile 15Arg 17Ser 18Phe 19Thr 39Leu 46Glu)
BPTI (13Ile 15Arg 17Ser 18Tyr 19Thr 39Leu 46Glu)
BPTI (13Ile 15Arg 17Ser 18Tyr 19Lys 39Leu 46Glu)
BPTI (13Ile 15Arg 17Met 18Phe 19His 39Leu 46Glu)
BPTI (13Ile 15Arg 17Ile 18Tyr 19Val 39Leu 46Glu)
BPTI (13Ile 15Arg 17Asn 18Phe 19Asn 39Leu 46Glu)
BPTI (13Ile 15Arg 17Tyr 18Tyr 19Lys 39Leu 46Glu)
BPTI (13Ile 15Arg 17Ala 18Phe 19Lys 39Leu 46Glu)
BPTI (13Ile 15Arg 17Leu 18His 39Leu 46Glu)
BPTI (13Ile 15Arg 17Ile 18Tyr 19Lys 39Leu 46Glu)
BPTI (13Ile 15Arg 17Ala 18Phe 19Asn 39Leu 46Glu)
BPTI (13Ile 15Arg 17Phe 18Tyr 19Lys 39Leu 46Glu)
BPTI (13Ile 15Arg 17Leu 18Tyr 19Lys 39Leu 46Glu)
BPTI (11Asp 15Arg 17Leu 18His 19Leu 34Tyr 39Leu 46Glu)
BPTI (11Pro 13Tyr 15Arg 17Leu 18His 19Leu 34Thr 39His 46Glu)
BPTI (11Thr 13Pro 15Arg 17Leu 18His 19His 34Phe 39Phe 46Glu)
BPTI (11Pro 13Ile 15Arg 17Leu 18His 19Pro 34His 39Leu 46Glu)
BPTI (11Val 13Ile 15Arg 17Leu 18His 19Thr 34Ser 39Phe 46Glu)

BPTI (11ser 13Leu 15Arg 17Leu 18His 19Lys 34Tyr 39Tyr 46Glu)
BPTI (11Leu 13Ile 15Arg 17Leu 18His 19Thr 34Ser 39Leu 46Glu)
BPTI (11Pro 13Ile 15Arg 17Leu 18His 19Lys 34His 39Phe 46Glu)
BPTI (11Ser 13Leu 15Arg 17Leu 18His 19Lys 34Tyr 39Phe 46Glu)
BPTI (11Pro 13Ile 15Arg 17Leu 18His 19Lys 34Tyr 39Met 46Glu)
BPTI (11Glu 13Met 15Arg 17Ile 18His 19Lys 34Thr 39Met 46Glu)
BPTI (11Pro 13Val 15Arg 17Leu 18His 19Lys 34Ser 39Gln 46Glu)
BPTI (11Arg 13Val 15Arg 17Ile 18His 19Lys 34Leu 39Met 46Glu)
BPTI (11Pro 13Leu 15Arg 17Leu 18His 19Lys 34Tyr 39Tyr 46Glu).
BPTI (11Ala 13Tyr 15Arg 17Leu 18His 19Lys 34Tyr 39Phe 46Glu)
BPTI (11Arg 13Val 15Arg 17Ile 18His 19Gln 34Ile 39Met 46Glu)
BPTI (11Thr 13Tyr 15Arg 17Leu 18His 19Lys 34Tyr 39Phe 46Glu)
BPTI (11Thr 13Ile 15Arg 17Leu 18His 19Lys 34Trp 39Leu 46Glu)
BPTI (11Gl 13Ile 15Arg 17Leu 18His 19Lys 34Met 39Leu 46Glu)
BPTI (11Pro 13Ile 15Arg 17Leu 18His 19Lys 34Tyr 39Met 46Glu)
BPTI (11Glu 13Leu 15Arg 17Leu 18His 19Lys 34Tyr 39Phe 46Glu)
BPTI (11Glu 13Phe 15Arg 17Tyr 18Phe 19Lys 34Thr 39Phe 46Glu)
BPTI (11Val 13Asp 15Arg 17Tyr 18Phe 19Lys 35Phe 39Leu 46Glu)
BPTI (11Glu 13Phe 15Arg 17His 18Phe 19Lys 32Ser 39Phe 46Glu)
BPTI (9Ala 11Glu 13Tyr 15Arg 17Tyr 18Ile 19Lys 23Phe 34His 39Phe 46Glu)
BPTI (11Thr 13His 15Arg 17Phe 18Phe 19Thr 39Phe 46Glu)
BPTI (11Thr 13His 15Arg 17Tyr 18Phe 19Lys 34Ile 39Phe 46Glu)
BPTI (9Ala 11Glu 13Phe 15Arg 17Tyr 18Phe 39Phe 46Glu)
BPTI (10His 11Ser 13Ile 15Arg 17Tyr 18Phe 19Thr 34His 39Phe 46Glu)
BPTI (11Glu 13Ile 15Arg 17Leu 18Phe 19Thr 34His 39Leu 46Glu)
BPTI (10Ser 11Glu 13Ile 15Arg 17Tyr 18His 19Lys 39Leu 46Glu)
BPTI (11Glu 13Asn 15Arg 17Phe 18Phe 19Arg 34Ile 39Leu 46Glu)
BPTI (11Leu 13Ile 15Arg 17Tyr 18Leu 19Lys 34Tyr 39Leu 46Glu)
BPTI (11Glu 13Asn 15Arg 17Tyr 18Leu 19Lys 34Ala 39Phe 46Glu)
BPTI (11Glu 13Ile 15Arg 17Tyr 18Phe 19Lys 34Ser 39Phe 46Glu)
BPTI (11Glu 13Ile 15Arg 17Phe 18Asn 19Lys 39Leu 46Glu)
BPTI (8Ser 11Ala 13Ile 15Arg 17Tyr 19Lys 34Tyr 39Phe 46Glu)
BPTI (11Glu 13Ile 15Arg 17Leu 18His 19Lys 34Tyr 39Leu 46Glu)
BPTI (11Glu 13Ile 15Arg 17Tyr 18Phe 19Lys 34Glu 39Leu 46Glu).

2. A pharmaceutical composition comprising a pharmaceutically acceptable carrier and a pharmaceutically effective amount of compound of claim.

3. The pharmaceutical composition of claim 2 for use in a mammal for preventing and/or treating a condition characterized by an elevated level of Factor Xa activity.

* * * * *